US008026366B2

(12) United States Patent
Prince et al.

(10) Patent No.: US 8,026,366 B2
(45) Date of Patent: Sep. 27, 2011

(54) ARYLOXY AND ARYLALKYLENEOXY SUBSTITUTED THIAZOLOQUINOLINES AND THIAZOLONAPHTHYRIDINES

(75) Inventors: Ryan B. Prince, St. Paul, MN (US); Michael J. Rice, Oakdale, MN (US); Joshua R. Wurst, North St. Paul, MN (US); Bryon A. Merrill, River Falls, WI (US); Tushar A. Kshirsagar, Woodbury, MN (US); Philip D. Heppner, Forest Lake, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 1260 days.

(21) Appl. No.: 11/570,704

(22) PCT Filed: Jun. 17, 2005

(86) PCT No.: PCT/US2005/021426
§ 371 (c)(1),
(2), (4) Date: Dec. 15, 2006

(87) PCT Pub. No.: WO2006/009826
PCT Pub. Date: Jan. 26, 2006

(65) Prior Publication Data
US 2007/0208052 A1 Sep. 6, 2007

Related U.S. Application Data

(60) Provisional application No. 60/581,297, filed on Jun. 18, 2004.

(51) Int. Cl.
*A61K 31/4365* (2006.01)
*C07D 513/04* (2006.01)
(52) U.S. Cl. ......................................... 546/80; 514/290
(58) Field of Classification Search .................... 546/80; 514/290
See application file for complete search history.

(56) References Cited

U.S. PATENT DOCUMENTS

| 3,314,941 A | 4/1967 | Littell et al. |
|---|---|---|
| 3,450,693 A | 6/1969 | Suzuki et al. |
| 3,670,086 A | 6/1972 | Pryor et al. |
| 3,692,907 A | 9/1972 | Fleming et al. |
| 3,891,660 A | 6/1975 | Denzel et al. |
| 3,899,508 A | 8/1975 | Wikel |
| 3,917,624 A | 11/1975 | Abu El-Haj et al. |
| 4,006,237 A | 2/1977 | Buckle et al. |
| 4,053,588 A | 10/1977 | Konig et al. |
| 4,381,344 A | 4/1983 | Rideout et al. |
| 4,552,874 A | 11/1985 | Mardin et al. |
| 4,563,525 A | 1/1986 | Campbell, Jr. |
| 4,593,821 A | 6/1986 | Brule |
| 4,668,686 A | 5/1987 | Meanwell et al. |
| 4,689,338 A | 8/1987 | Gerster |
| 4,690,930 A | 9/1987 | Takada et al. |
| 4,698,346 A | 10/1987 | Musser et al. |
| 4,698,348 A | 10/1987 | Gerster |
| 4,753,951 A | 6/1988 | Takada et al. |
| 4,758,574 A | 7/1988 | Robertson et al. |
| 4,774,339 A | 9/1988 | Haugland et al. |
| 4,775,674 A | 10/1988 | Meanwell et al. |
| 4,800,206 A | 1/1989 | Alig et al. |
| 4,826,830 A | 5/1989 | Han et al. |
| 4,837,378 A | 6/1989 | Borgman |
| 4,880,779 A | 11/1989 | Gallaher |
| 4,904,669 A | 2/1990 | Knoll et al. |
| 4,929,624 A | 5/1990 | Gerster et al. |
| 4,988,714 A | 1/1991 | Alig et al. |
| 4,988,815 A | 1/1991 | Andre et al. |
| 5,037,986 A | 8/1991 | Gerster |
| 5,175,296 A | 12/1992 | Gerster |
| 5,187,288 A | 2/1993 | Kang et al. |
| 5,225,183 A | 7/1993 | Purewal et al. |
| 5,238,944 A | 8/1993 | Wick et al. |
| 5,248,782 A | 9/1993 | Haugland et al. |
| 5,266,575 A | 11/1993 | Gerster |
| 5,268,376 A | 12/1993 | Gerster |
| 5,274,113 A | 12/1993 | Kang et al. |
| 5,342,784 A | 8/1994 | Yamada et al. |
| 5,346,905 A | 9/1994 | Gerster |
| 5,352,680 A | 10/1994 | Portoghese et al. |
| 5,352,784 A | 10/1994 | Nikolaides et al. |
| 5,367,076 A | 11/1994 | Gerster |
| 5,376,501 A | 12/1994 | Marien et al. |
| 5,378,848 A | 1/1995 | Takada et al. |
| 5,389,640 A | 2/1995 | Gerster et al. |
| 5,395,937 A | 3/1995 | Nikolaides et al. |

(Continued)

FOREIGN PATENT DOCUMENTS

AU    2004220534 A1    9/2004

(Continued)

OTHER PUBLICATIONS

Wozniak et al., "The Amination of 3-nitro-1, 5-naphthyridines by Liquid Ammonia/Potassium Permanganate[1,2]. A New and Convenient Amination Method." *Journal of the Royal Netherlands Chemical Society*, 102, pp. 511-513, Dec. 12, 1983.

Brennan et al., "Automated Bioassay of Interferons in Micro-test Plates.", *Biotechniques*, Jun./Jul. 78, 1983.

Testerman et al., "Cytokine Induction by the Immunomodulators Imiquimod and S-27609.", *Journal of Leukocyte Biology*, vol. 58, pp. 365-372, Sep. 1995.

Bachman et al., "Synthesis of Substituted Quinolylamines. Derivatives of 4-Amino-7-Chloroquinoline.", *J. Org. Chem*, 15, pp. 1278-1284 (1950).

Jain et al., "Chemical and Pharmacological Investigations of Some ω-Substituted Alkylamino-3-aminopyridines.", *J. Med. Chem.*, 11, pp. 87-92 (1968).

(Continued)

*Primary Examiner* — Rita Desai

(57) ABSTRACT

Thiazoloquinoline and thiazolonaphthyridine compounds having an aryloxy or arylalkyleneoxy substituent at the 6-, 7-, 8-, or 9-position, pharmaceutical compositions containing the compounds, intermediates, and methods of making and methods of use of these compounds as immunomodulators, for modulating cytokine biosynthesis in animals and in the treatment of diseases including viral and neoplastic diseases are disclosed.

13 Claims, No Drawings

U.S. PATENT DOCUMENTS

| | | | |
|---|---|---|---|
| 5,444,065 A | 8/1995 | Nikolaides et al. |
| 5,446,153 A | 8/1995 | Lindstrom et al. |
| 5,446,160 A | 8/1995 | Stucky et al. |
| 5,482,936 A | 1/1996 | Lindstrom |
| 5,494,916 A | 2/1996 | Lindstrom et al. |
| 5,500,228 A | 3/1996 | Lawter et al. |
| 5,525,612 A | 6/1996 | Gerster |
| 5,530,114 A | 6/1996 | Bennett et al. |
| 5,569,450 A | 10/1996 | Duan et al. |
| 5,571,819 A | 11/1996 | Sabb et al. |
| 5,578,727 A | 11/1996 | Andre et al. |
| 5,585,612 A | 12/1996 | Harp, Jr. |
| 5,602,256 A | 2/1997 | Andr e et al. |
| 5,605,899 A | 2/1997 | Gerster et al. |
| 5,612,377 A | 3/1997 | Crooks et al. |
| 5,627,281 A | 5/1997 | Nikolaides et al. |
| 5,644,063 A | 7/1997 | Lindstrom et al. |
| 5,648,516 A | 7/1997 | Nikolaides et al. |
| 5,693,811 A | 12/1997 | Lindstrom |
| 5,714,608 A | 2/1998 | Gerster |
| 5,731,193 A | 3/1998 | Mori et al. |
| 5,736,553 A | 4/1998 | Wick et al. |
| 5,741,908 A | 4/1998 | Gerster et al. |
| 5,741,909 A | 4/1998 | Gerster et al. |
| 5,750,134 A | 5/1998 | Scholz et al. |
| 5,756,747 A | 5/1998 | Gerster et al. |
| 5,776,432 A | 7/1998 | Schultz et al. |
| 5,780,045 A | 7/1998 | McQuinn et al. |
| 5,837,809 A | 11/1998 | Grandy et al. |
| 5,840,744 A | 11/1998 | Borgman |
| 5,854,257 A | 12/1998 | Armitage et al. |
| 5,861,268 A | 1/1999 | Tang et al. |
| 5,886,006 A | 3/1999 | Nikolaides et al. |
| 5,939,047 A | 8/1999 | Jernberg |
| 5,939,090 A | 8/1999 | Beaurline et al. |
| 5,962,479 A | 10/1999 | Chen |
| 5,962,636 A | 10/1999 | Bachmaier et al. |
| 5,977,366 A | 11/1999 | Gerster et al. |
| 6,028,076 A | 2/2000 | Hirota et al. |
| 6,039,969 A | 3/2000 | Tomai et al. |
| 6,057,371 A | 5/2000 | Glennon |
| 6,069,140 A | 5/2000 | Sessler et al. |
| 6,069,149 A | 5/2000 | Nanba et al. |
| 6,071,949 A | 6/2000 | Mulshine et al. |
| 6,077,349 A | 6/2000 | Kikuchi |
| 6,083,505 A | 7/2000 | Miller et al. |
| 6,110,929 A * | 8/2000 | Gerster et al. | ................ 514/293 |
| 6,113,918 A | 9/2000 | Johnson et al. |
| 6,121,323 A | 9/2000 | Merrill |
| 6,123,957 A | 9/2000 | Jernberg |
| 6,126,938 A | 10/2000 | Guy et al. |
| 6,194,388 B1 | 2/2001 | Krieg et al. |
| 6,194,425 B1 | 2/2001 | Gerster et al. |
| 6,200,592 B1 | 3/2001 | Tomai et al. |
| 6,207,646 B1 | 3/2001 | Krieg et al. |
| 6,239,116 B1 | 5/2001 | Krieg et al. |
| 6,245,776 B1 | 6/2001 | Skwierczynski et al. |
| 6,294,271 B1 | 9/2001 | Sumita et al. |
| 6,303,347 B1 | 10/2001 | Johnson et al. |
| 6,309,623 B1 | 10/2001 | Weers et al. |
| 6,315,985 B1 | 11/2001 | Wu et al. |
| 6,323,200 B1 | 11/2001 | Gerster et al. |
| 6,329,381 B1 | 12/2001 | Kurimoto et al. |
| 6,331,539 B1 | 12/2001 | Crooks et al. |
| 6,339,068 B1 | 1/2002 | Krieg et al. |
| 6,348,462 B1 | 2/2002 | Gerster et al. |
| 6,365,166 B2 | 4/2002 | Beaurline et al. |
| 6,376,501 B1 | 4/2002 | Isobe et al. |
| 6,376,669 B1 | 4/2002 | Rice et al. |
| 6,387,383 B1 | 5/2002 | Dow et al. |
| 6,387,938 B1 | 5/2002 | Mizuguchi et al. |
| 6,406,705 B1 | 6/2002 | Davis et al. |
| 6,426,334 B1 | 7/2002 | Agrawal et al. |
| 6,440,992 B1 | 8/2002 | Gerster et al. |
| 6,451,485 B1 | 9/2002 | James et al. |
| 6,451,810 B1 | 9/2002 | Coleman et al. |
| 6,465,654 B2 | 10/2002 | Gerster et al. |
| 6,476,000 B1 | 11/2002 | Agrawal |
| 6,486,168 B1 | 11/2002 | Skwierczynski et al. |
| 6,486,186 B2 | 11/2002 | Fowler et al. |
| 6,511,485 B2 | 1/2003 | Hirt et al. |
| 6,514,985 B1 | 2/2003 | Gerster et al. |
| 6,518,239 B1 | 2/2003 | Kuo et al. |
| 6,518,265 B1 | 2/2003 | Kato et al. |
| 6,518,280 B2 | 2/2003 | Gerster et al. |
| 6,525,028 B1 | 2/2003 | Johnson et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,582,957 B1 | 6/2003 | Turner, Jr. et al. |
| 6,610,319 B2 | 8/2003 | Tomai et al. |
| 6,627,638 B2 | 9/2003 | Gerster et al. |
| 6,627,639 B2 | 9/2003 | Stack et al. |
| 6,627,640 B2 * | 9/2003 | Gerster et al. | ................ 514/301 |
| 6,630,588 B2 | 10/2003 | Rice et al. |
| 6,638,944 B2 | 10/2003 | Mickelson |
| 6,649,172 B2 | 11/2003 | Johnson |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,334 B2 * | 1/2004 | Gerster et al. | ............. 514/232.8 |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,076 B2 | 2/2004 | Tomai et al. |
| 6,696,465 B2 | 2/2004 | Dellaria et al. |
| 6,703,402 B2 | 3/2004 | Gerster et al. |
| 6,706,728 B2 | 3/2004 | Hedenstrom et al. |
| 6,716,988 B2 | 4/2004 | Dellaria et al. |
| 6,720,333 B2 | 4/2004 | Dellaria et al. |
| 6,720,334 B2 | 4/2004 | Dellaria et al. |
| 6,720,422 B2 | 4/2004 | Dellaria et al. |
| 6,743,920 B2 | 6/2004 | Lindstrom et al. |
| 6,756,382 B2 | 6/2004 | Coleman et al. |
| 6,780,873 B2 | 8/2004 | Crooks et al. |
| 6,784,188 B2 | 8/2004 | Crooks et al. |
| 6,790,961 B2 | 9/2004 | Gerster et al. |
| 6,797,718 B2 | 9/2004 | Dellaria et al. |
| 6,800,624 B2 | 10/2004 | Crooks et al. |
| 6,818,650 B2 | 11/2004 | Griesgraber |
| 6,825,350 B2 | 11/2004 | Crooks et al. |
| 6,841,678 B2 | 1/2005 | Merli et al. |
| 6,852,861 B2 | 2/2005 | Merli et al. |
| 6,855,217 B2 | 2/2005 | Suzuki |
| 6,855,350 B2 | 2/2005 | Lu |
| 6,878,719 B2 | 4/2005 | Lindstrom et al. |
| 6,888,000 B2 | 5/2005 | Crooks et al. |
| 6,894,060 B2 | 5/2005 | Slade |
| 6,894,165 B2 | 5/2005 | Gerster et al. |
| 6,897,221 B2 | 5/2005 | Crooks et al. |
| 6,900,016 B1 | 5/2005 | Venter et al. |
| 6,903,113 B2 | 6/2005 | Heppner et al. |
| 6,916,925 B1 | 7/2005 | Rice et al. |
| 6,921,826 B2 | 7/2005 | Dellaria et al. |
| 6,924,293 B2 | 8/2005 | Lindstrom |
| 6,943,240 B2 | 9/2005 | Bauer et al. |
| 6,943,255 B2 | 9/2005 | Lindstrom et al. |
| 6,949,649 B2 | 9/2005 | Bonk et al. |
| 6,953,804 B2 | 10/2005 | Dellaria et al. |
| 6,969,722 B2 | 11/2005 | Heppner et al. |
| 6,989,389 B2 | 1/2006 | Heppner et al. |
| 7,030,129 B2 | 4/2006 | Miller et al. |
| 7,030,131 B2 | 4/2006 | Crooks et al. |
| 7,038,053 B2 | 5/2006 | Lindstrom et al. |
| 7,049,439 B2 | 5/2006 | Crooks et al. |
| 7,078,253 B2 | 7/2006 | Brunner et al. |
| 7,078,523 B2 | 7/2006 | Crooks et al. |
| 7,091,214 B2 | 8/2006 | Hays et al. |

| Patent/Publication | Date | Inventor |
|---|---|---|
| 7,098,221 B2 | 8/2006 | Heppner et al. |
| 7,112,677 B2 | 9/2006 | Griesgraber |
| 7,115,622 B2 | 10/2006 | Crooks et al. |
| 7,125,890 B2 | 10/2006 | Dellaria et al. |
| 7,132,429 B2 | 11/2006 | Griesgraber et al. |
| 7,163,947 B2 | 1/2007 | Griesgraber et al. |
| 7,179,253 B2 | 2/2007 | Graham et al. |
| 7,199,131 B2 | 4/2007 | Lindstrom |
| 7,214,675 B2 | 5/2007 | Griesgraber |
| 7,220,758 B2 | 5/2007 | Dellaria et al. |
| 7,226,928 B2 | 6/2007 | Mitra et al. |
| 7,276,515 B2 | 10/2007 | Dellaria et al. |
| 7,288,550 B2 | 10/2007 | Dellaria et al. |
| 7,375,180 B2 | 5/2008 | Gorden et al. |
| 7,387,271 B2 | 6/2008 | Noelle et al. |
| 7,393,859 B2 | 7/2008 | Coleman et al. |
| 7,427,629 B2 | 9/2008 | Kedl et al. |
| 7,544,697 B2 | 6/2009 | Hays et al. |
| 7,598,382 B2 | 10/2009 | Hays et al. |
| 7,612,083 B2 | 11/2009 | Griesgraber |
| 7,648,997 B2 | 1/2010 | Kshirsagar et al. |
| 2001/0046968 A1 | 11/2001 | Zagon et al. |
| 2002/0016332 A1 | 2/2002 | Slade |
| 2002/0055517 A1 | 5/2002 | Smith |
| 2002/0058674 A1 | 5/2002 | Hedenstrom et al. |
| 2002/0107262 A1 | 8/2002 | Lindstrom |
| 2002/0110840 A1 | 8/2002 | Tomai et al. |
| 2002/0137101 A1 | 9/2002 | Meyers |
| 2002/0173655 A1 | 11/2002 | Dellaria et al. |
| 2002/0193729 A1 | 12/2002 | Cormier et al. |
| 2003/0022302 A1 | 1/2003 | Lewis et al. |
| 2003/0044429 A1 | 3/2003 | Aderem et al. |
| 2003/0082108 A1 | 5/2003 | Mulshine et al. |
| 2003/0088102 A1 | 5/2003 | Matsubara et al. |
| 2003/0096835 A1 | 5/2003 | Crooks et al. |
| 2003/0096998 A1 | 5/2003 | Gerster et al. |
| 2003/0130299 A1 | 7/2003 | Crooks et al. |
| 2003/0133733 A1 | 7/2003 | Korhonen |
| 2003/0133913 A1 | 7/2003 | Tomai et al. |
| 2003/0139364 A1 | 7/2003 | Krieg et al. |
| 2003/0144283 A1 | 7/2003 | Coleman et al. |
| 2003/0144286 A1 | 7/2003 | Frenkel et al. |
| 2003/0158192 A1 | 8/2003 | Crooks et al. |
| 2003/0161797 A1 | 8/2003 | Miller et al. |
| 2003/0172391 A1 | 9/2003 | Turner et al. |
| 2003/0185835 A1 | 10/2003 | Braun |
| 2003/0187016 A1 | 10/2003 | Crooks et al. |
| 2003/0199461 A1 | 10/2003 | Averett et al. |
| 2003/0199538 A1 | 10/2003 | Skwierczynski et al. |
| 2003/0212092 A1 | 11/2003 | Heppner et al. |
| 2003/0216481 A1 | 11/2003 | Jia |
| 2003/0232074 A1 | 12/2003 | Lipford et al. |
| 2003/0232763 A1 | 12/2003 | Jia |
| 2003/0232852 A1 | 12/2003 | Lindstrom et al. |
| 2004/0010007 A1 | 1/2004 | Dellaria et al. |
| 2004/0014779 A1 | 1/2004 | Gorden et al. |
| 2004/0023870 A1 | 2/2004 | Dedera et al. |
| 2004/0067975 A1 | 4/2004 | Crooks et al. |
| 2004/0072858 A1 | 4/2004 | Charles et al. |
| 2004/0076633 A1 | 4/2004 | Thomsen et al. |
| 2004/0091491 A1 | 5/2004 | Kedl et al. |
| 2004/0092545 A1 | 5/2004 | Crooks et al. |
| 2004/0097542 A1 | 5/2004 | Crooks et al. |
| 2004/0106638 A1 | 6/2004 | Lindstrom |
| 2004/0132079 A1 | 7/2004 | Gupta et al. |
| 2004/0132748 A1 | 7/2004 | Isobe et al. |
| 2004/0132766 A1 | 7/2004 | Griesgraber |
| 2004/0141950 A1 | 7/2004 | Noelle et al. |
| 2004/0147543 A1 | 7/2004 | Hays et al. |
| 2004/0157874 A1 | 8/2004 | Crooks et al. |
| 2004/0162309 A1 | 8/2004 | Gorden et al. |
| 2004/0167157 A1 | 8/2004 | Masui et al. |
| 2004/0171086 A1 | 9/2004 | Fink et al. |
| 2004/0175336 A1 | 9/2004 | Egging et al. |
| 2004/0176367 A1 | 9/2004 | Griesgraber et al. |
| 2004/0180919 A1 | 9/2004 | Lee et al. |
| 2004/0181130 A1 | 9/2004 | Fox et al. |
| 2004/0181211 A1 | 9/2004 | Elliott et al. |
| 2004/0191833 A1 | 9/2004 | Fink et al. |
| 2004/0192585 A1 | 9/2004 | Fox et al. |
| 2004/0197865 A1 | 10/2004 | Gupta et al. |
| 2004/0202720 A1 | 10/2004 | Wightman et al. |
| 2004/0204436 A1 | 10/2004 | Gerster et al. |
| 2004/0214851 A1 | 10/2004 | Birmachu et al. |
| 2004/0258698 A1 | 12/2004 | Wightman et al. |
| 2004/0265351 A1 | 12/2004 | Miller et al. |
| 2005/0009858 A1 | 1/2005 | Martinez-Colon et al. |
| 2005/0032829 A1 | 2/2005 | Lindstrom et al. |
| 2005/0048072 A1 | 3/2005 | Kedl et al. |
| 2005/0054590 A1 | 3/2005 | Averett |
| 2005/0054640 A1 | 3/2005 | Griesgraber et al. |
| 2005/0054665 A1 | 3/2005 | Miller et al. |
| 2005/0059072 A1 | 3/2005 | Birmachu et al. |
| 2005/0070460 A1 | 3/2005 | Hammerbeck et al. |
| 2005/0085500 A1 | 4/2005 | Gutman et al. |
| 2005/0096259 A1 | 5/2005 | Tomai et al. |
| 2005/0119273 A1 | 6/2005 | Lipford et al. |
| 2005/0136065 A1 | 6/2005 | Valiante |
| 2005/0148620 A1 | 7/2005 | Crooks et al. |
| 2005/0158325 A1 | 7/2005 | Hammerbeck et al. |
| 2005/0165236 A1 | 7/2005 | Colombo et al. |
| 2005/0171072 A1 | 8/2005 | Tomai et al. |
| 2005/0226878 A1 | 10/2005 | Tomai et al. |
| 2005/0234088 A1 | 10/2005 | Griesgraber |
| 2005/0239733 A1 | 10/2005 | Jurk et al. |
| 2005/0239735 A1 | 10/2005 | Miller et al. |
| 2005/0245562 A1 | 11/2005 | Garcia-Echeverria et al. |
| 2005/0267145 A1 | 12/2005 | Merrill et al. |
| 2005/0281813 A1 | 12/2005 | Dedera et al. |
| 2006/0009482 A1 | 1/2006 | Tomai et al. |
| 2006/0100229 A1 | 5/2006 | Hays et al. |
| 2006/0106052 A1 | 5/2006 | Crooks et al. |
| 2006/0188913 A1 | 8/2006 | Krieg et al. |
| 2007/0060754 A1 | 3/2007 | Lindstrom et al. |
| 2007/0066639 A1 | 3/2007 | Kshirsagar et al. |
| 2007/0072893 A1 | 3/2007 | Krepski et al. |
| 2007/0099901 A1 | 5/2007 | Krepski et al. |
| 2007/0155767 A1 | 7/2007 | Radmer et al. |
| 2007/0166384 A1 | 7/2007 | Zarraga |
| 2007/0167476 A1 | 7/2007 | Kshirsagar et al. |
| 2007/0213356 A1 | 9/2007 | Merrill et al. |
| 2007/0219196 A1 | 9/2007 | Krepski et al. |
| 2007/0219228 A1 | 9/2007 | Niwas et al. |
| 2007/0259881 A1 | 11/2007 | Dellaria et al. |
| 2007/0259907 A1 | 11/2007 | Prince |
| 2007/0287725 A1 | 12/2007 | Miser et al. |
| 2007/0292456 A1 | 12/2007 | Hammerbeck et al. |
| 2008/0015184 A1 | 1/2008 | Kshirsagar et al. |
| 2008/0070907 A1 | 3/2008 | Griesgraber et al. |
| 2008/0085895 A1 | 4/2008 | Griesgraber et al. |
| 2008/0114019 A1 | 5/2008 | Kshirsagar et al. |
| 2008/0119508 A1 | 5/2008 | Slade et al. |
| 2008/0207674 A1 | 8/2008 | Stoesz et al. |
| 2008/0269192 A1 | 10/2008 | Griesgraber et al. |
| 2008/0306252 A1 | 12/2008 | Crooks et al. |
| 2008/0312434 A1 | 12/2008 | Lindstrom et al. |
| 2008/0318998 A1 | 12/2008 | Prince et al. |
| 2009/0005371 A1 | 1/2009 | Rice et al. |
| 2009/0017076 A1 | 1/2009 | Miller et al. |
| 2009/0018122 A1 | 1/2009 | Lindstrom et al. |
| 2009/0023722 A1 | 1/2009 | Coleman et al. |
| 2009/0029988 A1 | 1/2009 | Kshirsagar et al. |
| 2009/0030030 A1 | 1/2009 | Bonk et al. |
| 2009/0030031 A1 | 1/2009 | Kshirsagar et al. |
| 2009/0042925 A1 | 2/2009 | Kshirsagar et al. |
| 2009/0062272 A1 | 3/2009 | Bonk et al. |
| 2009/0062328 A1 | 3/2009 | Kshirsagar et al. |
| 2009/0069299 A1 | 3/2009 | Merrill et al. |
| 2009/0069314 A1 | 3/2009 | Kshirsagar et al. |
| 2009/0075980 A1 | 3/2009 | Hays et al. |
| 2009/0099161 A1 | 4/2009 | Rice et al. |
| 2009/0105295 A1 | 4/2009 | Kshirsagar et al. |
| 2009/0124611 A1 | 5/2009 | Hays et al. |
| 2009/0163532 A1 | 6/2009 | Perman et al. |
| 2009/0163533 A1 | 6/2009 | Hays et al. |
| 2009/0176821 A1 | 7/2009 | Kshirsagar et al. |
| 2009/0240055 A1 | 9/2009 | Krepski et al. |
| 2009/0253695 A1 | 10/2009 | Kshirsagar et al. |

| | | | |
|---|---|---|---|
| 2009/0270443 A1 | 10/2009 | Stoermer et al. | |
| 2009/0318435 A1 | 12/2009 | Hays et al. | |
| 2010/0113565 A1 | 5/2010 | Gorden et al. | |

FOREIGN PATENT DOCUMENTS

| | | | |
|---|---|---|---|
| AU | 2004229478 A1 | 10/2004 | |
| AU | 2004264336 A1 | 2/2005 | |
| AU | 2004268625 A1 | 3/2005 | |
| AU | 2002239547 B2 | 11/2006 | |
| CA | 2044087 A1 | 12/1991 | |
| CA | 2158996 A1 | 10/1994 | |
| CN | 1354663 A | 6/2002 | |
| EP | 0 145 340 A2 | 6/1985 | |
| EP | 0 223 420 A1 | 5/1987 | |
| EP | 0 310 950 A1 | 4/1989 | |
| EP | 0 385 630 A2 | 9/1990 | |
| EP | 0 389 302 A1 | 9/1990 | |
| EP | 0 394 026 | 10/1990 | |
| EP | 0 425 306 A2 | 5/1991 | |
| EP | 0 510 260 A2 | 10/1992 | |
| EP | 0 645 389 A1 | 3/1995 | |
| EP | 0 778 277 A1 | 6/1997 | |
| EP | 0 894 797 A1 | 2/1999 | |
| EP | 1 082 960 A2 | 3/2001 | |
| EP | 1 097 709 A2 | 5/2001 | |
| EP | 1 104 764 | 6/2001 | |
| EP | 1 145 340 A2 | 10/2001 | |
| EP | 1 256 582 A1 | 11/2002 | |
| EP | 1 341 791 A2 | 9/2003 | |
| EP | 1 495 758 A2 | 1/2005 | |
| HU | 34479 A2 | 3/1985 | |
| HU | 210051 A2 | 6/1991 | |
| HU | 218950 A2 | 9/1995 | |
| IL | 73534 A | 12/1990 | |
| JP | 53050197 A | 5/1978 | |
| JP | 63010787 A | 1/1988 | |
| JP | 4066571 A | 3/1992 | |
| JP | 4327587 A | 11/1992 | |
| JP | 5286973 A | 11/1993 | |
| JP | 9-208584 | 8/1997 | |
| JP | 11-080156 A | 3/1999 | |
| JP | 11-222432 | 8/1999 | |
| JP | 2000-247884 | 9/2000 | |
| NZ | 545412 A | 12/2008 | |
| RU | 2076105 C1 | 3/1997 | |
| RU | 2127273 C1 | 3/1999 | |
| RU | 2221798 C2 | 1/2004 | |
| WO | WO-91/06682 A1 | 5/1991 | |
| WO | WO-92/06093 A1 | 4/1992 | |
| WO | WO-92/15581 A1 | 9/1992 | |
| WO | WO-92/15582 A1 | 9/1992 | |
| WO | WO-93/05042 A1 | 3/1993 | |
| WO | WO-93/09119 A1 | 5/1993 | |
| WO | WO-93/20847 A1 | 10/1993 | |
| WO | WO-94/10171 A1 | 5/1994 | |
| WO | WO-95/02597 A1 | 1/1995 | |
| WO | WO-95/02598 A1 | 1/1995 | |
| WO | WO-96/11199 A1 | 4/1996 | |
| WO | WO-96/21663 A1 | 7/1996 | |
| WO | WO-97/48703 A1 | 12/1997 | |
| WO | WO-97/48704 A1 | 12/1997 | |
| WO | WO-98/17279 A1 | 4/1998 | |
| WO | WO-98/30562 A1 | 7/1998 | |
| WO | WO-98/48805 A1 | 11/1998 | |
| WO | WO-98/50547 A2 | 11/1998 | |
| WO | WO-98/54226 A1 | 12/1998 | |
| WO | WO-99/18105 A1 | 4/1999 | |
| WO | WO-99/29693 A1 | 6/1999 | |
| WO | WO-00/06577 A1 | 2/2000 | |
| WO | WO-00/09506 A1 | 2/2000 | |
| WO | WO-00/19987 A1 | 4/2000 | |
| WO | WO-00/40228 A2 | 7/2000 | |
| WO | WO-00/47719 A2 | 8/2000 | |
| WO | WO-00/75304 A1 | 12/2000 | |
| WO | WO-00/76505 A1 | 12/2000 | |
| WO | WO-00/76518 A1 | 12/2000 | |
| WO | WO-00/76519 A1 | 12/2000 | |
| WO | WO-01/34709 A1 | 5/2001 | |
| WO | WO-01/51486 A2 | 7/2001 | |
| WO | WO-01/55439 A1 | 8/2001 | |
| WO | WO-01/58900 A1 | 8/2001 | |
| WO | WO-01/74343 A2 | 10/2001 | |
| WO | WO-01/74821 A1 | 10/2001 | |
| WO | WO-02/07725 A1 | 1/2002 | |
| WO | WO-02/22809 A2 | 3/2002 | |
| WO | WO-02/24225 A1 | 3/2002 | |
| WO | WO 02/36592 | 5/2002 | |
| WO | WO-02/46188 A2 | 6/2002 | |
| WO | WO-02/46189 A2 | 6/2002 | |
| WO | WO-02/46190 A2 | 6/2002 | |
| WO | WO-02/46191 A2 | 6/2002 | |
| WO | WO-02/46192 A2 | 6/2002 | |
| WO | WO-02/46193 A2 | 6/2002 | |
| WO | WO-02/46194 A2 | 6/2002 | |
| WO | WO-02/46749 A2 | 6/2002 | |
| WO | WO-02/085905 A1 | 10/2002 | |
| WO | WO-02/102377 A1 | 12/2002 | |
| WO | WO-03/008421 A1 | 1/2003 | |
| WO | WO-03/009852 A1 | 2/2003 | |
| WO | WO-03/020889 A2 | 3/2003 | |
| WO | WO-03/043572 A2 | 5/2003 | |
| WO | WO-03/045391 A1 | 6/2003 | |
| WO | WO-03/045494 A2 | 6/2003 | |
| WO | WO-03/045929 A2 | 6/2003 | |
| WO | WO-03/050117 A1 | 6/2003 | |
| WO | WO-03/050118 A1 | 6/2003 | |
| WO | WO-03/050119 A2 | 6/2003 | |
| WO | WO-03/050121 A1 | 6/2003 | |
| WO | WO-03/077944 A1 | 9/2003 | |
| WO | WO-03/080114 A2 | 10/2003 | |
| WO | WO-03/086280 A2 | 10/2003 | |
| WO | WO-03/086350 A1 | 10/2003 | |
| WO | WO-03/089602 A2 | 10/2003 | |
| WO | WO-03/097641 A2 | 11/2003 | |
| WO | WO-03/101949 A2 | 12/2003 | |
| WO | WO-03/103584 A2 | 12/2003 | |
| WO | WO-2004/028539 A2 | 4/2004 | |
| WO | WO-2004/041285 A1 | 5/2004 | |
| WO | WO-2004/043913 A2 | 5/2004 | |
| WO | WO-2004/053057 A2 | 6/2004 | |
| WO | WO-2004/053452 A2 | 6/2004 | |
| WO | WO-2004/058759 A1 | 7/2004 | |
| WO | WO-2004/071459 A2 | 8/2004 | |
| WO | WO-2004/075865 A2 | 9/2004 | |
| WO | WO-2004/080398 A2 | 9/2004 | |
| WO | WO-2004/091500 A2 | 10/2004 | |
| WO | WO-2004/096144 A2 | 11/2004 | |
| WO | WO-2004/110991 A2 | 12/2004 | |
| WO | WO-2004/110992 A2 | 12/2004 | |
| WO | WO-2005/003064 A2 | 1/2005 | |
| WO | WO-2005/003065 A2 | 1/2005 | |
| WO | WO-2005/016273 A2 | 2/2005 | |
| WO | WO-2005/016275 A2 | 2/2005 | |
| WO | WO 2005/018551 | 3/2005 | |
| WO | WO 2005/018555 | 3/2005 | |
| WO | WO 2005/018556 | 3/2005 | |
| WO | WO 2005/020999 | 3/2005 | |
| WO | WO-2005/023190 A2 | 3/2005 | |
| WO | WO-2005/025614 A2 | 3/2005 | |
| WO | WO-2005/029037 A2 | 3/2005 | |
| WO | WO 2005/032484 | 4/2005 | |
| WO | WO-2005/041891 A2 | 5/2005 | |
| WO | WO 2005/048933 | 6/2005 | |
| WO | WO 2005/048945 | 6/2005 | |
| WO | WO-2005/049076 A1 | 6/2005 | |
| WO | WO 2005/051317 | 6/2005 | |
| WO | WO 2005/051324 | 6/2005 | |
| WO | WO 2005/054237 | 6/2005 | |
| WO | WO 2005/054238 | 6/2005 | |
| WO | WO-2005/065678 A1 | 7/2005 | |
| WO | WO 2005/066169 | 7/2005 | |
| WO | WO 2005/066170 | 7/2005 | |
| WO | WO 2005/066172 | 7/2005 | |
| WO | WO-2005/067500 A2 | 7/2005 | |
| WO | WO 2005/076783 | 8/2005 | |
| WO | WO 2005/079195 | 9/2005 | |
| WO | WO 2005/094531 | 10/2005 | |
| WO | WO-2005/110013 A2 | 11/2005 | |

| WO | WO 2005/123079 | 12/2005 |
| --- | --- | --- |
| WO | WO 2005/123080 | 12/2005 |
| WO | WO 2006/009826 | 1/2006 |
| WO | WO 2006/009832 | 1/2006 |
| WO | WO 2006/026760 | 3/2006 |
| WO | WO 2006/028451 | 3/2006 |
| WO | WO 2006/028545 | 3/2006 |
| WO | WO 2006/028962 | 3/2006 |
| WO | WO 2006/029115 | 3/2006 |
| WO | WO 2006/031878 | 3/2006 |
| WO | WO 2006/038923 | 4/2006 |
| WO | WO-2006/063072 A2 | 6/2006 |
| WO | WO-2006/063152 A2 | 6/2006 |
| WO | WO 2006/065280 | 6/2006 |
| WO | WO-2006/073940 A2 | 7/2006 |
| WO | WO 2006/074003 | 7/2006 |
| WO | WO-2006/074045 A2 | 7/2006 |
| WO | WO 2006/004737 | 8/2006 |
| WO | WO 2006/083400 | 8/2006 |
| WO | WO 2006/083440 | 8/2006 |
| WO | WO-2006/084251 A2 | 8/2006 |
| WO | WO 2006/086449 | 8/2006 |
| WO | WO 2006/086633 | 8/2006 |
| WO | WO-2006/086634 A2 | 8/2006 |
| WO | WO 2006/091394 | 8/2006 |
| WO | WO 2006/091567 | 8/2006 |
| WO | WO 2006/091568 | 8/2006 |
| WO | WO 2006/091647 | 8/2006 |
| WO | WO-2006/093514 A2 | 9/2006 |
| WO | WO 2006/098852 | 9/2006 |
| WO | WO-2006/107753 A2 | 10/2006 |
| WO | WO 2006/107771 | 10/2006 |
| WO | WO 2006/107851 | 10/2006 |
| WO | WO 2006/107853 | 10/2006 |
| WO | WO 2006/121528 | 11/2006 |
| WO | WO-2006/122806 A2 | 11/2006 |
| WO | WO-2007/028129 A1 | 3/2007 |
| WO | WO-2007/030775 A2 | 3/2007 |
| WO | WO-2007/030777 A2 | 3/2007 |
| WO | WO-2007/035935 A1 | 3/2007 |
| WO | WO-2007/056112 A2 | 5/2007 |
| WO | WO-2007/062043 A1 | 5/2007 |
| WO | WO-2007/075468 A1 | 7/2007 |
| WO | WO-2007/079086 A1 | 7/2007 |
| WO | WO-2007/079146 A1 | 7/2007 |
| WO | WO-2007/079169 A2 | 7/2007 |
| WO | WO-2007/079171 A2 | 7/2007 |
| WO | WO-2007/079202 A2 | 7/2007 |
| WO | WO-2007/079203 A2 | 7/2007 |
| WO | WO-2007/092641 A2 | 8/2007 |
| WO | WO-2007/106852 A2 | 9/2007 |
| WO | WO-2007/106854 A2 | 9/2007 |
| WO | WO-2007/120121 A2 | 10/2007 |
| WO | WO-2007/143526 A2 | 12/2007 |
| WO | WO-2008/008432 A2 | 1/2008 |
| WO | WO-2008/030511 A2 | 3/2008 |
| WO | WO-2008/036312 A1 | 3/2008 |
| WO | WO-2008/045543 A1 | 4/2008 |

OTHER PUBLICATIONS

Baranov et al., "Pyrazoles, Imidazoles, and Other 5-Membered Rings.", *Chem. Abs.* 85, 94362, (1976).
Berényi et al., "Ring Transformation of Condensed Dihydro-as-triazines.", *J. Heterocyclic Chem.*, 18, pp. 1537-1540 (1981).
Chollet et al., "Development of a Topically Active Imiquimod Formulation.", *Pharmaceutical Development and Technology*, 4(1), pp. 35-43 (1999).
Izumi et al., "1H-Imidazo[4,5-c]quinoline Derivatives as Novel Potent TNF-α Suppressors: Synthesis and Structure-Activity Relationship of 1-, 2- and 4-Substituted 1H-imidazo[4,5-c]pyridines.", *Bioorganic &Medicinal Chemistry*, 11, pp. 2541-2550 (2003).
International Search Report and Written Opinion for PCT/US2005/021426 mailed Nov. 22, 2005.
International Preliminary Report on Patentability for PCT/US2005/021426 mailed Dec. 20, 2006.
[No Author Listed] "Comparative Tests." Filed Apr. 8, 2005 during prosecution for EP 00938205.2, EP 00950215.4 and EP 00938211.0 in the name of 3M Innovative Properties Co.
[No Author Listed] Chemical Abstracts. 1964;61(1):6060g.
[No Author Listed] Encyclopedia of Pharmaceutical Technology. 2nd Ed. Marcel Dekker, Inc. 2002:856-60.
Agrawal et al., Synthetic agonists of Toll-like receptors 7, 8 and 9. Biochem Soc Trans. Dec. 2007;35(Pt 6):1461-7.
Ahmed et al., A new rapid and simple non-radioactive assay to monitor and determine the proliferation of lymphocytes: an alternative to [3H]thymidine incorporation assay. J Immunol Methods. Apr. 15, 1994;170(2):211-24.
Akira et al., Recognition of pathogen-associated molecular patterns by TLR family. Immunol Lett. 2003;85:85-95.
Akira et al., Toll-like receptors: critical proteins linking innate and acquired immunity. Nature Immunol. 2001;2(8):675-80.
Alexopoulou et al., Recognition of double-stranded RNA and activation of NF-kappaB by Toll-like receptor 3. Nature. Oct. 18, 2001;413(6857):732-8.
Assuma et al., IL-1 and TNF Antagonists Inhibit the Inflammatory Response and Bone Loss in Experimental Periodontitis. J Immunol. 2000;160:403-09.
Au et al., Virus-mediated induction of interferon A gene requires cooperation between multiple binding factors in the interferon alpha promoter region. J Biol Chem. Nov. 15, 1993;268(32):24032-40.
Auerbach et al., Erythema nodosum following a jellyfish sting. J Emerg Med. Nov.-Dec. 1987;5(6):487-91.
Auwers, [Uber die Isomerie-Verhaltnisse in der Pyrazol-Reihe. Berichte. VI.] 1926;601-607. German.
Baffis et al., Use of interferon for prevention of hepatocellular carcinoma in cirrhotic patients with hepatitis B or hepatitis C virus infection. Ann Intern Med. Nov. 2, 1999;131(9):696-701.
Baker et al., Oral infection with Porphyromonas gingivalis and induced alveolar bone loss in immunocompetent and severe combined immunodeficient mice. Arch Oral Biol. Dec. 1994;39(12):1035-40.
Baldwin et al., Amino Acid Synthesis via Ring Opening of N-Sulphonyl Aziridine-2-Carboxylate Esters with Organometallic Reagents. Tetrahedron. 1993;49:6309-30.
Bártová et al., Th1 and Th2 cytokine profile in patients with early onset periodontitis and their healthy siblings. Mediators Inflamm. 2000;9(2):115-20.
Beck et al., Dental Infections and Atherosclerosis. Am Heart J. 1999;13:528-33.
Beckett et al., Configurational Studies in Synthetic Analgesics: the Synthesis of (−)-Methadone from D-(−)- Alanine. J Chem Soc. 1957;1:858-61.
Beilman et al., Experimental brown spider bite in the guinea pig: Results of treatment with dapsone or hyperbaric oxygen. J Wilderness Medicine. 1994;5:287-94.
Belikov, Abbreviated Guide to Synthetic and Natural Medications. Pharmaceutical Chemistry. Higher School. 1993;1:43-47. Russian.
Beltrami et al., Some Methylhydrazonium Salts; An Improved Synthesis of Tetramethylhydrazine. J Am Chem Soc. 1956;78:2467-68.
Bernstein et al., Daily or weekly therapy with resiquimod (R-848) reduces genital recurrences in herpes simplex virus-infected guinea pigs during and after treatment. J Infect Dis. Mar. 15, 2001;183(6):844-9. Epub Feb. 13, 2001.
Bertino et al., Principles of Cancer Therapy. Cecil Textbook of Medicine. Goldman et al., eds. 21th Ed. W.B. Saunders Company. 2000:1:1060-74.
Beutler et al., Tumor necrosis factor in the pathogenesis of infectious diseases. Crit Care Med. Oct. 1993;21(10 Suppl):S423-35.
Beutner et al., Therapeutic response of basal cell carcinoma to the immune response modifier imiquimod 5% cream. J Am Acad Dermatol. Dec. 1999;41(6):1002-7.
Beutner et al., Treatment of genital warts with an immune-response modifier (imiquimod). J Am Acad Dermatol. Feb. 1998;38(2 Pt 1):230-9.
Binder, Acute arthropod envenomation. Incidence, clinical features and management. Med Toxicol Adverse Drug Exp. May-Jun. 1989;4(3):163-73.
Bishop et al., Molecular mechanisms of B lymphocyte activation by the immune response modifier R-848. J Immunol. Nov. 15, 2000;165(10):5552-7.

Bitterman-Deutsch et al., [Brown spider bite]. Harefuah. Sep. 1990;119(5-6):137-9. Hebrew.

Booth et al., Dapsone suppresses integrin-mediated neutrophil adherence function. J Invest Dermatol. Feb. 1992;98(2):135-40.

Borkan et al., An outbreak of venomous spider bites in a citrus grove. Am J Trop Med Hyg. Mar. 1995;52(3):228-30.

Bourke et al., The toll-like receptor repertoire of human B lymphocytes: inducible and selective expression of TLR9 and TLR10 in normal and transformed cells. Blood. Aug. 1, 2003;102(3):956-63. Epub Apr. 10, 2003.

Brants, The Distribution of Tobacco Mosaic Virus (TMV) in Excised Tomato Roots Cultivated in Vitro. Tijdschr Plantenziekten, 1962;68:198-207.

Brassard et al., Interferon-α as an immunotherapeutic protein. J Leukoc Biol. Apr. 2002;71(4):565-81.

Breathnach, Azelaic acid: potential as a general antitumoural agent. Med Hypotheses. Mar. 1999;52(3):221-6.

Broughton, Management of the brown recluse spider bite to the glans penis. Mil Med. Oct. 1996;161(10):627-9.

Buckle et al., 4-hydroxy-3-nitro-2-quinolones and related compounds as inhibitors of allergic reactions. J Med Chem. Jul. 1975;18(7):726-32.

Buisson et al., Preparation and use of (S)-O-acetyllactyl chloride (Mosandl's reagent) as a chiral derivatizing agent. Tetrahedron Assym. 1999;10:2997-3002.

Bulut et al., Cooperation of Toll-like receptor 2 and 6 for cellular activation by soluble tuberculosis factor and Borrelia burgdorferi outer surface protein A lipoprotein: role of Toll-interacting protein and IL-1 receptor signaling molecules in Toll-like receptor 2 signaling. J Immunol. Jul. 15, 2001;167(2):987-94.

Burleson, Chapter 14. Influenza Virus Host Resistance Model for Assessment of Immunostimulation, and Antiviral Compounds. Methods in Immunology. 1995;2:181-202.

Buschle et al., Interferon γ inhibits apoptotic cell death in B cell chronic lymphocytic leukemia. J Exp Med. Jan. 1, 1993;177(1):213-8.

Cai et al., Evaluation of trifluoroacetic acid as an ion-pair reagent in the separation of small ionizable molecules by reversed-phase liquid chromatography. Analytica Chmica Acta. 1999;399:249-258.

Cantell et al., IFN-γ Enhances Production of IFN-α in Human Macrophages but Not in Monocytes. J Interferon and Cytokine Res. 1996;16:461-63.

Carceller et al., Design, synthesis, and structure-activity relationship studies of novel 1-[(1-acyl-4-piperidyl)methyl]-1H-2-methylimidazo[4,5-c]pyridine derivatives as potent, orally active platelet-activating factor antagonists. J Med Chem. Jan. 19, 1996;39(2):487-93.

Carrigan et al., Synthesis and in vitro pharmacology of substituted quinoline-2,4-dicarboxylic acids as inhibitors of vesicular glutamate transport. J Med Chem. May 23, 2002;45(11):2260-76.

Catarzi et al., Tricyclic heteroaromatic systems. Pyrazolo[3,4-c]quinolin-4-ones and pyrazolo[3,4-c]quinoline-1,4-diones: synthesis and benzodiazepine receptor activity. Arch Pharm (Weinheim). Dec. 1997;330(12):383-6.

Cheson et al., National Cancer Institute-sponsored Working Group guidelines for chronic lymphocytic leukemia: revised guidelines for diagnosis and treatment. Blood. Jun. 15, 1996;87(12):4990-7.

Chuang et al., Toll-like receptor 9 mediates CpG-DNA signaling. J Leukoc Biol. Mar. 2002;71(3):538-44.

Claisen, [Uber α-Methyl-isoxazol.] Berichte. 1909;42:59-69. German.

Cohen et al., Cytokine function: a study in biologic diversity. Am J Clin Pathol. May 1996;105(5):589-98.

Cole et al., Brown recluse spider envenomation of the eyelid: an animal model. Ophthal Plast Reconstr Surg. Sep. 1995;11(3):153-64.

Colotta et al., Synthesis and structure-activity relationships of a new set of 2-arylpyrazolo[3,4-c]quinoline derivatives as adenosine receptor antagonists. J Med Chem. Aug. 10, 2000;43(16):3118-24.

Cristalli et al., Adenosine deaminase inhibitors: synthesis and structure-activity relationships of imidazole analogues of erythro-9-(2-hydroxy-3-nonyl)adenine. J Med Chem. Mar. 1991;34(3):1187-92.

Dai et al., Synthesis of a novel C2-symmetric thiourea and its application in the Pd-catalyzed cross-coupling reactions with arenediazonium salts under aerobic conditions. Org Lett. Jan. 22, 2004;6(2):221-4.

Davis, Current therapy for chronic hepatitis C. Gastroenterology. Feb. 2000;118(2 Suppl 1):S104-14.

Davis et al., Heterocyclic Syntheses with Malonyl Chloride. Part VI. 3-Substituted Pyridine Derivatives from α-Methylene-nitriles. J Chem Soc. 1962:3638-44.

Davis et al., Self-administered topical imiquimod treatment of vulvar intraepithelial neoplasia. A report of four cases. J Reprod Med. Aug. 2000;45(8):619-23.

De et al., Structure-activity relationships for antiplasmodial activity among 7-substituted 4-aminoquinolines. J Med Chem. Dec. 3, 1998;41(25)4918-26.

Debol et al., Anti-inflammatory action of dapsone: inhibition of neutrophil adherence is associated with inhibition of chemoattractant-induced signal transduction. J Leukoc Biol. Dec. 1997;62(6):827-36.

De Clerq, Synthetic interferon inducers. Top Curr Chem. 1974;52:173-208.

Decker et al., Immunostimulatory CpG-oligonucleotides cause proliferation, cytokine production, and an immunogenic phenotype in chronic lymphocytic leukemia B cells. Blood. Feb. 1, 2000;95(3):999-1006.

Decker et al., Immunostimulatory CpG-oligonucleotides induce functional high affinity IL-2 receptors on B-CLL cells: costimulation with IL-2 results in a highly immunogenic phenotype. Exp Hematol. May 2000;28(5):558-68.

Delgado, Textbook of Organic Medicinal and Pharmaceutical Chemistry, Ninth Edition, Remers, ed., 1991:30-1.

Denzel et al. Imidazo [4,5-c]- and [4,5-b]pyridines. J. Heterocyclic Chem. 1977;14:813-821.

Diaz-Arrastia et al., Clinical and molecular responses in high-grade intraepithelial neoplasia treated with topical imiquimod 5%. Clin Cancer Res. Oct. 2001;7(10):3031-3.

Di Carlo et al., Neutrophils in anti-cancer immunological strategies: old players in new games. J Hematother Stem Cell Res. Dec. 2001;10(6):739-48.

Dicken et al., Reactions at High Pressures. [3+2] Dipolar Cycloaddition of Nitrones with Vinyl Ethers. J Org Chem. 1982;47:2047-51.

Dockrell et al., Imiquimod and resiquimod as novel immunomodulators. J Antimicrob Chemother. Dec. 2001;48(6):751-5.

Dorwald, "Preface." Side Reactions in Organic Synthesis. A Guide to Successful Synthesis Design. Wiley-VCH. 2005: IX.

Douglas, Introduction to Viral Diseases. In: Cecil Textbook of Medicine. Bennet et al., eds. 20th Ed. W.B. Saunders Company. 1996:2:1739-47.

Doyle et al., Toll-like receptor 3 mediates a more potent antiviral response than Toll-like receptor 4. J Immunol. Apr. 1, 2003;170(7):3565-71.

Drexler et al., Bryostatin 1 induces differentiation of B-chronic lymphocytic leukemia cells. Blood. Oct. 1989;74(5):1747-57.

Dzionek et al. BDCA-2, BDCA-3, and BDCA-4: three markers for distinct subsets of dendritic cells in human peripheral blood. J Immunol. Dec. 1, 2000;165(11):6037-46.

Edwards et al., Toll-like receptor expression in murine DC subsets: lack of TLR7 expression by CD8 alpha+ DC correlates with unresponsiveness to imidazoquinolines. Eur J Immunol. Apr. 2003;33(4):827-33.

Eriks et al., Histamine H2-receptor agonists. Synthesis, in vitro pharmacology, and qualitative structure-activity relationships of substituted 4- and 5-(2-aminoethyl)thiazoles. J Med Chem. Aug. 21, 1992;35(17):3239-46.

Fecci et al., The history, evolution, and clinical use of dendritic cell-based immunization strategies in the therapy of brain tumors. J Neurooncol. Aug.-Sep. 2003;64(1-2):161-76.

Fitzgerald-Bocarsly et al., Virally-Responsive IFN-α Producing Cells in Human Blood and Tonsil Are CD11C/CD123+ Cells Identical to Precursors of Type Two Dendritic Cells (pDC2). J Interferon Cytokine Res. 1999;19(1):S117. Abstract P81.

Flo et al., Involvement of toll-like receptor (TLR) 2 and TLR4 in cell activation by mannuronic acid polymers. J Biol Chem. Sep. 20, 2000;277(38):35489-95. Epub Jun. 27, 2002.

Fonteneau et al., Human Immunodeficiency Virus Type 1 Activates Plasmacytoid Dendritic Cells and Concomitantly Induces the Bystander Maturation of Myeloid Dendritic Cells. J Virol. 2004;78(10):5223-32.

Frankel et al., The Preparation of N-Disubstituted Formamides. Tetrahedron Lett. 1959;7:5-7.

Frantz et al., Toll4 (TLR4) expression in cardiac myocytes in normal and failing myocardium. J Clin Invest. Aug. 1999;104(3):271-80.

Fu et al., Regioselective Catalytic Hydrogenation of Polycyclic Aromatic Hydocarbons under Mild conditions. J Org Chem. 1980;45:2979-803.

Fuchsberger et al., Priming Interferon-a 1 or Interferon-a 2 Enhances the Production of Both Subtypes Simultaneously. J Interferon and Cytokine Res. 1995;15:637-39.

Galose, Dapsone (diaminodiphenylsulphone DDS). Clinical Toxicology Review. 1999:21(9). 3 pages.

Gendron, Loxosceles ignali Envenomation. Am J Emerg Med. Jan. 1990;8(1):51-4.

Genevois-Borella et al., Synthesis of 1-(3-R-Amino-4-Hydroxy Butyl)thymine Acyclonucleoside. Analogs as Potential Anti-AIDS Drugs. Tetrahedron Lett. 1990;31:4879-82.

Giannini et al., Influence of the Mucosal Epithelium Microenvironment on Langerhans Cells: Implications for the Development of Squamous Intraepithelial Lesions of the Cervix. Int J Cancer. 2002;97:654-59.

Gibson et al., Cellular requirements for cytokine production in response to the immunomodulators imiquimod and S-27609. J Interferon Cytokine Res. Jun. 1995;15(6):537-45.

Gibson et al., Plasmacytoid dendritic cells produce cytokines and mature in response to the TLR7 agonists, imiquimod and resiquimod. Cell Immunol. Jul.-Aug. 2002;218(1-2):74-86.

Gitelson et al., Chronic lymphocytic leukemia-reactive T cells during disease progression and after autologous tumor cell vaccines. Clin Cancer Res. May 2003;9(5):1656-65.

Gomez et al., Intradermal anti-loxosceles Fab fragments attenuate dermonecrotic arachnidism. Acad Emerg Med. 1999;6:1195-202.

Gorden et al., Synthetic TLR agonists reveal functional differences between human TLR7 and TLR8. J Immunol. Feb. 1, 2005;174(3):1259-68.

Gordon, Pattern recognition receptors: doubling up for the innate immune response. Cell. Dec. 27, 2002;111(7):927-30.

Gunning et al., Chemoprevention by lipoxygenase and leukotriene pathway inhibitors of vinyl carbamate-induced lung tumors in mice. Cancer Res. Aug. 1, 2002;62(15):4199-201.

Gürsel et al., Differential and competitive activation of human immune cells by distinct classes of CpG oligodeoxynucleotide. J Leukoc Biol. May 2002;71(5):813-20.

Hart, Napthyridines Hydroxynaphthyridies, Journal of Chemical Society, 1956;Part III:212-4.

Hartmann et al., Rational design of new CpG oligonucleotides that combine B cell activation with high IFN-alpha induction in plasmacytoid dendritic cells. Eur J Immunol. Jun. 2003;33(6):1633-41.

Hayashi Toll-like receptors stimulate human neutrophil function. Blood. Oct. 1, 2003;102(7):2660-69. Epub Jun. 26, 2003.

Hayes et al., Regulation of Interferon Production by Human Monocytes: Requirements for Priming for Lipopolysaccharide-Induced Production. J Leukocyte Biol. 1991;50:176-81.

Heil et al., Species-specific recognition of single-stranded RNA via toll-like receptor 7 and 8. Science. Mar. 5, 2004;303(5663):1526-9. Epub Feb. 19, 2004.

Heil et al., Synthetic immunostimulatory compounds activate immune cells via TLR7 and TLR8. 33th Annual Meeting of the Deutsche Gessellschaft Mr Immunologie, Marburg 2002. Abstract C.6.

Hemmi et al., Small anti-viral compounds activate immune cells via the TLR7 MyD88-dependent signaling pathway. Nat Immunol. Feb. 2002;3(2):196-200. Epub Jan. 22, 2002.

Hobbs et al., Comparison of hyperbaric oxygen and dapsone therapy for loxosceles envenomation. Aced Emerg Med. Aug. 1996;3(8):758-61.

Hoffman et al., Conformational requirements for histamine H2-receptor inhibitors: a structure-activity study of phenylene analogues related to cimetidine and tiotidine. J Med Chem. Feb. 1983;26(2):140-4.

Hofmanová et al., Lipoxygenase inhibitors induce arrest of tumor cells in S-phase of the cell cycle. Neoplasma. 2002;49(6):362-7.

Holladay et al., Structure-activity studies related to ABT-594, a potent nonopioid analgesic agent: effect of pyridine and azetidine ring substitutions on nicotinic acetylcholine receptor binding affinity and analgesic activity in mice. Bioorg Med Chem Lett. Oct. 6, 1998;8(19):2797-802.

Horng et al., The adaptor molecule TIRAP provides signaling specificity for Toll-like receptors. Nature. Nov. 21, 2002;420(6913):329-33.

Hornung et al., Quantitative Expression of Toll-Like Receptor 1-10 mRNA in Cellular Subsets of Human Peripheral Blood Mononuclear Cells and Sensitivity to CpG Oligodeoxynucleotides. Journal of Immunol. 2002;168:4531-37.

Houben-Weyl, Quinoline and Isoquinoline. Methoden der Organischen Chemie. 1980:271-79. German.

Houston et al., Potential inhibitors of S-adenosylmethionine-dependent methyltransferases. 8. Molecular dissections of carbocyclic 3-deazaadenosine as inhibitors of S-adenosylhomocysteine hydrolase. J Med Chem. Apr. 1985;28(4):467-71.

Huppatz, Systemic fungicides. The synthesis of certain pyrazole analogues of carboxin. Aust J Chem. 1983;36:135-47.

Iino et al., Treatment of Chronic Hepatitis C With High-Dose Interferon α-2b. Multicenter Study. Dig Dis Sci. 1993;38(4):612-18.

Ito et al., Interferon-alpha and interleukin-12 are induced differentially by Toll-like receptor 7 ligands in human blood dendritic cell subsets. J Exp Med. Jun. 3, 2002;195(11):1507-12.

Iwashita et al., Syntheses of Isoretronecanol and Lupinine. J Org Chem. 1982;47:230-33.

Jacobs, Chapter 1. The Synthesis of Acetylenes. In: Organic Reactions. New York: Wiley & Sons, Inc., 1949. vol. 5. 1-78.

Jahnsen et al., Extensive recruitment of IL-3Rαhigh dendritic-cell precursors to allergic nasal mucosa during allergen challenge. Immunology Lett. 1999;69(1):123. Abstract #32.2.

Jurk et al. Human TLR7 and TLR8 independently confer responsiveness to the antiviral compound R-848. Nat Immunol. Jun. 2002;3(6):499.

Juweid, Radioimmunotherapy of B-Cell Non-Hodgkin's Lymphoma: From Clinical Trials to Clinical Practice. J Nuclear Med. 2002;43(11):1507-29.

Katritsky et at., Comprehensive Heterocyclic Chemistry: The Structure, Reactions, Synthesis and Uses of Heterocyclic Compounds. 1984;2:586-587.

Keating et al., Long-term follow-up of patients with chronic lymphocytic leukemia treated with fludarabine as a single agent. Blood. Jun. 1, 1993;81(11):2878-84.

Klausen et al., Two complementary methods of assessing periodontal bone level in rats. Scand J Dent Res. Dec. 1989;97(6):494-9.

Klinman, Immunotherapeutic uses of CpG oligodeoxynucleotides. Nat Rev Immunol. Apr. 2004;4(4):249-58.

Kloek et al., An improved method for the synthesis of stabilized primary enamines and imines. J Org Chem. 1978;43:1460-62.

Kloetzel, Reactions of nitroparaffins. I. Synthesis and reduction of some ò-nitrokenes. J Am Chem Soc. 1947;69:2271-2275.

Kornman, Host modulation as a therapeutic strategy in the treatment of periodontal disease. Clin Infect Dis. Mar. 1999;28(3):520-6.

Kourafalos et al., Synthesis of 7-aminopyrazolo[3,4-c]pyridine as a probe for the preparation of compounds of pharmacological interest. Heterocycles. 2002;57(12):2335-2343.

Krause et al., Autoimmune aspects of cytokine and anticytokine therapies. Am J Med. Oct. 1, 2003;115(5):390-7.

Krenitsky et al., Imidazo[4,5-c]pyridines (3-deazapurines) and their nucleosides as immunosuppressive and anti-inflammatory agents. J Med Chem. Jan. 1986;29(1):138-43.

Kurt-Jones et al., Role of toll-like receptor 2 (TLR2) in neutrophil activation: GM-CSF enhances TLR2 expression and TLR2-mediated interleukin 8 responses in neutrophils. Blood. Sep. 1, 2002;100(5):1860-8.

Lall et al., Serine and threonine beta-lactones: a new class of hepatitis A virus 3C cysteine proteinase inhibitors. J Org Chem. Mar. 8, 2002;67(5):1536-47.

Lee et al., p38 mitogen-activated protein kinase inhibitors—mechanisms and therapeutic potentials. Pharmacol Ther. 1999;82:389-97.

Lee et al., Saturated fatty acid activates but polyunsaturated fatty acid inhibits Toll-like receptor 2 dimerized with Toll-like receptor 6 or 1. J Biol Chem. Apr. 23, 2004;279(17):16971-9. Epub Feb. 13, 2004.

Lehner et al., The role of γδ cells and β-chemokines in mucosal protection against SIV infection. Immunology Lett. 1999;69:25-192. Abstract 2.1.

Levy et al., Unique efficacy of Toll-like receptor 8 agonists in activating human neonatal antigen-presenting cells. Blood. Aug. 15, 2006;108(4):1284-90. Epub Apr. 25, 2006.

Leynadier et al., Allergic reactions to North African scorpion venom evaluated by skin test and specific IgE. J Allergy Clin Immunol. Jun. 1997;99(6 Pt 1):851-3. 4 pages.

Li et al., An improved protocol for the preparation of 3-pyridyl- and some arylboronic acids. J Org Chem. Jul. 26, 2002;67(15):5394-7.

Li et al., Solubility behavior of imiquimod in alkanoic acids. Pharmaceutical Research. 1997 American Association of Pharmaceutical Scientists Annual Meeting. Poster Presentation, Boston, MA, Nov. 2-6, 1997;S475:Abstract 3029.

Li et al., Synthesis, CoMFA analysis, and receptor docking of 3,5-diacyl-2, 4-dialkylpyridine derivatives as selective A3 adenosine receptor antagonists. J Med Chem. Feb. 25, 1999;42(4):706-21.

Litt et al., Mucosal delivery of vaccine antigens displayed on the surface of Lactococcus lactis. Immunology Lett. 1999;69(1):61. Abstract #11.26.

Liu et al., Synthesis of halogen-substituted 3-deazaadenosine and 3-deazaguanosine analogues as potential antitumor/antiviral agents. Nucleosides Nucleotides Nucleic Acids. Dec. 2001;20(12):1975-2000.

Loesche et al., Treatment paradigms in periodontal disease. Compend Contin Educ Dent. Mar. 1997;18(3):221-6, 228-30, 232 passim; quiz 234. Review.

Luger et al., Evidence for an epidermal cytokine network. J Invest Dermatol. Dec. 1990;95(6 Suppl):100S-104S.

Luskin et al., Olefinic Derivatives of 2,4-Diamino-s-triazines. J Org Chem. 1958;23:1032-37.

Macchia et al., Synthesis and antiviral properties of 9-[(2-methyleneaminoxyethoxy)methyl]guanine derivatives as novel Acyclovir analogues. Farmaco. Feb. 2000;55(2):104-8.

Majeski et al., Action of venom from the brown recluse spider (Loxosceles reclusa) on human neutrophils. Toxicon. 1977;15(5):423-7.

Makarenkova et al., Identification of delta- and mu- type opioid receptors on human and murine dendritic cells. J Neuroimmunol. 2001;117:68-77.

Male et al., Introduction to the Immune System. In: Immunology. Elsevier. 2006:6-7.

Masihi, Progress on novel immunomodulatory agents for HIV-1 infection and other infectious diseases. Expert Opin Ther Patents. 2003;13(6):867-82.

Masiukiewicz et al., Scalable Syntheses of $N^\alpha$-Benzyloxycarbonyl-$_L$-Ornithine and of $N^\alpha$-(9-Fluorenylmethoxy)Carbonyl-$_L$-Ornithine. Org Prep Proced Int. 2002;34:531-37.

Mataka et al., Condensation reaction of 3,4-Dibenzoyl-1-methyl-2,5-diphenylpyrrole and -1-phenylpyrazole with methylamine derivatives affording pyrrolo [3,4-c] pyridine and 2H-pyrazolo[3,4-c]- and [4,3-c]pyridines. Journal of Heterocyclic Chemistry. 1981;18(6):1073-5.

Mathur et al., Cell-mediated immune system regulation in periodontal diseases. Crit Rev Oral Biol Med. 1997;8(1):76-89.

Maynor et al., Brown recluse spider envenomation: a prospective trial of hyperbaric oxygen therapy. Acad Emerg Med. Mar. 1997;4(3):184-92.

Mbow et al., Small molecule and biologic modulators of the immune response to hepatitis C virus. Mini Rev Med Chem. May 2006;6(5):527-31.

McCarthy et al., Opioids, opioid receptors, and the immune response. Drug & Alcohol Dependence. 2001;62:111-23.

McKennon et al., A Convenient Reduction of Amino Acids and Their Derivatives. J Org Chem. 1993;58:3568-71.

McLaughlin et al., Opioid growth factor (OGF) inhibits the progression of human squamous cell carcinoma of the head and neck transplanted into nude mice. Cancer Lett. 2003;199:209-17.

Medzhitov, Toll-Like Receptors and Innate Immunity. Nature Rev Immunol. 2001;1:135-45.

Mee et al., Stille coupling made easier—the synergic effect of copper(I) salts and the fluoride ion. Angew Chem. 2004;116:1152-56.

Merigian et al., Envenomation From the Brown Recluse Spider: Review of Mechanism and Treatment Options. Am J Ther. Oct. 1996;3(10):724-734.

Miller et al., Imiquimod applied topically: a novel immune response modifier and new class of drug. Int J Immunopharmacol. Jan. 1999;21(1):1-14.

Minakawa et al., Nucleosides and Nucleotides. 184. Synthesis and Conformational Investigation of Anti-Fixed 3-Deaza-3-halopurine Ribonucleosides. J Org Chem. 1999;64:7158-72.

Moebius et al., The mysteries of sigma receptors: new family members reveal a role in cholesterol synthesis. Trends Pharmacol Sci. Mar. 1997;18(3):67-70.

Moldoveanu et al., Poly-L-lysine as a potential mucosal adjuvant. Immunology Lett. 1999;69(1):62. Abstract #11.28.

Mollick et al., MUC1-like tandem repeat proteins are broadly immunogenic in cancer patients. Cancer Immun. Mar. 17, 2003;3:3. 17 pages.

Moody et al., Lipoxygenase inhibitors prevent lung carcinogenesis and inhibit non-small cell lung cancer growth. Exp Lung Res. Jul.-Aug. 1998;24(4):617-28.

Moraczewski et al., Using Hydrogen Bonding to Control Carbamate C-N Rotamer Equilibria. Org Chem. Oct. 16, 1998;63(21):7258-7262.

Mosbech et al., [Allergy to insect stings] Ugeskr Laeger. Oct. 28, 1991;153(44):3067-71. Danish.

Muche et al., Imiquimod treatment of cutaneous T cell lymphoma. Journal of Investigative Dermatology. Jul. 2003;121(1):0975. Joint Meeting of the European Society for Dermatologi; Miami Beach, Florida, USA. Apr. 30-May 4, 2003. Abstract 0975.

Muller et al., An improved one-pot procedure for the synthesis of alkynes from aldehydes. Synlett. 1996;6:521-522.

Mutschler et al., 9.2 Anti-infectives. In: Drug Actions: Basic Principles and Therapeutic Aspects. 1995:515-80.

Muzio et al., Differential expression and regulation of toll-like receptors (TLR) in human leukocytes: selective expression of TLR3 in dendritic cells. J Immunol. Jun. 1, 2000;164(11):5998-6004.

Nagarajan et al., Condensed heterotricycles: synthesis of pyrazolo[3,4-c]quinoline derivatives. Indian Journal of Chemistry. 1992;31B:316-321.

Nagase et al., Expression and function of Toll-like receptors in eosinophils: activation by Toll-like receptor 7 ligand. J Immunol. Oct. 15, 2003;171(8):3977-82.

Nanjappan et al., An efficient synthesis of some 6-substituted 4,8-diaza-3,3,9,9-tetramethylundeca-2,10-dione dioximes (propylene amine oximes, PnAOs): Ligands for 99mTc complexes used in structure distribution relationship (SDR) studies. Tetrahedron. 1994;50(29):8617-32.

Ohana et al., Differential effect of adenosine on tumor and normal cell growth: focus on the A3 adenosine receptor. Journal of Cellular Physiology. Jan. 2001;186(1):19-23. Review.

O'Mahony et al., New patient-applied therapy for anogenital warts is rated favourably by patients. Intl J STD & AIDS. 2001;12:565-70.

Osol et al., Chapter 27: Structure-Activtiy Relationship and Drug Design. In: Remington's Pharmaceutical Sciences. 16th Ed. Mach Publishing. 1980:420-35.

Ottonello et al., Sulphonamides as anti-inflammatory agents: old drugs for new therapeutic strategies in neutrophilic inflammation? Clin Sci (Lond). Mar. 1995;88(3):331-6.

Ozinsky et al., The repertoire for pattern recognition of pathogens by the innate immune system is defined by cooperation between Toll-like receptors. Proc. Nat. Acad. Sci. 2000; 97(25):13766-71.

Page et al., Advances in the pathogenesis of periodontitis: summary of developments, clinical implications and future directions. Periodontol 2000. Jun. 1997;14:216-48.

Park et al., Immunotherapy Cancer Treatment. Reprinted from Supportive Cancer Care, Rosenbaum et al. 2001. Available at http://www.cancersupportivecare.com/immunotherapy.html. Last accessed Jul. 13, 2010. 3 pages.

Park et al., Sodium Dithionite Reduction of Nitroarenes Using Viologen as an Electron Phase-Transfer Catalyst. Tetrahedron Lett. 1993;34(46):7445-46.

Patel et al., The necrotic venom of the brown recluse spider induces dysregulated endothelial cell-dependent neutrophil activation. Differential induction of GM-CSF, IL-8, and E-selectin expression. J Clin Invest. Aug. 1994;94(2):631-42.

Patrick et al., Paragraph 10.3: Drug optimization: strategies in drug design. In: An Introduction to Medicinal Chemistry. Oxford: Oxford University Press. Jan. 2005. 200-218.

Pavletic et al., Outcome of allogeneic stem cell transplantation for B cell chronic lymphocytic leukemia. Bone Marrow Transplant. Apr. 2000;25(7):717-22.

Pawlas et al., Novel anionic annelation tactics for construction of fused heteroaromatic frameworks. 1. Synthesis of 4-substituted pyrazolo[3,4-c]quinolines, 9-substituted pyrazolo[3,4-c]quinolines, and 1,4-dihydrochromeno[4,3-c]pyrazoles. Org Chem. Jun. 15, 2001;66(12):4214-9.

Payvandi et al., Exogenous and Endogenous IL-10 Regulate IFN-α Production by Peripheral Blood Mononuclear Cells in Response to Viral Stimulation. J Immunol. 1998;160:5861-68.

Peschke et al., Synthesis and in vitro characterization of new growth hormone secretagogues derived from ipamorelin with dipeptidomimetic N-terminals. Eur J Med Chem. 1999;34:363-380.

Peterson et al., The opioid-cytokine connection. J Neuroimmunol. 1998;83:63-69.

Phillips et al., Therapy of brown spider envenomation: a controlled trial of hyperbaric oxygen, dapsone, and cyproheptadine. Ann Emerg Med. Mar. 1995;25(3):363-8.

Pickersgill et al., Preparation of functionalized, conformationally constrained DTPA analogues from L- or D-serine and trans-4-hydroxy-L-proline. Hydroxymethyl substituents on the central acetic acid and on the backbone. J Org Chem. Jun. 30, 2000;65(13):4048-57.

Poljakovic et al., iNOS and COX-2 immunoreactivity in the mice bladder and kidney after bacterial instillation. Immunology Lett. 1999;69(1):122. Abstract #31.5.

Powell et al., Compendium of excipients for parenteral formulations. PDA J Pharm Sci Technol. Sep.-Oct. 1998;52(5):238-311.

Prelog et al., Cycloalkeno-pyridine. Helv Chem Acta. 1945;28:1684-93. German.

Rees et al., Brown recluse spider bites. A comparison of early surgical excision versus dapsone and delayed surgical excision. Ann Surg. Nov. 1985;202(5):659-63.

Regan et al., Activation of p38 MAPK by feline infectious peritonitis virus regulates pro-inflammatory cytokine production in primary blood-derived feline mononuclear cells. Virology. Feb. 5, 2009;384(1):135-43. Epub Dec. 5, 2008.

Rhodes, Discovery of immunopotentiatory drugs: current and future strategies. Clin Exp Immunol. Dec. 2002;130(3):363-9.

Ribera et al., "Spontaneous" complete remissions in chronic lymphocytic leukemia: report of three cases and review of the literature. Blood Cells. 1987;12(2):471-79.

Ritter et al., A new reaction of nitriles; amides from alkenes and mononitriles. J Am Chem Soc. Dec. 1948;70(12):4045-8.

Rocca et al., Carbolines. Part VII. Ansidines, Convenient tools to synthesize fficien-β-carbolines. J Heterocyclic Chem. 1995;32:1171-1175.

Rocca et al., Connection between metalation and cross-coupling strategies. A new convergent route to azacarbazoles. Tetrahedron. 1993;49(1):49-64.

Rollins, Chemokines. Blood. Aug. 1, 1997;90(3):909-28. Review.

Rosenberg et al., Treatment of 283 consecutive patients with metastatic melanoma or renal cell cancer using high-dose bolus interleukin 2. JAMA. Mar. 23-30, 1994;271(12):907-13.

Rothel et al., The use of recombinant ovine IL-1beta and TNF-alpha as natural adjuvants and their physiological effects in vivo. Immunol Cell Biol. Apr. 1998;76(2):167-72.

Roy et al., QSAR of adenosine receptor antagonists II: exploring physicochemical requirements for selective binding of 2-arlypyrazolo[3,4-c] quinoline derivatives with adenosine A1 and A3 receptor subtypes. QSAR & Comb Sci. 2003;22:614-621.

Royals et al., Studies in mixed ester condensations. IV. Acylations with methyl dimethoxyacetate. J Am Chem Soc. 1956;78:4161-4164.

Rozman et al., Chronic lymphocytic leukemia. N Engl J Med. Oct. 19, 1995;333(16):1052-7.

Sakthivel et al. Direct SnAr amination of fluorinated imizazo[4,5-c]pyridine nucleosides: efficient synthesis of 3-fluoro-3-3-deazaadenosine analogs. Tetrahedron Letters. May 2005;46(22):3883-3887.

Salaun et al., TLR3 Can Directly Trigger Apoptosis in Human Cancer Cells. J of Immunology. 2006;176:4894-901.

Salemink, Uber 2-Propyl-1- Und 2-Propyl-Desaza-Adenin. Recueil. 1961;80:545-55. German.

Sambhi et al., Local production of tumor necrosis factor encoded by recombinant vaccinia virus is effective in controlling viral replication in vivo. Proc Natl Acad Sci U S A. May 1, 1991;88(9):4025-9.

Sams et al., Necrotic arachnidism. J Am Acad Dermatol. Apr. 2001;44(4):561-73; quiz 573-6.

Sauder et al., Randomized, Single-Blind, Placebo-Controlled Study of Topical Application of the Immune Response Modulator Resiquimod in Healthy Adults. Antimicrobial Agents Chemo. 2003;47(12):3846-52.

Scheerlinck, Genetic adjuvants for DNA vaccines. Vaccine. Mar. 21, 2001;19(17-19):2647-56.

Scheuer et al., Application of the Ritter reaction to mesityl oxide and chalcone. J Am Chem Soc. 1957;22:674-676.

Schofield et al., Reply. Low-Dose Interferon-alpha in Chronic Myeloid Leukemia. Ann Internal Med. 1995;122(9):728-29. 1 page.

Schwandner et al., Peptidoglycan- and lipoteichoic acid-induced cell activation is mediated by toll-like receptor 2. J Biol Chem. Jun. 18, 1999;274(25):17406-9.

Seeman et al., Steric and Conformational Effects in Nicotine Chemistry. J Org Chem. 1981;46:3040-48.

Serrat et al., A highly efficient and straightforward stereoselective synthesis of novel chiral α-acetylenic ketones. Tetrahedron: Assymmetry. 1999;10:3417-30.

Seymour et al., Cellular immunity and hypersensitivity as components of periodontal destruction. Oral Dis. Mar. 1996;2(1):96-101. Review.

Severa et al., Sensitization to TLR7 agonist in IFN-beta-preactivated dendritic cells. J Immunol. May 15, 2007;178(10):6208-16.

Shelburne et al., Quantitation of Bacteroids forsythus in subgingival plaque comparison on immunoassay and quantitative polymerase chain reaction. J Microbiol Methods. 2000;39:97-107.

Sidky et al., Inhibition of murine tumor growth by an interferon-inducing imidazoquinolinamine. Cancer Res. Jul. 1, 1992;52(13):3528-33.

Siegal et al., The nature of the principal type 1 interferon-producing cells in human blood. Science. Jun. 11, 1999;284(5421):1835-7.

Sletzinger et al., The Synthesis of Isomethadone. J Am Chem Soc. 1952;74:5619-20.

Smith et al., The role of polymorphonuclear leukocytes in the lesion caused by the venom of the brown spider, Loxosceles reclusa. Lab Invest. Jan. 1970;22(1):90-3.

Sofina et al., C: Possibility of Predicting the Spectrum of Antitumor Effect of Drugs on the Basis of Experimental Data. Experimental evaluation of antitumor drugs in the USA and USSR and clinical correlations. NCI Monograph 55. NIH Publication No. 80-1933. 1980:76-8.

Sommer et al., Recent Findings on How Proinflammatory Cytokines Cause Pain: Peripheral Mechanisms in Inflammatory and Neuropathic Hyperalgesia. Neurosci Letts. 2004;361:184-87.

Sonogashira et al., A convenient synthesis of acetylenes: catalytic substitutions of acetylenic hydrogen with bromoalkenes, Iodoarenes, and bromopyridines. Tetrahedron Letts. 1975;50:4467-4470.

Soria et al., Effect of food on the pharmacokinetics and bioavailability of oral imiquimod relative to a subcutaneous dose. Int J Clin Pharmacol Ther. Oct. 2000;38(10):476-81.

Spaner et al., A phase I/II trial of TLR-7 agonist immunotherapy in chronic lymphocytic leukemia. Leukemia. 2010; 24:222-26.

Spaner et al., Immunomodulatory effects of Toll-like receptor-7 activation on chronic lymphocytic leukemia cells. Leukemia. Feb. 2006;20(2):286-95.

Spaner et al., Toll-like receptor agonists in the treatment of chronic lymphocytic leukemia. Leukemia. Jan. 2007;21(1):53-60. Epub Oct. 26, 2006.

Spivey et al., Configurationally stable biaryl analogues of 4-(dimethylamino)pyridine: A novel class of chiral nucleophilic catalysts. J Org Chem. 1999;64:9430-9443.

Spruance et al., Application of a topical immune response modifier, resiquimod gel, to modify the recurrence rate of recurrent genital herpes: a pilot study. J Infect Dis. Jul. 15, 2001;184(2):196-200. Epub Jun. 8, 2001.

Stack, Images in clinical medicine. Latrodectus mactans. N Engl J Med. Jun. 5, 1997;336(23):1649.

Stanley, Imiquimod and the imidazoquinolones: mechanism of action and therapeutic potential. Clin Exp Dermatol. Oct. 2002;27(7):571-7. Review.

Stashenko et al., Periapical inflammatory responses and their modulation. Crit Rev Oral Biol Med. 1998;9(4):498-521.

Steele et al., Lipoxygenase inhibitors as potential cancer chemopreventives. Cancer Epidemiol Biomarkers Prev. May 1999;8(5):467-83.

Steele et al., Potential use of lipoxygenase inhibitors for cancer chemoprevention. Expert Opin Investig Drugs. Sep. 2000;9(9):2121-38.

Steinmann et al., Topical imiquimod treatment of a cutaneous melanoma metastasis. J Am Aced Dermatol. Sep. 2000;43(3):555-6.

Stewart et al., Synthesis of a Carba-analog of S-Acetyl Coenzyme A, Acetonyl-dethio Coenzyme A; an Effective Inhibitor of Citrate Synthase. Liebigs Ann Chem. 1978:57-65.

Stillings et al., Substituted 1,3,4-thiadiazoles with anticonvulsant activity. 2. Aminoalkyl derivatives. J Med Chem. Nov. 1986;29(11):2280-4.

Strandtmann et al., Reaction of cyclic β-diketones with 3,4-dihydroisoquinolines and related compounds. Preparation and anticancer activity of 2-substituted 1,3-cyclohexanediones. J Med Chem. Nov. 1967;10(6):1063-5.

Stringfellow, Induction of interferon with low molecular weight compounds: fluorenone esters, ethers (tilorone), and pyrimidinones. Methods Enzymol. 1981;78(Pt A):262-84.

Ströher et al., Progress towards the treatment of Ebola haemorrhagic fever. Expert Opin Investig Drugs. Dec. 2006;15(12):1523-35.

Sugisaka et al., The Physicochemical properties of imiquimod, the first imidazoquinoline immune response modifier. Pharmaceutical Research. 1997 American Association of Pharmaceutical Scientists Annual Meeting. Poster Presentation, Boston, MA, Nov. 2-6, 1997;S475. Abstract 3030.

Surrey et al., The Synthesis of Some 3-Nitro- and 3-Amino-4-dialkylaminoalkylaminoquinoline Derivatives. J Am Chem Soc. 1951;73:2413-16.

Takeichi et al., Cytokine profiles of T-lymphocytes from gingival tissues with pathological pocketing. J Dent Res. Aug. 2000;79(8):1548-55.

Takeshita et al., Signal transduction pathways mediated by the interaction of CpG DNA with Toll-like receptor 9. Semin Immunol. Feb. 2004;16(1):17-22.

Takeuchi et al., Discrimination of bacterial lipoproteins by Toll-like receptor 6. Int Immunol. Jul. 2001;13(7):933-40.

Temple, Antimitotic agents: synthesis of imidazo[4,5-c]pyridin-6-ylcarbamates and imidazo[4,5-b]pyridin-5-ylcarbamates. J Med Chem. Feb. 1990;33(2):656-61.

Temple et al., Potential anticancer agents: 5-(N-substituted-aminocarbonyl)- and 5-(N-substituted-aminothiocarbonyl)-5,6,7,8-tetrahydrofolic acids. J Med Chem. Mar. 1988;31(3):697-700.

Thesing et al., [Darstellung and Eigenschaften des $\Delta^1$-Pyrrolin-$N$-oxyds.]. Chem Ber. 1959;92:1748-55. German.

Thiruvikraman et al., Synthesis and reactions of pyrazolo-[3,4-c]quinoline derivatives. Indian Journal of Chemistry. 1987;26B:695-696.

Tomai et al., Imiquimod: in vivo and in vitro characteristics and toxicology. In: Cutaneous Infection and Therapy. Aly et al., eds. Marcel Dekkar, Inc., New York. 1997:405-15.

Tomic et al., Sensitization of IL-2 Signaling through TLR-7 Enhances B Lymphoma Cell Immunogenicity. J Immunol. 2006;176:3830-39.

Tomioka et al., Asymmetric Alkylation of α-Alkyl β-Keto Esters. J Am Chem Soc. 1984;106:2718-19.

Totterman et al., Phorbol ester-induced differentiation of chronic lymphocytic leukaemia cells. Nature. Nov. 13, 1980;288(5787):176-8.

Tracy et al., Studies in the Pyridine Series. II. Synthesis of 2-Methyl-3-(β-Hydroxyethyl)pyridine and of the Pyridine Analog of Thiamine (Vitamin B2). J Org Chem. 1941;6:54-62.

Uno et al., TNF-related apoptosis-inducing ligand (TRAIL) frequently induces apoptosis in Philadelphia chromosome-positive leukemia cells. Blood. May 1, 2003;101(9):3658-67. Epub Dec. 27, 2002.

Urosevic et al., Imiquimod treatment induces expression of opioid growth factor receptor: a novel tumor antigen induced by interferon-alpha? Clin Cancer Res. Aug. 1, 2004;10(15):4959-70.

Van De Kerhof, New Immunomodulatory Drugs. In: Skin and Environment: Perception and Protection. Ring et al., eds., 10th EADV Congress, Oct. 10-14, Munich, Germany. 2001:1:343-48.

Vasilakos et al., Adjuvant Activities of Immune Response Modifier R-848: Comparison with CoG ODN. Cell Immunol. 2000;204:64-74.

Vieweg et al., Tumor vaccines: from gene therapy to dendritic cells-the emerging frontier. Urol Clin North Am. Aug. 2003;30(3):633-43.

Vilcek, The cytokines: An overview. In: The Cytokine Handbook, Fourth Ed. M. Lotze and A.W. Thompson (eds.), 2003;1:3-14.

Volhardt, 18-5. Amides: The Least-Reactive Carboxylic Acid Derivatives. Organic Chemistry. 1987:813.

Vollmer et al., Highly immunostimulatory CpG-free oligodeoxynucleotides for activation of human leukocytes. Antisense Nucleic Acid Drug Dev. Jun. 2002;12(3):165-75.

Wagner et al., Induction of cytokines in cynomolgus monkeys by the immune response modifiers, imiquimod, S-27609 and S-28463. Cytokine. Nov. 1997;9(11):837-45.

Wagner et al., Modulation of TH1 and TH2 Cytokine Production with the Immune Response Modifiers, R-848 and Imiguimod. Cellular Immunology. 1999;191:10-19.

Wang, Structure and Chemistry of 4-Hydroxy-6-methyl-2-pyridone. J Heterocyclic Chem. 1970;7:389-92.

Warren et al., Macrophage Growth Factor CSF-1 Stimulates Human Monocyte Production of Interferon, Tumor Necrosis Factor, and Colony Stimulating Activity. J Immunol. 1986;137(7):2281-85.

Wasserman et al., Loxoscelism and necrotic arachnidism. J Toxicol Clin Toxicol. 1983-1984;21(4-5):451-72.

Wedlock et al., Physiological effects and adjuvanticity of recombinant brushtail possum TNF-alpha. Immunol Cell Biol. Feb. 1999;77(1):28-33.

Wells, Additivity of Mutational Effects in Proteins. Biochemistry. 1990;29(37):8509-17.

Wermuth, Molecular Variations Based on Isosteric Replacements. Practice of Medicinal Chemistry.1996: 203-37.

Wexler et al., Accurate identification of experimental pulmonary metastases. J Natl Cancer Inst. Apr. 1966;36(4):641-5.

Wibaut et al., Syntheses of 3,4-Dimethylpyridine, 2,3-Dimethylpridine and 2-Methyl-3-Ethylpyridine. Rec Trav Chim. 1944;63:231-38.

Wierda et al., CD40-ligand (CD154) gene therapy for chronic lymphocytic leukemia. Blood. Nov. 1, 2000;96(9):2917-24.

Wieseler-Frank et al., Central proinflammatory cytokines and pain enhancement. Neurosignals. 2005;14(4):166-74.

Williams et al., Grignard Reactions to Chiral Oxazolidine Aldehydes. Tetrahedron. 1996;52:11673-94.

Wilson et al., Spiders and spider bites. Dermatol Clin. Apr. 1990;8(2):277-86.

Wright et al., Clinical presentation and outcome of brown recluse spider bite. Ann Emerg Med. Jul. 1997;30(1):28-32.

Wu et al., Murine B16 melanoma vaccination-induced tumor immunity: identification of specific immune cells and functions involved. J Interferon Cytokine Res. Dec. 2001;21(12):1117-27.

Yamamoto et al., Essential role for TIRAP in activation of the signalling cascade shared by TLR2 and TLR4. Nature. Nov. 21, 2002;420(6913):324-9.

Yeung-Yue et al., The management of herpes simplex virus infections. Curr Opin Infect Dis. Apr. 2002;15(2):115-22.

Yutilov et al., Synthesis and some reactions of 4-nitroimidazo[4-5-c]pyridin-2-ones. CAPLUS English Abstract DN 91:175261. VINITI.1978:1193-78. Abstract Only.

Zagon et al., Immunoelectron microscopic localization of the opioid growth factor receptor (OGFr) and OGF in the cornea. Brain Res. 2003;967:37-47.

Zagon et al., Opioids and the apoptotic pathway in human cancer cells. Neuropeptides. 2003;37:79-88.

Zagon et al., The biology of the opioid growth factor receptor (OGFr). Brain Res Rev. Feb. 2002;38(3):351-76. Review.

Zagon et al., The expression and function of the OGF-OGFr axis—a tonically active negative regulator of growth—in COS cells. Neuropeptides. Oct. 2003;37(5):290-7.

Zambon, Periodontal diseases: microbial factors. Ann Periodontol. Nov. 1996;1(1):879-925.

Zarubin et al., Theoretical Study of Antagonists and Inhibitors of Mammalian Adenosine Deaminase: I. Adenosine and Its Aza- and Deazaanalogues. Russ J Bioorg Chem. 2002;28(4):284-92.

Zhang et al., Structural features of azidopyridinyl neonicotinoid probes conferring high affinity and selectivity for mammalian alpha4beta2 and *Drosophila* nicotinic receptors. J Med Chem. Jun. 20, 2002;45(13):2832-40.

Zhu et al., Inhibition of murine dendritic cell activation by synthetic phosphorothioate oligodeoxynucleotides. J Leukoc Biol. Dec. 2002;72(6):1154-63.

Zhu et al., Inhibition of murine macrophage nitric oxide production by synthetic oligonucleotides. J Leukoc Biol. Apr. 2002;71(4):686-94.

Ziegler-Heitbrock et al., Favorable response of early stage B CLL patients to treatment with IFN-alpha 2. Blood. May 1, 1989;73(6):1426-30.

Zyryanov et al., Heterocyclization of 1-(2'-Carbethoxyphenyl)-5-Methyltetrazole. Chemistry of Heterocylic Compounds. English Edition. 1981;16(12):1286-88.

* cited by examiner

ARYLOXY AND ARYLALKYLENEOXY SUBSTITUTED THIAZOLOQUINOLINES AND THIAZOLONAPHTHYRIDINES

RELATED APPLICATIONS

This application is the National Stage of International Application No. PCT/US2005/021426, filed Jun. 17, 2005, which claims priority to U.S. Provisional Application Ser. No. 60/581,297, filed Jun. 18, 2004, which is incorporated herein by reference.

BACKGROUND OF THE INVENTION

In the 1950's the 1H-imidazo[4,5-c]quinoline ring system was developed, and 1-(6-methoxy-8-quinolinyl)-2-methyl-1H-imidazo[4,5-c]quinoline was synthesized for possible use as an antimalarial agent. Subsequently, syntheses of various substituted 1H-imidazo[4,5-c]quinolines were reported. For example, 1-[2-(4-piperidyl)ethyl]-1H-imidazo[4,5-c]quinoline was synthesized as a possible anticonvulsant and cardiovascular agent. Also, several 2-oxoimidazo[4,5-c]quinolines have been reported.

Certain 1H-imidazo[4,5-c]quinolin-4-amines and 1- and 2-substituted derivatives thereof were later found to be useful as antiviral agents, bronchodilators and immunomodulators. Subsequently, certain substituted 1H-imidazo[4,5-c]pyridin-4-amine, quinolin-4-amine, tetrahydroquinolin-4-amine, naphthyridin-4-amine, and tetrahydronaphthyridin-4-amine compounds as well as certain analogous thiazolo and oxazolo compounds were synthesized and found to be useful as immune response modifiers, rendering them useful in the treatment of a variety of disorders.

But despite important progress in the effort to find immunomodulating compounds, there is still a critical scientific and medical need for additional compounds that have an ability to modulate aspects of the immune response, by induction of cytokine biosynthesis or other mechanisms.

SUMMARY OF THE INVENTION

The present invention provides a new class of compounds that are useful in modulating cytokine biosynthesis in animals. In one aspect, the present invention provides compounds of the Formula I:

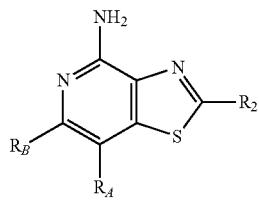

wherein:
$R_A$ and $R_B$ taken together form a fused benzene ring or fused pyridine ring wherein the benzene ring or pyridine ring is substituted by one $R_3$ group, or substituted by one $R_3$ group and one R group; and
$R_3$ is selected from the group consisting of:
—O—Z—Ar,
—O—Z—Ar'—Y—$R_4$,
—O—Z—Ar'—X—Y—$R_4$,
—O—Z—Ar'—$R_5$, and wherein R, $R_2$, Z, Ar, Ar', X, Y, $R_4$, and $R_5$ are as defined below;
and pharmaceutically acceptable salts thereof.

The compounds of Formula I are useful, for example, as immune response modifiers (IRMs) due to their ability to modulate cytokine biosynthesis (e.g., induce or inhibit the biosynthesis or production of one or more cytokines) and otherwise modulate the immune response when administered to animals. Compounds can be tested, for example, using the test procedures described in the Examples Section. Compounds can be tested for induction of cytokine biosynthesis by incubating human PBMC in a culture with the compound(s) at a concentration range of 30 to 0.014 µM and analyzing for interferon (α) or tumor necrosis factor (α) in the culture supernatant. Compounds can be tested for inhibition of cytokine biosynthesis by incubating mouse macrophage cell line Raw 264.7 in a culture with the compound(s) at a single concentration of, for example, 5 µM and analyzing for tumor necrosis factor (α) in the culture supernatant. The ability to modulate cytokine biosynthesis, for example, induce the biosynthesis of one or more cytokines, makes the compounds useful in the treatment of a variety of conditions such as viral diseases and neoplastic diseases, that are responsive to such changes in the immune response.

In another aspect, the present invention provides pharmaceutical compositions containing an effective amount of a compound of Formula I, and methods of inducing cytokine biosynthesis in animal cells, treating a viral disease in an animal, and/or treating a neoplastic disease in an animal by administering to the animal an effective amount of a compound of Formula I and/or a pharmaceutically acceptable salt thereof.

In another aspect, the invention provides methods of synthesizing the compounds of Formula I and intermediates useful in the synthesis of these compounds.

As used herein, "a," "an," "the," "at least one," and "one or more" are used interchangeably.

The terms "comprising" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. Guidance is also provided herein through lists of examples, which can be used in various combinations. In each instance, the recited list serves only as a representative group and should not be interpreted as an exclusive or exhaustive list.

DETAILED DESCRIPTION OF ILLUSTRATIVE EMBODIMENTS OF THE INVENTION

The present invention provides compounds of the following Formula (I):

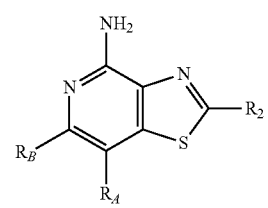

as well as more specific compounds of the following Formulas (II, III, IV, V, VI, IIIa, IVa, VIa, and VII):

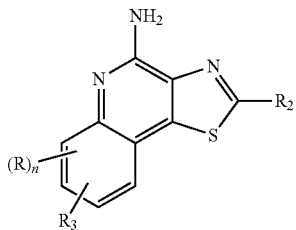
II

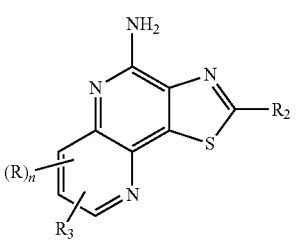
III

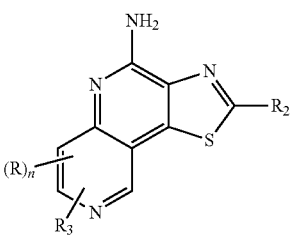
IV

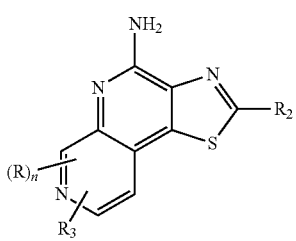
V

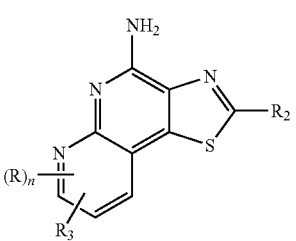
VI

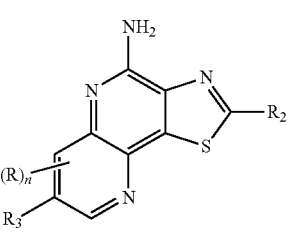
IIIa

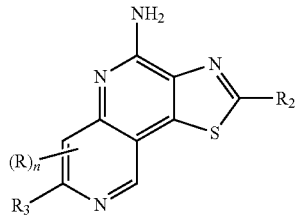
IVa

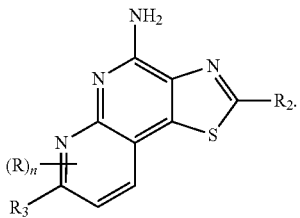
VIa

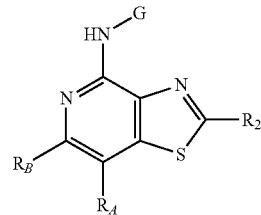
VII wherein $R_A$, $R_B$, R, $R_2$, $R_3$, G, and n are as defined below, and pharmaceutically acceptable salts thereof.

For any of the compounds presented herein, each one of the following variables (e.g., A, X, Y, Z, $R_A$, $R_B$, R, $R_2$, $R_3$, Q, G, n, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

In some embodiments, $R_A$ and $R_B$ taken together form a fused benzene ring or fused pyridine ring wherein the benzene ring or pyridine ring is substituted by one $R_3$ group, or substituted by one $R_3$ group and one R group. In some embodiments, $R_3$ is attached at the 7-position.

In some embodiments, R is selected from the group consisting of alkyl, alkoxy, hydroxy, halogen, and trifluoromethyl.

In some embodiments, $R_2$ is selected from the group consisting of hydrogen, alkyl, hydroxyalkylenyl, haloalkylenyl, alkenyl, alkyl-O-alkylenyl, alkyl-O-alkenylenyl, alkenyl-O-alkylenyl, alkenyl-O-alkenylenyl, $N(R_8)_2$-alkylenyl, $N_3$-alkylenyl, $N(R_8)_2$—C(O)—O-alkylenyl, heterocyclyl, heterocyclyl-O-alkylenyl, heterocyclyl-O-alkenylenyl, aryl, aryl-O-alkylenyl, aryl-O-alkenylenyl, heteroaryl, heteroaryl-O-alkylenyl, and heteroaryl-O-alkenylenyl.

In some embodiments, $R_2$ is selected from the group consisting of hydrogen, $C_{1-8}$ alkyl, and $C_{1-8}$ alkyl-O—$C_{1-8}$ alkylenyl. In some embodiments, $R_2$ is hydrogen, $C_{1-4}$ alkyl, or $C_{1-4}$ alkyl-O—$C_{1-4}$ alkylenyl. In some embodiments, $R_2$ is methyl, ethyl, n-propyl, n-butyl, 2-methoxyethyl, methoxymethyl, or ethoxymethyl.

In some embodiments, $R_3$ is selected from the group consisting of —O—Z—Ar, —O—Z—Ar'-$R_5$, and —O—Z—Ar'—X—$R_5$. In some embodiments, $R_3$ is —O—Z—Ar'—Y—$R_4$, —O—Z—Ar—X—Y—$R_4$, or —O—Z—Ar'—$R_5$. In some embodiments, $R_3$ is In some embodiments, $R_3$ is —O—Z—Ar.

In some embodiments, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo. In some embodiments, $R_4$ is selected from the group consisting of hydrogen, alkyl, aryl, arylalkylenyl, heteroaryl, and heteroarylalkylenyl. In some embodiments, $R_4$ is selected from the group consisting of hydrogen, alkyl, aryl, heteroaryl, and heterocyclyl. In some embodiments, $R_4$ is selected from the group consisting of alkyl, aryl, heteroaryl, heteroarylalkylenyl, and heterocyclyl. In some embodiments, $R_4$ is selected from the group consisting of alkyl, aryl, heteroaryl, and heterocyclyl.

In some embodiments, $R_5$ is selected from the group consisting of

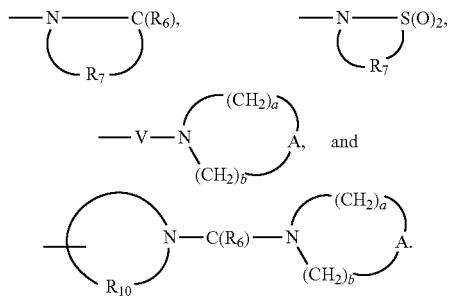

In some embodiments, $R_5$ is

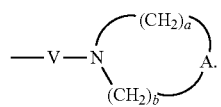

In some embodiments, $R_6$ is selected from the group consisting of $=O$ and $=S$.

In some embodiments, $R_7$ is $C_{2-7}$ alkylene.

In some embodiments, $R_8$ is selected from the group consisting of hydrogen, alkyl, alkoxyalkylenyl, and arylalkylenyl. In some embodiments, $R_8$ is selected from the group consisting of hydrogen, $C_{1-4}$ alkyl, and alkoxyalkylenyl.

In some embodiments, $R_9$ is selected from the group consisting of hydrogen and alkyl.

In some embodiments, $R_{10}$ is $C_{3-8}$ alkylene.

In some embodiments, Ar is selected from the group consisting of aryl and heteroaryl both of which can be unsubstituted or substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylene, amino, alkylamino, and dialkylamino.

In some embodiments, particularly when $R_3$ is $—O—Z—Ar$, Ar is selected from the group consisting of phenyl, naphthyl, pyridyl, pyrrolyl, thienyl, furyl, isoxazolyl, thiazolyl, imidazolyl, benzimidazolyl, 1,2,3-triazolyl, indolyl, benzothiazolyl, and oxazolyl; each of which is unsubstituted or substituted by one or more substituents independently selected from the group consisting of alkyl, alkoxy, nitro, cyano, halogen, amino, alkylamino, dialkylamino, trifluoromethoxy, aryl, and hydroxyalkyl. In some embodiments, Ar is selected from the group consisting of phenyl, naphthyl, pyridyl, pyrrolyl, thienyl, furyl, isoxazolyl, thiazolyl, and imidazolyl; each of which is unsubstituted or substituted by one or more substituents independently selected from the group consisting of alkyl, alkoxy, nitro, cyano, halogen, amino, alkylamino, dialkylamino, trifluoromethyl, and trifluoromethoxy. In some embodiments, Ar is selected from the group consisting of phenyl, naphthyl, pyridyl, pyrrolyl, thienyl, furyl, isoxazolyl, thiazolyl, and imidazolyl; each of which is unsubstituted or substituted by one or more substituents independently selected from the group consisting of alkyl, alkoxy, nitro, cyano, halogen, amino, alkylamino, dialkylamino, and trifluoromethoxy. In some embodiments, Ar is phenyl substituted by one or more substituents independently selected from the group consisting of alkyl, alkoxy, nitro, cyano, halogen, amino, alkylamino, dialkylamino, trifluoromethyl, and trifluoromethoxy. In some embodiments, Ar is phenyl substituted by one or more substituents independently selected from the group consisting of alkyl, alkoxy, nitro, cyano, halogen, amino, alkylamino, dialkylamino, and trifluoromethoxy.

In some embodiments, Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino. In some embodiments, Ar' is phenylene, naphthylene, pyridylene, pyrrolylene, thienylene, or furylene. In some embodiments, Ar' is phenylene.

In some embodiments, A is selected from the group consisting of $—O—$, $—C(O)—$, $—S(O)_{0-2}—$, $—CH_2—$, and $—N(R_4)—$.

In some embodiments, Q is selected from the group consisting of a bond, $—C(R_6)—$, $—C(R_6)—C(R_6)—$, $—S(O)_2—$, $—C(R_6)—N(R_8)—W—$, $—S(O)_2—N(R_8)—$, $—C(R_6)—O—$, and $—C(R_6)—N(OR_9)—$. In some embodiments, Q is selected from the group consisting of a bond, $—C(O)—$, $—S(O)_2—$, and $—C(R_6)—N(R_8)—$.

In some embodiments, V is selected from the group consisting of $—C(R_6)—$, $—O—C(R_6)—$, $—N(R_8)—C(R_6)—$, and $—S(O)_2—$.

In some embodiments, W is selected from the group consisting of a bond, $—C(O)—$, and $—S(O)_2—$.

In some embodiments, X is selected from the group consisting of alkylene, alkenylene, alkynylene, arylene, heteroarylene, and heterocyclylene wherein the alkylene, alkenylene, and alkynylene groups can be optionally interrupted by arylene, heteroarylene or heterocyclylene or by one or more $—O—$ groups. In some embodiments, X is $C_{1-4}$ alkylene.

In some embodiments, Y is selected from the group consisting of $—S(O)_{0-2}—$, $—S(O)_2—N(R_8)—$, $—C(R_6)—$,

—C(R$_6$)—O—, —O—C(R$_6$)—, —O—C(O)—O—, —N(R$_8$)-Q-, —C(R$_6$)—N(R$_8$)—,

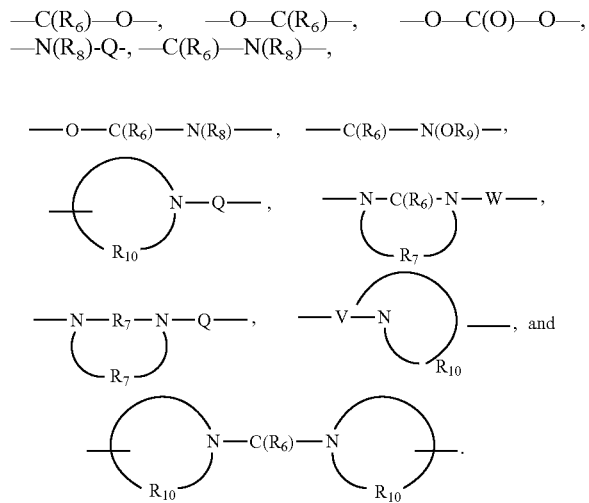

In some embodiments, Y is selected from the group consisting of —S(O)$_{0-2}$—, —C(O)—, —C(O)—O—, —N(R$_8$)-Q-, —C(R$_6$)—N(R$_8$)—, and —C(R$_6$)—N(OR$_9$)—. In some embodiments, Y is —S(O)$_{0-2}$—, —S(O)$_2$—N(R$_8$)—, —C(O)—, —N(R$_8$)—C(O)—, —N(R$_8$)—S(O)$_2$—, and —N(R$_8$)—C(R$_6$)—N(R$_8$)—. In some embodiments, Y is selected from the group consisting of —S(O)$_{0-2}$—, —C(O)—, —N(R$_8$)—C(O)—, —N(R$_8$)—S(O)$_2$—, and —N(R$_8$)—C(R$_6$)—N(R$_8$)—. In some embodiments, Y is —S(O)$_2$—, —C(O)—N(R$_8$)—, or —N(R$_8$)-Q-. In some embodiments, Y is —N(R$_8$)—C(R$_6$)—. In some embodiments, Y is —N(R$_8$)—S(O)$_2$—. In some embodiments, Y is —N(R$_8$)—C(R$_6$)—N(R$_8$)—.

In some embodiments, Z is selected from the group consisting of a bond, alkylene, alkenylene, and alkynylene wherein alkylene, alkenylene, and alkynylene are optionally interrupted with —O—. In some embodiments, Z is a bond, alkylene, or alkylene interrupted with one —O—. In some embodiments, Z is —C$_{1-3}$ alkylene-. In some embodiments, Z is —CH$_2$—.

In some embodiments, a and b are independently integers from 1 to 6 with the proviso that a+b is ≦7.

In some embodiments, n is 0 or 1. In some embodiments, n is 0.

For certain embodiments of the compounds of Formulas (I) through (VI), the —NH$_2$ group can be replaced by an —NH-G group, as shown in the compound of Formula (VII), to form prodrugs. In such embodiments, G is selected from the group consisting of: —C(O)—R', α-aminoacyl, α-aminoacyl-α-aminoacyl, —C(O)—O—R', —C(O)—N(R")R', —C(=NY')—R', —CH(OH)—C(O)—OY', —CH(OC$_{1-4}$ alkyl)Y$_0$, —CH$_2$Y$_1$, and —CH(CH$_3$)Y$_1$. In some of these embodiments G is —C(O)—R', α-aminoacyl, α-aminoacyl-α-aminoacyl, or —C(O)—O—R'. Preferably, R' and R" are independently selected from the group consisting of C$_{1-10}$ alkyl, C$_{3-7}$ cycloalkyl, and benzyl, each of which may be unsubstituted or substituted by one or more substitutents selected from the group consisting of halogen, hydroxy, nitro, cyano, carboxy, C$_{1-6}$ alkyl, C$_{1-4}$ alkoxy, aryl, heteroaryl, arylC$_{1-4}$ alkylenyl, heteroarylC$_{1-4}$ alkylenyl, haloC$_{1-4}$ alkylenyl, haloC$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$. R" can also be hydrogen. Preferably, α-aminoacyl is an acyl group derived from an amino acid selected from the group consisting of racemic, D-, and L-amino acids. Preferably, Y' is selected from the group consisting of hydrogen, C$_{1-6}$ alkyl, and benzyl. Preferably, Y$_0$ is selected from the group consisting of C$_{1-6}$ alkyl, carboxyC$_{1-6}$ alkylenyl, aminoC$_{1-4}$ alkylenyl, mono-N—C$_{1-6}$ alkylaminoC$_{1-4}$ alkylenyl, and di-N,N—C$_{1-6}$ alkylaminoC$_{1-4}$ alkylenyl. Preferably, Y$_1$ is selected from the group consisting of mono-N—C$_{1-6}$alkylamino, di-N,N—C$_{1-6}$alkylamino, morpholin-4-yl, piperidin-1-yl, pyrrolidin-1-yl, and 4-C$_{1-4}$ alkylpiperazin-1-yl.

In some embodiments, R$_3$ is —O—Z—Ar'—Y—R$_4$, —O—Z—Ar—X—Y—R$_4$, or —O—Z—Ar'—R$_5$. In some embodiments, R$_3$ is —O—Z—Ar'—Y—R$_4$. In such embodiments of R$_3$, Ar' is phenylene, naphthylene, pyridylene, pyrrolylene, thienylene, or furylene; Y is selected from the group consisting of —S(O)$_{0-2}$—, —C(O)—, —C(O)—O—, —N(R$_8$)-Q-, —C(R$_6$)—N(R$_8$)—, and —C(R$_6$)—N(OR$_9$)—; X is C$_{1-4}$ alkylene; R$_4$ is selected from the group consisting of hydrogen, alkyl, aryl, heteroaryl, and heterocyclyl; and R$_5$ is

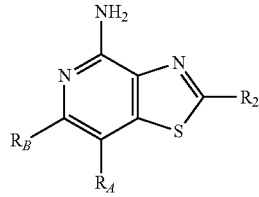

In such embodiments, preferably, Q is selected from the group consisting of a bond, —C(O)—, —S(O)$_2$—, and —C(R$_6$)—N(R$_8$)—; and R$_8$ is selected from the group consisting of hydrogen, C$_{1-4}$ alkyl, and alkoxyalkylenyl.

Alternatively, in such embodiments of R$_3$, particularly when R$_3$ is preferably Ar' is phenylene, naphthylene, pyridylene, pyrrolylene, thienylene, or furylene (more preferably, phenylene); Y is selected from the group consisting of —S(O)$_{0-2}$—, —S(O)$_2$—N(R$_8$)—, —C(O)—, —N(R$_8$)—C(O)—, —N(R$_8$)—S(O)$_2$—, and —N(R$_8$)—C(R$_6$)—N(R$_8$)—; and R$_4$ is selected from the group consisting of alkyl, aryl, heteroaryl, heteroarylalkylenyl, and heterocyclyl. In such embodiments, preferably, R$_8$ is selected from the group consisting of hydrogen, C$_{1-4}$ alkyl, and alkoxyalkylenyl.

In some embodiments of R$_3$, Y is —N(R$_8$)—C(R$_6$)—; R$_4$ is alkyl, aryl, heteroaryl, or heterocyclyl; and R$_8$ is hydrogen, C$_{1-4}$ alkyl, or alkoxyalkylenyl. In some embodiments of R$_3$, Y is —N(R$_8$)—S(O)$_2$—; R$_4$ is alkyl, aryl, heteroaryl, or heterocyclyl; and R$_8$ is hydrogen, C$_{1-4}$ alkyl, or alkoxyalkylenyl. In some embodiments of R$_3$, Y is —N(R$_8$)—C(R$_6$)—N(R$_8$)—; R$_4$ is alkyl, aryl, heteroaryl, or heterocyclyl; and R$_8$ is hydrogen, C$_{1-4}$ alkyl, or alkoxyalkylenyl.

In some embodiments of R$_3$, Y is —S(O)$_2$—, —C(O)—N(R$_8$)—, or —N(R$_8$)-Q-; R$_8$ is selected from the group consisting of hydrogen, C$_{1-4}$ alkyl, and alkoxyalkylenyl; and R$_4$ is selected from the group consisting of hydrogen, alkyl, aryl, arylalkylenyl, heteroaryl, and heteroarylalkylenyl.

In one aspect, the present invention provides thiazoloquinoline and thiazolonaphthyridine compounds of the following formula (I):

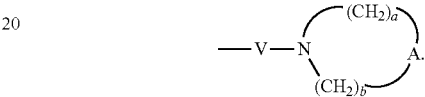

wherein:

$R_A$ and $R_B$ taken together form a fused benzene ring or fused pyridine ring wherein the benzene ring or pyridine ring is substituted by one $R_3$ group, or substituted by one $R_3$ group and one R group;

$R_2$ is selected from the group consisting of:
hydrogen,
alkyl,
hydroxyalkylenyl,
haloalkylenyl,
alkenyl,
alkyl-O-alkylenyl,
alkyl-O-alkenylenyl,
alkenyl-O-alkylenyl,
alkenyl-O-alkenylenyl,
$N(R_8)_2$-alkylenyl,
$N_3$-alkylenyl,
$N(R_8)_2$—C(O)—O-alkylenyl,
heterocyclyl,
heterocyclyl-O-alkylenyl,
heterocyclyl-O-alkenylenyl,
aryl,
aryl-O-alkylenyl,
aryl-O-alkenylenyl,
heteroaryl,
heteroaryl-O-alkylenyl, and
heteroaryl-O-alkenylenyl;

$R_3$ is selected from the group consisting of:
—O—Z—Ar,
—O—Z—Ar'-Y—$R_4$,
—O—Z—Ar'—$R_5$, and
—O—Z—Ar'—X—$R_5$;

Z is selected from the group consisting of a bond, alkylene, alkenylene, and alkynylene wherein alkylene, alkenylene, and alkynylene are optionally interrupted with —O—;

Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylene, amino, alkylamino, and dialkylamino;

Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;

X is selected from the group consisting of alkylene, alkenylene, alkynylene, arylene, heteroarylene, and heterocyclylene wherein the alkylene, alkenylene, and alkynylene groups can be optionally interrupted by arylene, heteroarylene or heterocyclylene or by one or more —O— groups.

Y is selected from the group consisting of:
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,

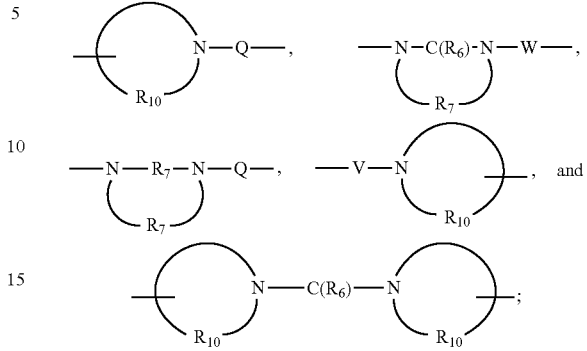

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

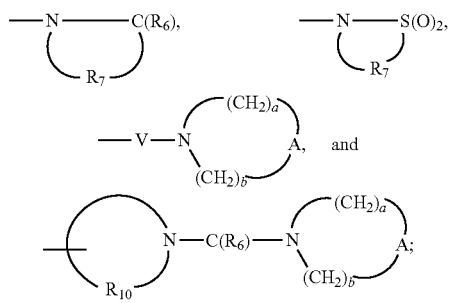

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, —CH$_2$—, and —N($R_4$)—;
Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, and —C($R_6$)—N(O$R_9$)—;
V is selected from the group consisting of —C($R_6$)—, —O—C($R_6$)—, —N($R_8$)—C($R_6$)—, and —S(O)$_2$—;
W is selected from the group consisting of a bond, —C(O)—, and —S(O)$_2$—;

a and b are independently integers from 1 to 6 with the proviso that a+b is ≦7; and R is selected from the group consisting of alkyl, alkoxy, hydroxy, halogen, and trifluoromethyl;

or a pharmaceutically acceptable salt thereof.

In some embodiments, compounds or salts of Formula I induce the biosynthesis of one or more cytokines.

In some embodiments of Formula I, Z is a bond, alkylene, or alkylene interrupted with one —O—. In certain embodiments, Z is —$C_{1-3}$ alkylene-.

In some embodiments of Formula I, $R_3$ is —O—Z—Ar. In certain embodiments, Z is a bond, alkylene, or alkylene interrupted with one —O—. In certain embodiments, Z is —$C_{1-3}$ alkylene-.

In some embodiments of Formula I, $R_3$ is —O—Z—Ar'—Y—$R_4$, —O—Z—Ar'—X—Y—$R_4$, or —O—Z—Ar—$R_5$. In certain embodiments, Z is a bond, alkylene, or alkylene interrupted with one —O—. In certain embodiments, Z is —$C_{1-3}$ alkylene-.

In some embodiments of Formula I, $R_3$ is —O—Z—Ar'—Y—$R_4$. In certain embodiments, Z is a bond, alkylene, or alkylene interrupted with one —O—. In certain embodiments, Z is —$C_{1-3}$ alkylene-. In certain embodiments, Y is —S(O)$_2$—, —C(O)—N($R_8$)—, or —N($R_8$)-Q-; $R_8$ is selected from the group consisting of hydrogen, $C_{1-4}$ alkyl, and alkoxyalkylenyl; and $R_4$ is selected from the group consisting of hydrogen, alkyl, aryl, arylalkylenyl, heteroaryl, and heteroarylalkylenyl.

For some embodiments of Formula I or any one of the above embodiments, $R_2$ is selected from the group consisting of hydrogen, $C_{1-8}$ alkyl, and $C_{1-8}$alkyl-O—$C_{1-8}$alkylenyl.

The present invention also provides thiazoloquinoline compounds of the following formula (II):

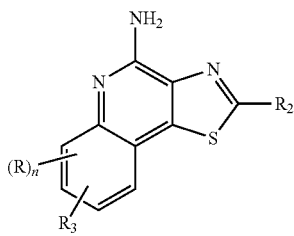

wherein:

$R_2$ is selected from the group consisting of:
hydrogen,
alkyl,
hydroxyalkylenyl,
haloalkylenyl,
alkenyl,
alkyl-O-alkylenyl,
alkyl-O-alkenylenyl,
alkenyl-O-alkylenyl,
alkenyl-O-alkenylenyl,
N($R_8$)$_2$-alkylenyl,
$N_3$-alkylenyl,
N($R_8$)$_2$—C(O)—O-alkylenyl,
heterocyclyl,
heterocyclyl-O-alkylenyl,
heterocyclyl-O-alkenylenyl,
aryl,
aryl-O-alkylenyl,
aryl-O-alkenylenyl,
heteroaryl,
heteroaryl-O-alkylenyl, and
heteroaryl-O-alkenylenyl;

$R_3$ is selected from the group consisting of:
—O—Z—Ar,
—O—Z—Ar'—Y—$R_4$,
—O—Z—Ar'—X—Y—$R_4$,
—O—Z—Ar'—$R_5$, and
—O—Z—Ar'—X—$R_5$;

Z is selected from the group consisting of a bond, alkylene, alkenylene, and alkynylene wherein alkylene, alkenylene, and alkynylene are optionally interrupted with —O—;

Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylene, amino, alkylamino, and dialkylamino;

Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;

X is selected from the group consisting of alkylene, alkenylene, alkynylene, arylene, heteroarylene, and heterocyclylene wherein the alkylene, alkenylene, and alkynylene groups can be optionally interrupted by arylene, heteroarylene or heterocyclylene or by one or more —O— groups.

Y is selected from the group consisting of:
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,

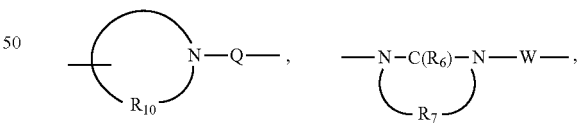

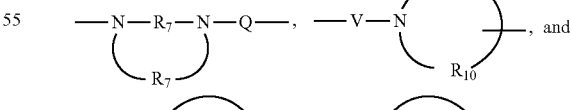, and

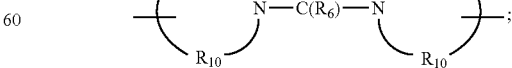;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino) alkyleneoxy, and in the case of alkyl, alkenyl, alkynyl, and heterocyclyl, oxo;

$R_5$ is selected from the group consisting of:

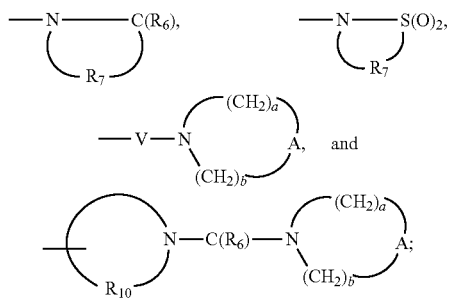

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—;
a and b are independently integers from 1 to 6 with the proviso that a+b is ≦7;
R is selected from the group consisting of alkyl, alkoxy, hydroxy, halogen, and trifluoromethyl; and
n is 0 or 1;
or a pharmaceutically acceptable salt thereof.

In some embodiments of Formula II, Z is a bond, alkylene, or alkylene interrupted with one —O—. In certain embodiments, Z is —C$_{1-3}$ alkylene-. In certain embodiments, Z is —CH$_2$—.

In some embodiments of Formula II, R$_3$ is —O—Z—Ar. In certain embodiments, Ar is selected from the group consisting of phenyl, naphthyl, pyridyl, pyrrolyl, thienyl, furyl, isoxazolyl, thiazolyl, imidazolyl, benzimidazolyl, indolyl, benzothiazolyl, and oxazolyl; each of which is unsubstituted or substituted by one or more substituents independently selected from the group consisting of alkyl, alkoxy, nitro, cyano, halogen, amino, alkylamino, dialkylamino, trifluoromethoxy, aryl, and hydroxyalkyl. In certain embodiments, Ar is selected from the group consisting of phenyl, naphthyl, pyridyl, pyrrolyl, thienyl, furyl, isoxazolyl, thiazolyl, and imidazolyl; each of which is unsubstituted or substituted by one or more substituents independently selected from the group consisting of alkyl, alkoxy, nitro, cyano, halogen, amino, alkylamino, dialkylamino, trifluoromethyl, or trifluoromethoxy. In certain embodiments, Ar is selected from the group consisting of phenyl, naphthyl, pyridyl, pyrrolyl, thienyl, furyl, isoxazolyl, thiazolyl, and imidazolyl; each of which is unsubstituted or substituted by one or more substituents independently selected from the group consisting of alkyl, alkoxy, nitro, cyano, halogen, amino, alkylamino, dialkylamino, and trifluoromethoxy.

In certain embodiments, Ar is phenyl substituted by one or more substituents independently selected from the group consisting of alkyl, alkoxy, nitro, cyano, halogen, amino, alkylamino, dialkylamino, trifluoromethyl, or trifluoromethoxy. In certain embodiments, phenyl substituted by one or more substituents independently selected from the group consisting of alkyl, alkoxy, nitro, cyano, halogen, amino, alkylamino, dialkylamino, and trifluoromethoxy. In certain embodiments, Z is —C$_{1-3}$ alkylene-. In certain embodiments, Z is —CH$_2$—.

In some embodiments of Formula II, R$_3$ is —O—Z—Ar'-Y—R$_4$, —O—Z—Ar—X—Y—R$_4$, or —O—Z—Ar'—R$_5$. In certain embodiments, Ar' is phenylene, naphthylene, pyridylene, pyrrolylene, thienylene, or furylene; Y is selected from the group consisting of —S(O)$_{0-2}$—, —C(O)—, —C(O)—O—, —N(R$_8$)-Q-, —C(R$_6$)—N(R$_8$)—, and —C(R$_6$)—N(OR$_9$)—;
wherein Q is selected from the group consisting of a bond, —C(O)—, —S(O)$_2$—, and —C(R$_6$)—N(R$_8$)—; and R$_8$ is selected from the group consisting of hydrogen, C$_{1-4}$ alkyl, and alkoxyalkylenyl; X is C$_{1-4}$ alkylene; R$_4$ is selected from the group consisting of hydrogen, alkyl, aryl, heteroaryl, and heterocyclyl; and R$_5$ is

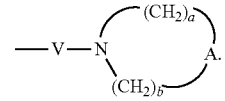

In certain embodiments, Z is —C$_{1-3}$ alkylene-. In certain embodiments, Z is —CH$_2$—. In certain embodiments, R$_3$ is —O—Z—Ar'—Y—R$_4$.

In some embodiments of Formula II, R$_3$ is —O—Z—Ar'—Y—R$_4$. In certain embodiments, Ar' is phenylene, naphthylene, pyridylene, pyrrolylene, thienylene, or furylene; Y is selected from the group consisting of —S(O)$_{0-2}$—, —C(O)—, —N(R$_8$)—C(O)—, —N(R$_8$)—S(O)$_2$—, and —N(R$_8$)—C(R$_6$)—N(R$_8$)—, wherein R$_8$ is selected from the group consisting of hydrogen, C$_{1-4}$ alkyl, and alkoxyalkylenyl; and R$_4$ is selected from the group consisting of alkyl, aryl, heteroaryl, and heterocyclyl. In certain embodiments, Y is —N(R$_8$)—C(R$_6$)—; R$_4$ is alkyl, aryl, heteroaryl, or heterocyclyl; and R$_8$ is hydrogen, C$_{1-4}$ alkyl, or alkoxyalkylenyl. In certain other embodiments, Y is —N(R$_8$)—S(O)$_2$—; R$_4$ is alkyl, aryl, heteroaryl, or heterocyclyl; and R$_8$ is hydrogen, C$_{1-4}$ alkyl, or alkoxyalkylenyl. In certain other embodiments, Y is —N(R$_8$)—C(R$_6$)—N(R$_8$)—; R$_4$ is alkyl, aryl, heteroaryl, or heterocyclyl; and R$_8$ is hydrogen, C$_{1-4}$ alkyl, or alkoxyalkylenyl.

In some embodiments of Formula II and any one of the above embodiments of Formula II, R$_2$ is selected from the group consisting of hydrogen, C$_{1-8}$ alkyl, and C$_{1-8}$alkyl-O—C$_{1-8}$alkylenyl. In certain embodiments, R$_2$ is hydrogen, C$_{1-4}$ alkyl or C$_{1-4}$ alkyl-O—C$_{1-4}$alkylenyl. In certain more specific embodiments, R$_2$ is methyl, ethyl, n-propyl, n-butyl, 2-methoxyethyl, methoxymethyl, or ethoxymethyl.

In some embodiments of Formula II and any one of the above embodiments of Formula II, $R_3$ is attached at the 7-position.

In some embodiments of Formula II and any one of the above embodiments of Formula II, n is 0.

The present invention also provides thiazolonaphthyridine compounds of the following formulas (III, IV, V, and VI):

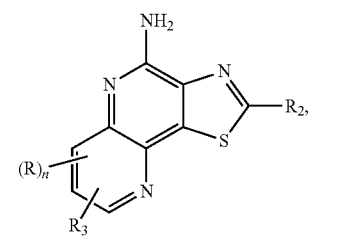
III

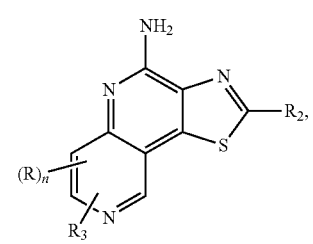
IV

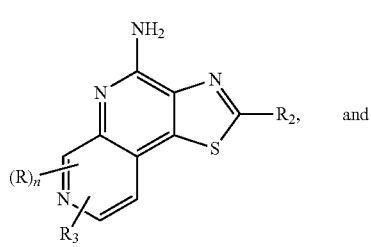
V
and

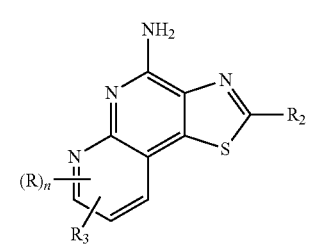
VI wherein:
$R_2$ is selected from the group consisting of:
hydrogen,
alkyl,
hydroxyalkylenyl,
haloalkylenyl,
alkenyl,
alkyl-O-alkylenyl,
alkyl-O-alkenylenyl,
alkenyl-O-alkylenyl,
alkenyl-O-alkenylenyl,
$N(R_8)_2$-alkylenyl,
$N_3$-alkylenyl,
$N(R_8)_2$—C(O)—O-alkylenyl,
heterocyclyl,
heterocyclyl-O-alkylenyl,
heterocyclyl-O-alkenylenyl,
aryl,
aryl-O-alkylenyl,
aryl-O-alkenylenyl,
heteroaryl,
heteroaryl-O-alkylenyl, and
heteroaryl-O-alkenylenyl;

$R_3$ is selected from the group consisting of:
—O—Z—Ar,
—O—Z—Ar'—Y—$R_4$,
—O—Z—Ar'—X—Y—$R_4$,
—O—Z—Ar'—$R_5$, and
—O—Z—Ar'—X—$R_5$;

Z is selected from the group consisting of a bond, alkylene, alkenylene, and alkynylene wherein alkylene, alkenylene, and alkynylene are optionally interrupted with —O—;

Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylene, amino, alkylamino, and dialkylamino;

Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;

X is selected from the group consisting of alkylene, alkenylene, alkynylene, arylene, heteroarylene, and heterocyclylene wherein the alkylene, alkenylene, and alkynylene groups can be optionally interrupted by arylene, heteroarylene or heterocyclylene or by one or more —O— groups.

Y is selected from the group consisting of:
—$S(O)_{0-2}$—,
—$S(O)_2$—$N(R_8)$—,
—$C(R_6)$—,
—$C(R_6)$—O—,
—O—$C(R_6)$—,
—O—C(O)—O—,
—$N(R_8)$-Q-,
—$C(R_6)$—$N(R_8)$—,
—O—$C(R_6)$—$N(R_8)$—,
—$C(R_6)$—$N(OR_9)$—,

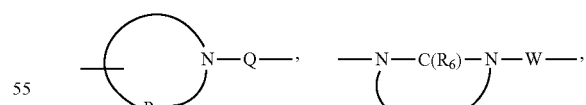

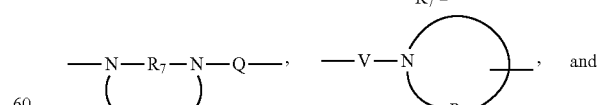
and

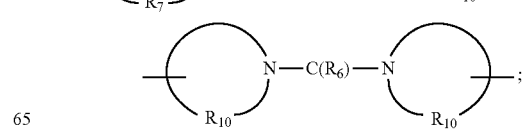

R₄ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

R₅ is selected from the group consisting of:

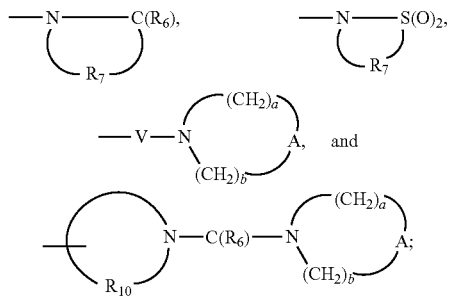

R₆ is selected from the group consisting of =O and =S;
R₇ is C₂₋₇ alkylene;
R₈ is selected from the group consisting of hydrogen, alkyl, alkoxyalkylenyl, and arylalkylenyl;
R₉ is selected from the group consisting of hydrogen and alkyl;
R₁₀ is C₃₋₈ alkylene;
A is selected from the group consisting of —O—, —C(O)—, —S(O)₀₋₂—, —CH₂—, and —N(R₄)—;
Q is selected from the group consisting of a bond, —C(R₆)—, —C(R₆)—C(R₆)—, —S(O)₂—, —C(R₆)—N(R₈)—W—, —S(O)₂—N(R₈)—, —C(R₆)—O—, and —C(R₆)—N(OR₉)—;
V is selected from the group consisting of —C(R₆)—, —O—C(R₆)—, —N(R₈)—C(R₆)—, and —S(O)₂—;
W is selected from the group consisting of a bond, —C(O)—, and —S(O)₂—;
a and b are independently integers from 1 to 6 with the proviso that a+b is ≤7;
R is selected from the group consisting of alkyl, alkoxy, hydroxy, halogen, and trifluoromethyl; and
n is 0 or 1;
or a pharmaceutically acceptable salt thereof.

In some embodiments of Formulas III, IV, V, and VI, Z is a bond, alkylene, or alkylene interrupted with one —O—. In certain embodiments, Z is —C₁₋₃ alkylene-. In certain embodiments, Z is —CH₂—.

In some embodiments of Formulas III, IV, V, and VI, R₃ is —O—Z—Ar. In certain embodiments, Ar is selected from the group consisting of phenyl, naphthyl, pyridyl, pyrrolyl, thienyl, furyl, isoxazolyl, thiazolyl, and imidazolyl; each of which is unsubstituted or substituted by one or more substituents independently selected from the group consisting of alkyl, alkoxy, nitro, cyano, halogen, amino, alkylamino, dialkylamino, trifluoromethyl, or trifluoromethoxy. In certain embodiments, Ar is phenyl substituted by one or more substituents independently selected from the group consisting of alkyl, alkoxy, nitro, cyano, halogen, amino, alkylamino, dialkylamino, trifluoromethyl, or trifluoromethoxy. In certain embodiments, Z is —C₁₋₃ alkylene-. In certain embodiments, Z is —CH₂—.

In some embodiments of Formulas III, IV, V, and VI, R₃ is —O—Z—Ar'—Y—R₄, —O—Z—Ar'—X—Y—R₄, or —O—Z—Ar'—R₅. In certain embodiments, Ar' is phenylene, naphthylene, pyridylene, pyrrolylene, thienylene, or furylene; Y is selected from the group consisting of —S(O)₀₋₂—, —C(O)—, —C(O)—O—, —N(R₈)-Q-, —C(R₆)—N(R₉)—, and —C(R₆)—N(OR₉)—;
wherein Q is selected from the group consisting of a bond, —C(O)—, —S(O)₂—, and —C(R₆)—N(R₈)—; and R₈ is selected from the group consisting of hydrogen, C₁₋₄ alkyl, and alkoxyalkylenyl; X is C₁₋₄ alkylene; R₄ is selected from the group consisting of hydrogen, alkyl, aryl, heteroaryl, and heterocyclyl; and R₅ is

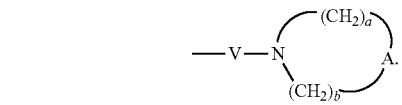

In certain embodiments, Z is —C₁₋₃ alkylene-. In certain embodiments, Z is —CH₂—. In certain embodiments, R₃ is —O—Z—Ar'—Y—R₄.

In some embodiments of Formulas III, IV, V, and VI, R₃ is —O—Z—Ar'—Y—R₄. In certain embodiments, Y is —N(R₈)—C(R₆)—; R₄ is alkyl, aryl, heteroaryl, or heterocyclyl; and R₈ is hydrogen, C₁₋₄ alkyl, or alkoxyalkylenyl. In certain other embodiments, Y is —N(R₈)—S(O)₂—; R₄ is alkyl, aryl, heteroaryl, or heterocyclyl; and R₈ is hydrogen, C₁₋₄ alkyl, or alkoxyalkylenyl. In certain other embodiments, Y is —N(R₈)—C(R₆)—N(R₈)—; R₄ is alkyl, aryl, heteroaryl, or heterocyclyl; and R₈ is hydrogen, C₁₋₄ alkyl, or alkoxyalkylenyl.

In some embodiments of Formulas III, IV, V, and VI and any one of the above embodiments of Formulas III, IV, V, and VI, R₂ is selected from the group consisting of hydrogen, C₁₋₈ alkyl, and C₁₋₈ alkyl-O—C₁₋₈ alkylenyl. In certain embodiments, R₂ is hydrogen, C₁₋₄ alkyl or C₁₋₄ alkyl-O—C₁₋₄ alkylenyl. In certain more specific embodiments, R₂ is methyl, ethyl, n-propyl, n-butyl, 2-methoxyethyl, methoxymethyl, or ethoxymethyl.

In some embodiments of Formulas III, IV, and VI and any one of the above embodiments described above for Formulas III, IV, and VI, R₃ is attached at the 7-position. That is, the thiazolonaphthyridines selected from Formulas III, IV, V, and VI are the compounds of the formulas (IIIa, IVa, and VIa):

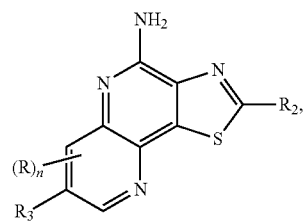

IIIa

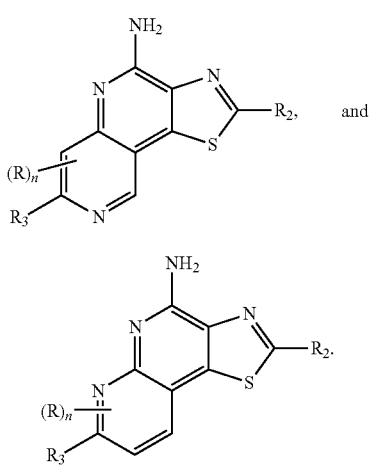

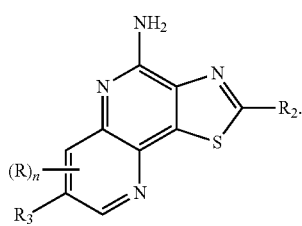

In some embodiments, the thiazolonaphthyridines selected from Formulas III, IV, V, and VI or any one of the above embodiments described above for Formulas III, IV, V, and VI are the compounds of the formula (III):

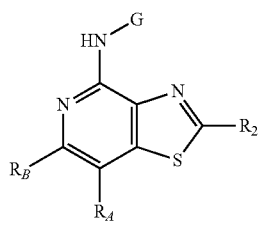

In some embodiments of Formulas III, IV, V, and VI or any one of the above embodiments of Formulas III, IV, V, and VI, n is 0.

In another aspect of the invention, there is provided a compound (which is a prodrug) of the formula (VII):

VII wherein:
$R_A$ and $R_B$ taken together form a fused benzene ring or fused pyridine ring wherein the benzene ring or pyridine ring is substituted by one $R_3$ group, or substituted by one $R_3$ group and one R group;

$R_2$ is selected from the group consisting of:
hydrogen,
alkyl,
hydroxyalkylenyl,
haloalkylenyl,
alkenyl,
alkyl-O-alkylenyl,
alkyl-O-alkenylenyl,
alkenyl-O-alkylenyl,
alkenyl-O-alkenylenyl,
$N(R_8)_2$-alkylenyl,
$N_3$-alkylenyl,
$N(R_8)_2$—C(O)—O-alkylenyl,
heterocyclyl,
heterocyclyl-O-alkylenyl,
heterocyclyl-O-alkenylenyl,
aryl,
aryl-O-alkylenyl,
aryl-O-alkenylenyl,
heteroaryl,
heteroaryl-O-alkylenyl, and
heteroaryl-O-alkenylenyl;

$R_3$ is selected from the group consisting of:
—O—Z—Ar,
—O—Z—Ar'—Y—$R_4$,
—O—Z—Ar'—X—Y—$R_4$,
—O—Z—Ar'—$R_5$, and
—O—Z—Ar'—X—$R_5$;

Z is selected from the group consisting of a bond, alkylene, alkenylene, and alkynylene wherein alkylene, alkenylene, and alkynylene are optionally interrupted with —O—;

Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylene, amino, alkylamino, and dialkylamino;

Ar' is selected from the group consisting of arylene and heteroarylene both of which can be unsubstituted or can be substituted by one or more substituents independently selected from the group consisting of alkyl, alkenyl, alkoxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylenyl, amino, alkylamino, and dialkylamino;

X is selected from the group consisting of alkylene, alkenylene, alkynylene, arylene, heteroarylene, and heterocyclylene wherein the alkylene, alkenylene, and alkynylene groups can be optionally interrupted by arylene, heteroarylene or heterocyclylene or by one or more —O— groups.

Y is selected from the group consisting of:
—S(O)$_{0-2}$—,
—S(O)$_2$—N($R_8$)—,
—C($R_6$)—,
—C($R_6$)—O—,
—O—C($R_6$)—,
—O—C(O)—O—,
—N($R_8$)-Q-,
—C($R_6$)—N($R_8$)—,
—O—C($R_6$)—N($R_8$)—,
—C($R_6$)—N(O$R_9$)—,

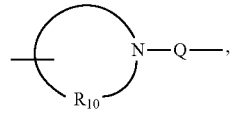 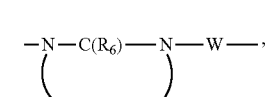

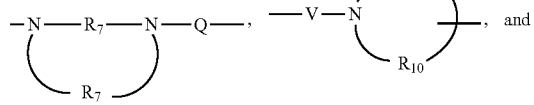

-continued

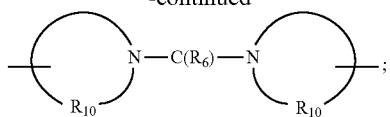

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo;

$R_5$ is selected from the group consisting of:

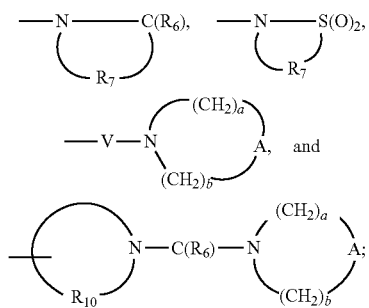

$R_6$ is selected from the group consisting of =O and =S;
$R_7$ is $C_{2-7}$ alkylene;
$R_8$ is selected from the group consisting of hydrogen, alkyl, alkoxyalkylenyl, and arylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, —CH$_2$—, and —N(R$_4$)—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—;
a and b are independently integers from 1 to 6 with the proviso that a+b is ≦7;
R is selected from the group consisting of alkyl, alkoxy, hydroxy, halogen, and trifluoromethyl;
G is selected from the group consisting of:
—C(O)—R',
α-aminoacyl,
α-aminoacyl-α-aminoacyl,
—C(O)—O—R',
—C(O)—N(R")R',
—CH(OH)—C(O)—OY',
—CH(OC$_{1-4}$ alkyl)Y$_0$,
—CH$_2$Y$_1$, and
—CH(CH$_3$)Y$_1$;

R' and R" are independently selected from the group consisting of $C_{1-10}$ alkyl, $C_{3-7}$ cycloalkyl, and benzyl, each of which may be unsubstituted or substituted by one or more substitutents selected from the group consisting of halogen, hydroxy, nitro, cyano, carboxy, $C_{1-6}$ alkyl, $C_{1-4}$ alkoxy, aryl, heteroaryl, arylC$_{1-4}$ alkylenyl, heteroarylC$_{1-4}$ alkylenyl, haloC$_{1-4}$ alkylenyl, haloC$_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen;

α-aminoacyl is an acyl group derived from an amino acid selected from the group consisting of racemic, D-, and L-amino acids;

Y' is selected from the group consisting of hydrogen, $C_{1-6}$ alkyl, and benzyl;

$Y_0$ is selected from the group consisting of $C_{1-6}$ alkyl, carboxyC$_{1-6}$ alkylenyl, aminoC$_{1-4}$ alkylenyl, mono-N—C$_{1-6}$alkylaminoC$_{1-4}$ alkylenyl, and di-N,N—C$_{1-6}$alkylaminoC$_{1-4}$alkylenyl;

$Y_1$ is selected from the group consisting of mono-N—C$_{1-6}$ alkylamino, di-N,N—C$_{1-6}$ alkylamino, morpholin-4-yl, piperidin-1-yl, pyrrolidin-1-yl, and 4-C$_{1-4}$ alkylpiperazin-1-yl;

or a pharmaceutically acceptable salt thereof.

As used herein, the terms "alkyl," "alkenyl," "alkynyl" and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene," "alkenylene," and "alkynylene" are the divalent forms of the "alkyl," "alkenyl," and "alkynyl" groups defined above. The terms "alkylenyl," "alkenylenyl," and "alkynylenyl" are used when "alkylene", "alkenylene:, and "alkynylene", respectively, are substituted. For example, an arylalkylenyl group comprises an "alkylene" moiety to which an aryl group is attached.

The term "haloalkyl" is inclusive of alkyl groups that are substituted by one or more halogen atoms, including perfluorinated groups. This is also true of other groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

The term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2 to 12 carbon atoms, 1 to 3 rings, 1 to 4 heteroatoms, and O, S, and N as the heteroatoms. Exemplary heterocyclic groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), homopiperazinyl (diazepanyl), 1,4-oxazepanyl, 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

The term "heterocyclyl" includes bicyclic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one spiro atom and three rings joined by two spiro atoms.

When "heterocyclyl" contains a nitrogen atom, the point of attachment of the heterocyclyl group may be the nitrogen atom.

The terms "arylene," "heteroarylene," and "heterocyclylene" are the divalent forms of the "aryl," "heteroaryl," and "heterocyclyl" groups defined above. Likewise, "arylenyl," "heteroarylenyl," and "heterocyclylenyl" are the divalent forms of the "aryl," "heteroaryl," and "heterocyclyl" groups defined above. For example, an alkylarylenyl group comprises an arylene moiety to which an alkyl group is attached.

When a group (or substituent or variable) is present more that once in any Formula described herein, each group (or substituent or variable) is independently selected, whether specifically stated or not. For example, for the formula $N(R_8)_2$-alkylenyl, each $R_8$ group is independently selected.

The invention is inclusive of the compounds described herein and salts thereof in any of their pharmaceutically acceptable forms, including isomers such as diastereomers and enantiomers, solvates, polymorphs, prodrugs, and the like. In particular, if a compound is optically active, the invention specifically includes each of the compound's enantiomers as well as racemic mixtures of the enantiomers. It should be understood that the term "compound" includes any or all of such forms, whether explicitly stated or not (although at times, "salts" are explicitly stated).

The term "prodrug" means a compound that can be transformed in vivo to yield an immune response modifying compound in any of the salt, solvated, polymorphic, or isomeric forms described above. The prodrug, itself, may be an immune response modifying compound in any of the salt, solvated, polymorphic, or isomeric forms described above. The transformation may occur by various mechanisms, such as through a chemical (e.g., solvolysis or hydrolysis, for example, in the blood) or enzymatic biotransformation. A discussion of the use of prodrugs is provided by T. Higuchi and W. Stella, "Pro-drugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987.

Preparation of the Compounds

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

For illustrative purposes, the reaction schemes depicted below provide potential routes for synthesizing the compounds of the present invention as well as key intermediates. For more detailed description of the individual reaction steps, see the EXAMPLES section below. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

Conventional methods and techniques of separation and purification can be used to isolate compounds of the invention, as well as various intermediates related thereto. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

Compounds of the invention can be prepared according to Reaction Scheme I where R, $R_2$, and n are as defined above and $R_{3a}$ is —Z—Ar or —Z—Ar'—Y—$R_4$, where Z, Ar, Ar', Y, and $R_4$ are as defined above. In step (1) of Reaction Scheme I, a benzyloxyaniline of Formula XV is treated with the condensation product generated from 2,2-dimethyl-1,3-dioxane-4,6-dione (Meldrum's acid) and triethyl orthoformate to provide a dione of Formula XVI. The reaction is conveniently carried out by adding a solution of a benzyloxyaniline of Formula XV to a heated mixture of Meldrum's acid and triethyl orthoformate and heating the reaction at an elevated temperature such as 45° C.

In step (2) of Reaction Scheme I, a dione of Formula XVI undergoes thermolysis and cyclization to provide a benzyloxyquinolin-4-ol of Formula XVII. The reaction is conveniently carried out in a heat transfer fluid such as DOWTHERM A at a temperature between 200 and 250° C.

In step (3) of Reaction Scheme I, the benzyloxyquinolin-4-ol of Formula XVII is nitrated under conventional nitration conditions to provide a benzyloxy-3-nitroquinolin-4-ol of Formula XVIII. The reaction is conveniently carried out by adding nitric acid to the benzyloxyquinolin-4-ol of Formula XVII in a suitable solvent such as propionic acid and heating the mixture at an elevated temperature such as 125° C.

In step (4) of Reaction Scheme I, a benzyloxy-3-nitroquinolin-4-ol of Formula XVIII is reduced to provide a 3-amino-benzyloxyquinolin-4-ol of Formula XIX. The reaction can be carried out by hydrogenation using a heterogeneous hydrogenation catalyst such as platinum on carbon. The hydrogenation is conveniently carried out in a Parr apparatus in a suitable solvent such as N,N-dimethylformamide. The reaction can be carried out at ambient temperature.

In step (5) of Reaction Scheme I, a 3-amino-benzyloxyquinolin-4-ol of Formula XIX is reacted with a carboxylic acid or an equivalent thereof to provide a compound of Formula XX. Suitable equivalents to carboxylic acid include acid anhydrides and acid chlorides. The reaction is conveniently carried out by adding the acid chloride to a solution of a 3-amino-benzyloxyquinolin-4-ol of Formula XIX in a suitable solvent such as dichloromethane or acetonitrile in the presence of a tertiary amine such as triethylamine, pyridine, or 4-dimethylaminopyridine to afford an amide. The reaction can be carried out at or below ambient temperature.

In step (6) of Reaction Scheme I, an amide of Formula XX is reacted with phosphorus pentasulfide to provide a benzyloxy-thiazolo[4,5-c]quinoline of Formula XXI. The reaction can be carried out by adding phosphorus pentasulfide to a solution or suspension of a compound of Formula XX in a suitable solvent such as pyridine and heating the resulting mixture.

In step (7) of Reaction Scheme I, a benzyloxy-thiazolo[4,5-c]quinoline of Formula XXI is oxidized to provide a benzyloxy-thiazolo[4,5-c]quinoline-5N-oxide of Formula XXII using a conventional oxidizing agent capable of forming N-oxides. The reaction is conveniently carried out by adding 3-chloroperoxybenzoic acid to a solution of a compound of Formula XXI in a solvent such dichloromethane or chloroform. The reaction can be carried out at ambient temperature.

In step (8) of Reaction Scheme I, a benzyloxy-thiazolo[4,5-c]quinoline-5N-oxide of Formula XXII is aminated to provide a benzyloxy-thiazolo[4,5-c]quinolin-4-amine of Formula XXIII. Step (8) can be carried out by the activation of an N-oxide of Formula XXII by conversion to an ester and then reacting the ester with an aminating agent. Suitable activating agents include alkyl- or arylsulfonyl chlorides such as benzenesulfonyl chloride, methanesulfonyl chloride, or p-toluenesulfonyl chloride. Suitable aminating agents include ammonia, in the form of ammonium hydroxide, for example, and ammonium salts such as ammonium carbonate, ammonium bicarbonate, and ammonium phosphate. The reaction is conveniently carried out by adding ammonium hydroxide followed by p-toluenesulfonyl chloride to a solution of the N-oxide of Formula XXII in a suitable solvent such as 1,2-dichloroethane at elevated temperature. The reaction may be carried out by adding ammonium hydroxide and p-toluenesulfonyl chloride to the reaction mixture from step (7) without isolating the N-oxide of Formula XXII Alternatively step (8) can be carried out by the reaction of a benzyloxy-thiazolo[4,5-c]quinoline-5N-oxide of Formula XXII with trichloroacetyl isocyanate followed by hydrolysis of the resulting intermediate to provide a benzyloxy-thiazolo[4,5-c]quinoline-4-amine of Formula XXIII. The reaction is conveniently carried out in two steps by (i) adding trichloroacetyl isocyanate to a solution of the N-oxide of Formula XXII in a solvent such as dichloromethane and stirring at ambient temperature to provide an isolable amide intermediate. In step (ii), a solution of the intermediate in methanol is treated with a base such as sodium methoxide or ammonium hydroxide at ambient temperature.

In step (9) of Reaction Scheme I, the benzyl group of a benzyloxy-thiazolo[4,5-c]quinoline-4-amine of Formula XXIII is cleaved to provide a thiazolo[4,5-c]quinolinol of Formula XXIV. The cleavage is conveniently carried out with an acid such as hydrogen bromide in a suitable solvent such as acetic acid at elevated temperature.

Alternatively, the cleavage may be carried out on a Parr apparatus under hydrogenolysis conditions using a suitable heterogeneous catalyst such as palladium on carbon in a solvent such as ethanol.

In step (10) of Reaction Scheme I, a thiazolo[4,5-c]quinolinol of Formula XXIV is converted to an ether-substituted thiazolo[4,5-c]quinoline-4-amine of Formula XXV using a Williamson-type ether synthesis. The reaction is effected by treating a thiazolo[4,5-c]quinolinol of Formula XXIV with an alkyl or aryl halide of Formula Halide-Z—Ar or Halide-Z—Ar'—Y—$R_4$ in the presence of a base. Numerous reagents of Formulae Halide-Z—Ar and Halide-Z—Ar'—Y—$R_4$ are commercially available, including substituted benzyl bromides and chlorides, substituted or unsubstituted arylalkylenyl bromides and chlorides, and substituted fluorobenzenes. Other reagents of Formulae Halide-Z—Ar and Halide-Z—Ar'—Y—$R_4$ can be prepared using conventional synthetic methods. The reaction is conveniently carried out by combining a reagent of Formula Halide-Z—Ar or Halide-Z—Ar'—Y—$R_4$ with a thiazolo[4,5-c]quinolinol of Formula XXIV in a solvent such as N,N-dimethylformamide (DMF) in the presence of a suitable base such as cesium carbonate. Optionally, catalytic tetrabutylammonium bromide can be added. The reaction can be carried out at ambient temperature or at an elevated temperature, for example 65° C. or 85° C., depending on the reactivity of the reagent of Formula Halide-Z—Ar or Halide-Z—Ar'—Y—$R_4$. The product or pharmaceutically acceptable salt thereof can be isolated using conventional methods.

Alternatively, step (10) may be carried out using the Ullmann ether synthesis, in which an alkali metal aryloxide of a thiazolo[4,5-c]quinolinol of Formula XXIV reacts with an aryl halide in the presence of copper salts, to provide compounds of Formula XXV, where $R_{3a}$ is —Z—Ar or —Z—Ar'—Y—$R_4$, and Z is a bond.

Reaction Scheme I

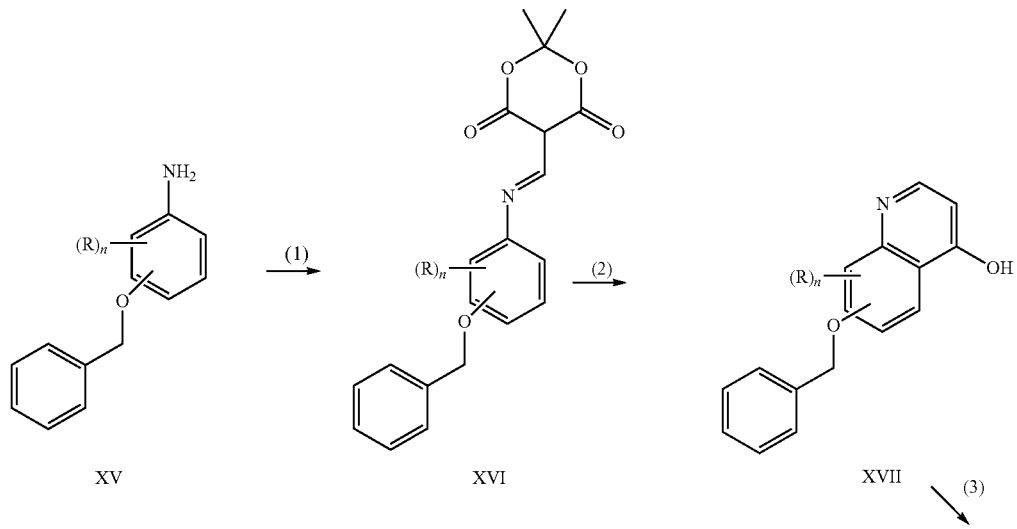

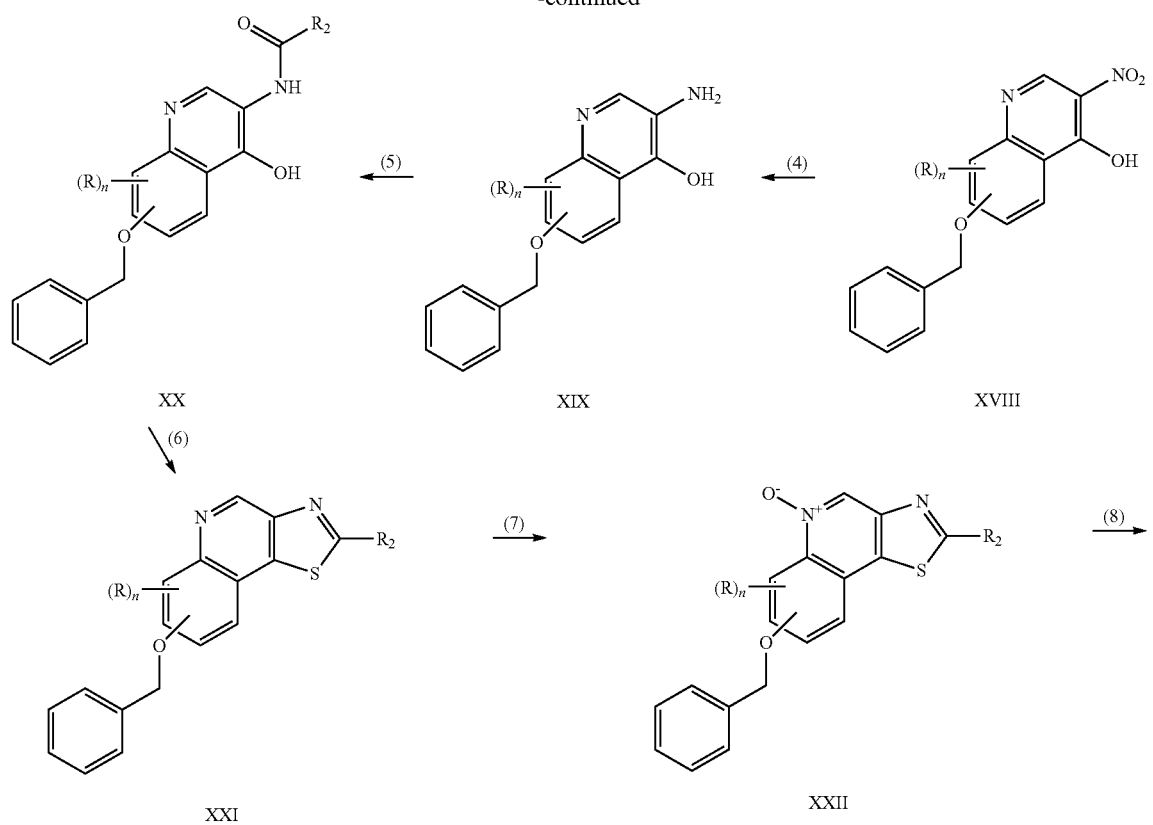
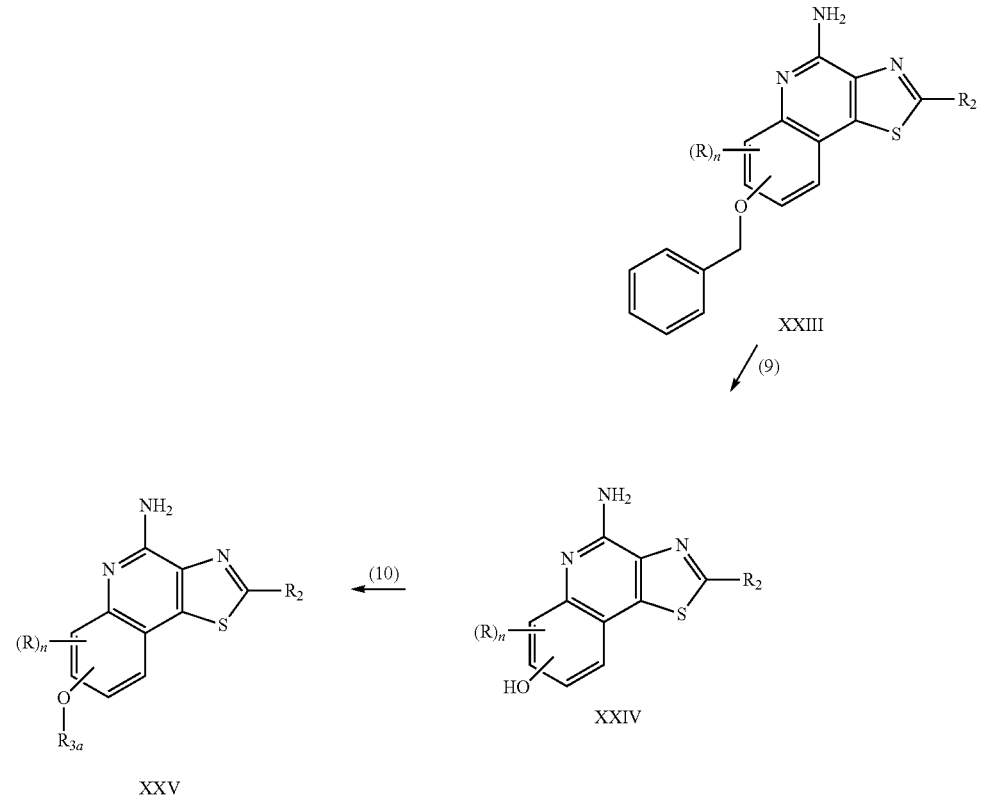

Compounds of the invention can also be prepared according to Reaction Scheme II, where R, $R_2$, and n are as defined above and $R_{3a}$ is —Z—Ar or —Z—Ar'—Y—$R_4$, where Z, Ar, Ar', Y, and $R_4$ are as defined above. In step (1) of Reaction Scheme II, the benzyl group of a benzyloxy-thiazolo[4,5-c]

substituent on the aryl or heteroaryl group on a compound of Formula II, where $R_{3a}$ is —Z—Ar, can be reduced to an amino group using conventional methods. The reduction can be carried out using the methods described in step (4) of Reaction Scheme I.

Reaction Scheme II

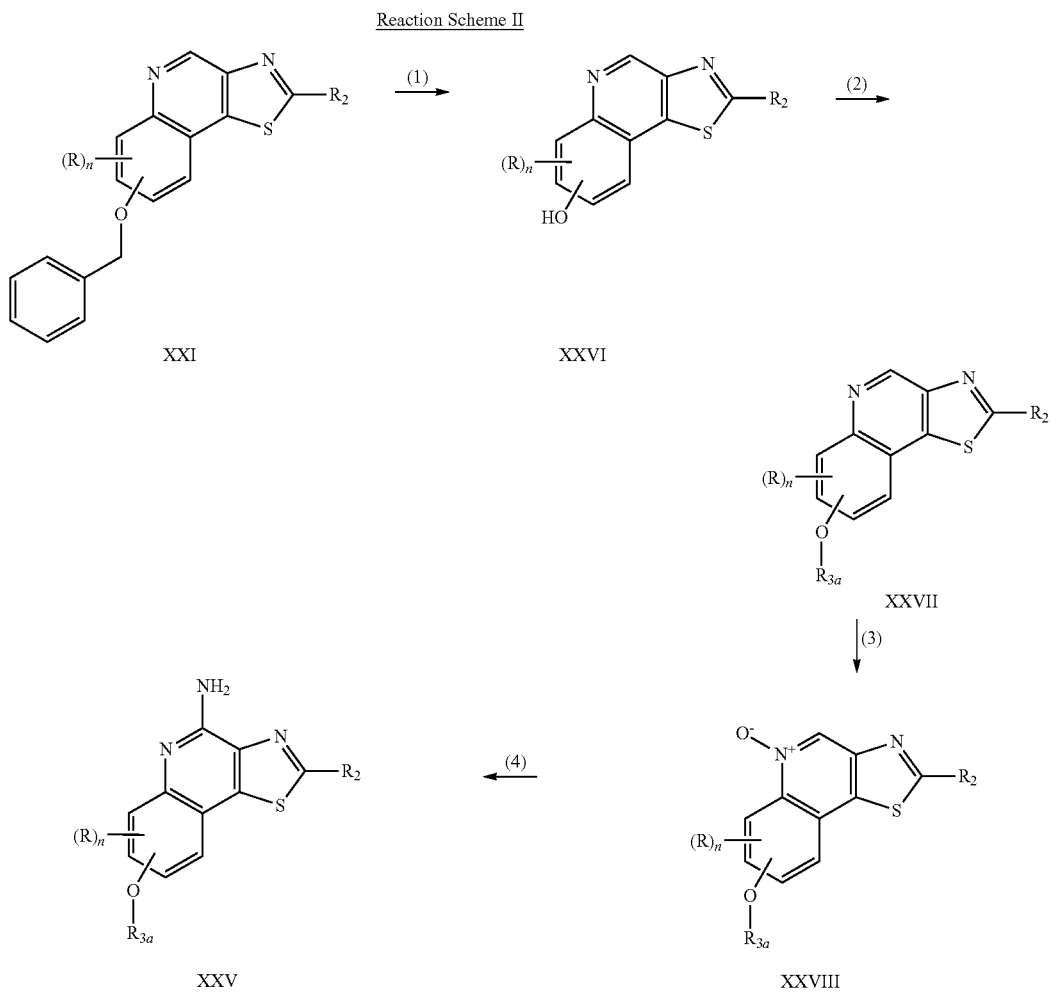

quinoline of Formula XXI is cleaved to provide a thiazolo[4,5-c]quinolinol of Formula XXVI. The reaction can be carried out as described in step (9) of Reaction Scheme I.

In step (2) of Reaction Scheme II, a thiazolo[4,5-c]quinolinol of Formula XXVI is treated with an alkyl or aryl halide of Formula Halide-Z—Ar or Halide-Z—Ar'—Y—$R_4$ to afford an ether-substituted thiazolo[4,5-c]quinoline of Formula XXVII. The reaction can be carried out as described in step (10) of Reaction Scheme I.

In steps 3 and 4 of Reaction Scheme II, an ether-substituted thiazolo[4,5-c]quinoline of Formula XXVII is oxidized to afford a thiazolo[4,5-c]quinoline-5N-oxide of Formula XXVIII, which is aminated to provide a thiazolo[4,5-c]quinolin-4-amine of Formula XXV. Steps (3) and (4) can be carried out as described in steps (7) and (8), respectively, of Reaction Scheme I. The product or pharmaceutically acceptable salt thereof can be isolated using conventional methods.

Further synthetic elaboration of ether-substituted thiazolo[4,5-c]quinolin-4-amines of Formula XXV, prepared in Reaction Scheme I or II, is possible. For example, a nitro Compounds of the invention can also be prepared according to Reaction Scheme III where R, $R_2$, and n are as defined above and $R_{3a}$ is —Z—Ar or —Z—Ar'—Y—$R_4$, where Z, Ar, Ar', Y, and $R_4$ are as defined above. In step (1) of Reaction Scheme III, a benzyloxypyridine of Formula XXX is treated with the condensation product generated from 2,2-dimethyl-1,3-dioxane-4,6-dione (Meldrum's acid) and triethyl orthoformate to provide a dione of Formula XXXI. The reaction is conveniently carried out by adding a solution of a benzyloxypyridine of Formula XXX to a heated mixture of Meldrum's acid and triethyl orthoformate and heating the reaction at an elevated temperature such as 45° C. Benzyloxypyrdines of Formula XXX can be prepared using conventional synthetic methods; see for example, Holladay et al., *Biorg. Med. Chem. Lett.*, (8), 1998, 2797-2802.

In step (2) of Reaction Scheme III, a dione of Formula XXXI undergoes thermolysis and cyclization to provide a benzyloxy[1,5]naphthyridin-4-ol of Formula XXXII. The reaction is conveniently carried out in a heat transfer fluid such as DOWTHERM A at a temperature between 200 and 250° C.

In step (3) of Reaction Scheme III, the benzyloxy[1,5] naphthyridin-4-ol of Formula XXXII is nitrated under conventional nitration conditions to provide a benzyloxy-3-nitro [1,5]naphthyridin-4-ol of Formula XXXIII. The reaction is conveniently carried out by adding nitric acid to the benzyloxy[1,5]naphthyridin-4-ol of Formula XXXII in a suitable solvent such as propionic acid and heating the mixture at an elevated temperature such as 125° C.

In step (4) of Reaction Scheme III, a benzyloxy-3-nitro[1, 5]naphthyridin-4-ol of Formula XXXIII is reduced to provide a 3-amino-benzyloxy[1,5]naphthyridin-4-ol of Formula XXXIV. The reaction can be carried out by hydrogenation using a heterogeneous hydrogenation catalyst such as platinum on carbon. The hydrogenation is conveniently carried out in a Parr apparatus in a suitable solvent such as dimethylformamide. The reaction can be carried out at ambient temperature.

In step (5) of Reaction Scheme III, a 3-amino-benzyloxy [1,5]naphthyridin-4-ol of Formula XXXIV is reacted with a carboxylic acid or an equivalent thereof to provide an amide of Formula XXXV. Suitable equivalents to carboxylic acid include acid anhydrides and acid chlorides. The reaction is conveniently carried out by adding the acid chloride to a solution of a 3-amino-benzyloxy[1,5]naphthyridin-4-ol of Formula XXXIV in a suitable solvent such as dichloromethane or acetonitrile in the presence of a tertiary amine such as triethylamine, pyridine, or 4-dimethylaminopyridine to afford an amide. The reaction can be carried out at or below ambient temperature.

In step (6) of Reaction Scheme III, a benzyloxy-[1,5]naphthyridin-4-ol of Formula XXXV is reacted with phosphorus pentasulfide to provide a benzyloxy-thiazolo[4,5-c][1,5] naphthyridine Formula XXXVI. The reaction can be carried out by adding phosphorus pentasulfide to a solution or suspension of a compound of Formula XXXV in a suitable solvent such as pyridine and heating the resulting mixture.

In step (7) of Reaction Scheme III, a benzyloxy-thiazolo [4,5-c][1,5]naphthyridine of Formula XXXVI is oxidized to provide a benzyloxy-thiazolo[4,5-c][1,5]naphthyridine-5N-oxide of Formula XXXVII using a conventional oxidizing agent capable of forming N-oxides. The reaction is conveniently carried out by adding 3-chloroperoxybenzoic acid to a solution of a compound of Formula XXXVI in a solvent such dichloromethane or chloroform. The reaction can be carried out at ambient temperature.

In step (8) of Reaction Scheme III, a benzyloxy-thiazolo [4,5-c][1,5]naphthyridine-5N-oxide of Formula XXXVII is aminated to provide a benzyloxy-thiazolo[4,5-c][1,5-naphthyridin-4-amine of Formula XXXVIII. Step (8) can be carried out by the activation of an N-oxide of Formula XXXVII by conversion to an ester and then reacting the ester with an aminating agent. Suitable activating agents include alkyl- or arylsulfonyl chlorides such as benzenesulfonyl chloride, methanesulfonyl chloride, or p-toluenesulfonyl chloride. Suitable aminating agents include ammonia, in the form of ammonium hydroxide, for example, and ammonium salts such as ammonium carbonate, ammonium bicarbonate, and ammonium phosphate. The reaction is conveniently carried out by adding ammonium hydroxide followed by p-toluenesulfonyl chloride to a solution of the N-oxide of Formula XXXVII in a suitable solvent such as 1,2-dichloroethane at elevated temperature. The reaction may be carried out by adding ammonium hydroxide and p-toluenesulfonyl chloride to the reaction mixture from step (7) without isolating the N-oxide of Formula XXXVII.

Alternatively step (8) can be carried out by the reaction of a benzyloxy-thiazolo[4,5-c][1,5]naphthyridine-5N-oxide of Formula XXXVII with trichloroacetyl isocyanate followed by hydrolysis of the resulting intermediate to provide a benzyloxy-thiazolo[4,5-c][1,5]naphthyridin-4-amine of Formula XXXVIII. The reaction is conveniently carried out in two steps by (i) adding trichloroacetyl isocyanate to a solution of the N-oxide of Formula XXXVII in a solvent such as dichloromethane and stirring at ambient temperature to provide an isolable amide intermediate. In step (ii), a solution of the intermediate in methanol is treated with a base such as sodium methoxide or ammonium hydroxide at ambient temperature.

In step (9) of Reaction Scheme III, the benzyl group of a benzyloxy-thiazolo[4,5-c][1,5]naphthyridin-4-amine of Formula XXXVIII is cleaved to provide a thiazolo[4,5-c][1,5] naphthyridinol of Formula XXXIX. The cleavage is conveniently carried out with an acid such as hydrogen bromide in a suitable solvent such as acetic acid at elevated temperature.

Alternatively, the cleavage may be carried out on a Parr apparatus under hydrogenolysis conditions using a suitable heterogeneous catalyst such as palladium on carbon in a solvent such as ethanol.

In step (10) of Reaction Scheme III a thiazolo[4,5-c][1,5] naphthyridinol of Formula XXXIX is converted to an ether-substituted thiazolo[4,5-c][1,5]naphthyridin-4-amine of Formula XXXX using a Williamson-type ether synthesis. The reaction is effected by treating a thiazolo[4,5-c][1,5]naphthyridinol of Formula XXXIX with an alkyl or aryl halide of Formula Halide-Z—Ar or Halide-Z—Ar'—Y—R$_4$ in the presence of a base. Numerous reagents of Formulae Halide-Z—Ar and Halide-Z—Ar'—Y—R$_4$ are commercially available, including substituted benzyl bromides and chlorides, substituted or unsubstituted arylalkylenyl bromides and chlorides, and substituted fluorobenzenes. Other reagents of Formulae Halide-Z—Ar and Halide-Z—Ar'—Y—R$_4$ can be prepared using conventional synthetic methods. The reaction is conveniently carried out by combining a reagent of Formula Halide-Z—Ar or Halide-Z—Ar'—Y—R$_4$ with a thiazolo[4, 5-c][1,5]naphthyridinol of Formula XXXIX in a solvent such as DMF in the presence of a suitable base such as cesium carbonate. Optionally, catalytic tetrabutylammonium bromide can be added. The reaction can be carried out at ambient temperature or at an elevated temperature, for example 65° C. or 85° C., depending on the reactivity of the reagent of Formula Halide-Z—Ar or Halide-Z—Ar'—Y—R$_4$. The product or pharmaceutically acceptable salt thereof can be isolated using conventional methods.

Alternatively, step (10) may be carried out using the Ullmann ether synthesis, in which an alkali metal aryloxide of a thiazolo[4,5-c][1,5]naphthyridinol of Formula XXXIX reacts with an aryl halide in the presence of copper salts, to provide compounds of Formula XXXX, where R$_3$ is —Z—Ar or —Z—Ar'—Y—R$_4$, and Z is a bond.

Reaction Scheme III
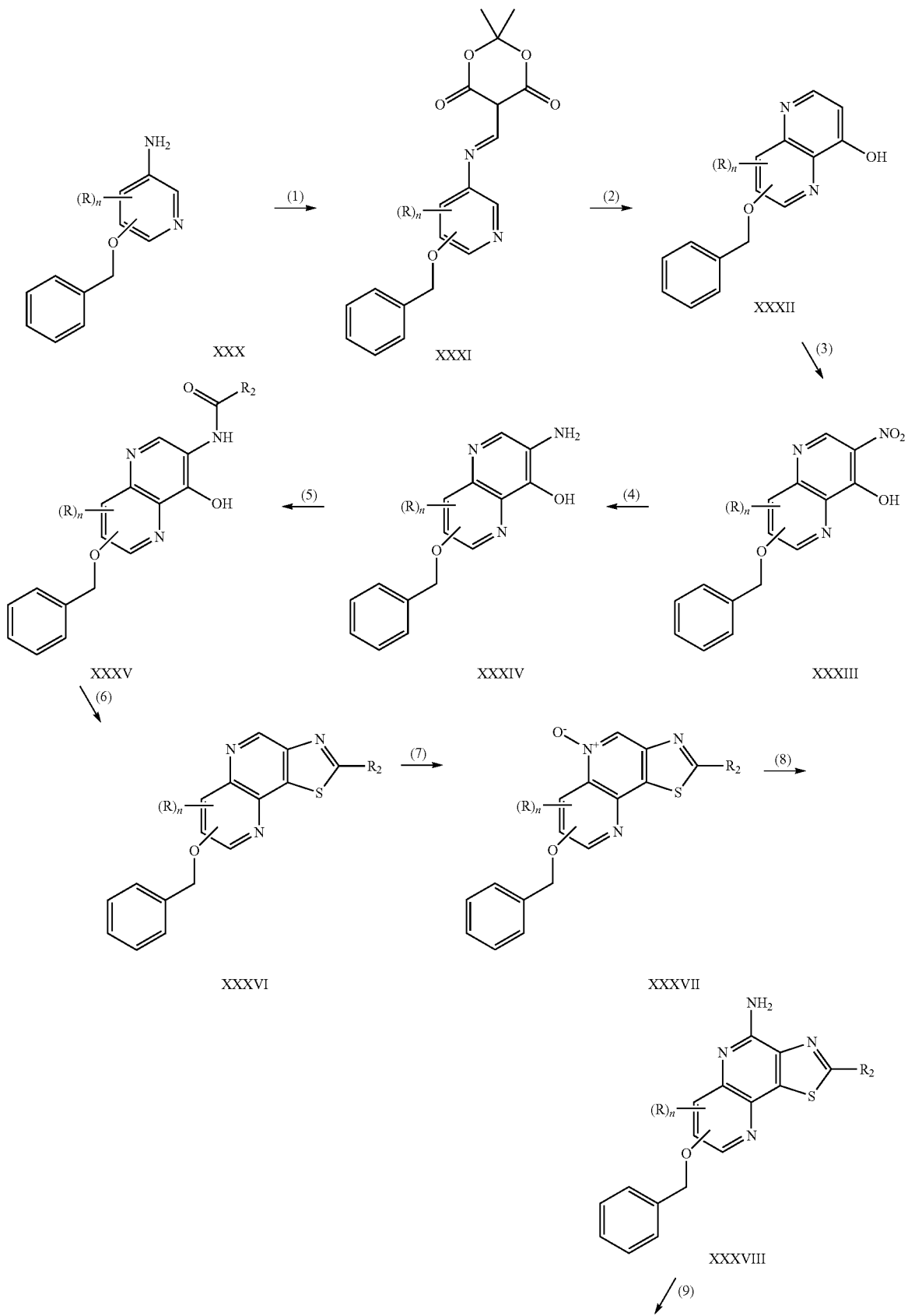

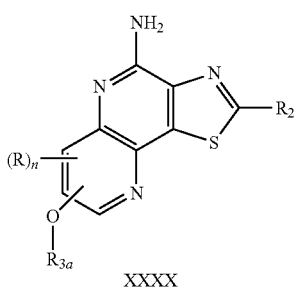

XXXX

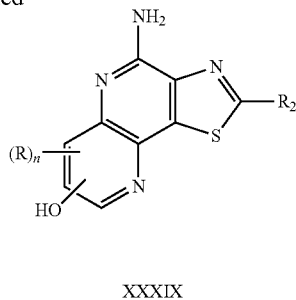

XXXIX

Compounds of the invention can also be prepared using the synthetic routes described in the EXAMPLES below.

Prodrugs can be prepared in a variety of ways. For example, a compound wherein $R_2$ is hydroxyalkylenyl can be converted into a prodrug wherein $R_2$ is, for example, -alkylenyl-O—C($R_6$)—$R_4$, -alkylenyl-O—C($R_6$)—O—$R_4$, or -alkylenyl-O—C($R_6$)—N($R_8$)—$R_4$, wherein $R_4$, $R_6$, and $R_8$ are as defined above, using methods known to one skilled in the art. In addition, a compound wherein Ar is substituted by hydroxy or a hydroxyalkylenyl group may also be converted to an ester, an ether, a carbonate, or a carbamate. For any of these compounds containing an alcohol functional group, a prodrug can be formed by the replacement of the hydrogen atom of the alcohol group with a group such as $C_{1-6}$alkanoyloxymethyl, 1-($C_{1-6}$alkanoyloxy)ethyl, 1-methyl-1-($C_{1-6}$alkanoyloxy)ethyl, $C_{1-6}$ alkoxycarbonyloxymethyl, N—($C_{1-6}$ alkoxycarbonyl)aminomethyl, succinoyl, $C_{1-6}$ alkanoyl, α-amino$C_{1-4}$ alkanoyl, arylacyl, —P(O)(OH)$_2$, —P(O)(O—$C_{1-6}$alkyl)$_2$, $C_{1-6}$alkoxycarbonyl, $C_{1-6}$ alkylcarbamoyl, and α-aminoacyl or α-aminoacyl-α-aminoacyl, where each α-aminoacyl group is independently selected from racemic, D-, and L-amino acids. For compounds containing an alcohol functional group, particularly useful prodrugs are esters made from carboxylic acids containing one to six carbon atoms, unsubstituted or substituted benzoic acid esters, or esters made from racemic, D-, or L-amino acids.

Prodrugs can also be made from a compound containing an amino group by conversion of the amino group to a functional group such as an amide, carbamate, urea, amidine, or another hydrolysable group using conventional methods. A prodrug of this type can be made by the replacement of a hydrogen atom in an amino group, particularly the amino group at the 4-position, with a group such as —C(O)—R', α-aminoacyl, α-aminoacyl-α-aminoacyl, —C(O)—O—R', —C(O)—N(R")—R', —CH(OH)—C(O)—OY', —CH(O$C_{1-4}$ alkyl)Y$_0$, —CH$_2$Y$_1$, or —CH(CH$_3$)Y$_1$; wherein R' and R" are each independently $C_{1-10}$ alkyl, $C_{3-7}$ cycloalkyl, or benzyl, each of which may be unsubstituted or substituted by one or more substituents selected from the group consisting of halogen, hydroxy, nitro, cyano, carboxy, $C_{1-6}$ alkyl, $C_{1-4}$ alkoxy, aryl, heteroaryl, aryl$C_{1-4}$ alkylenyl, heteroaryl$C_{1-4}$ alkylenyl, halo$C_{1-4}$ alkylenyl, halo$C_{1-4}$ alkoxy, —O—C(O)—CH$_3$, —C(O)—O—CH$_3$, —C(O)—NH$_2$, —O—CH$_2$—C(O)—NH$_2$, —NH$_2$, and —S(O)$_2$—NH$_2$, with the proviso that R" can also be hydrogen; each α-aminoacyl group is independently selected from racemic, D-, and L-amino acids; Y' is hydrogen, $C_{1-6}$ alkyl, or benzyl; Y$_0$ is $C_{1-6}$ alkyl, carboxy$C_{1-6}$ alkylenyl, amino$C_{1-4}$ alkylenyl, mono-N—$C_{1-6}$alkylamino$C_{1-4}$ alkylenyl, or di-N,N—$C_{1-6}$alkylamino$C_{1-4}$ alkylenyl; and Y$_1$ is mono-N—$C_{1-6}$ alkylamino, di-N,N—$C_{1-6}$alkylamino, morpholin-4-yl, piperidin-1-yl, pyrrolidin-1-yl, or 4-$C_{1-4}$ alkylpiperazin-1-yl.

Pharmaceutical Compositions and Biological Activity

Pharmaceutical compositions of the invention contain a therapeutically effective amount of a compound or salt of the invention as described above in combination with a pharmaceutically acceptable carrier.

The terms "a therapeutically effective amount" and "effective amount" mean an amount of the compound or salt sufficient to induce a therapeutic or prophylactic effect, such as cytokine induction, immunomodulation, antitumor activity, and/or antiviral activity. Although the exact amount of active compound or salt used in a pharmaceutical composition of the invention will vary according to factors known to those of skill in the art, such as the physical and chemical nature of the compound or salt, the nature of the carrier, and the intended dosing regimen, it is anticipated that the compositions of the invention will contain sufficient active ingredient to provide a dose of about 100 nanograms per kilogram (ng/kg) to about 50 milligrams per kilogram (mg/kg), preferably about 10 micrograms per kilogram (μg/kg) to about 5 mg/kg, of the compound or salt to the subject. A variety of dosage forms may be used, such as tablets, lozenges, capsules, parenteral formulations, syrups, creams, ointments, aerosol formulations, transdermal patches, transmucosal patches and the like.

The compounds or salts of the invention can be administered as the single therapeutic agent in the treatment regimen, or the compounds or salts of the invention may be administered in combination with one another or with other active agents, including additional immune response modifiers, antivirals, antibiotics, antibodies, proteins, peptides, oligonucleotides, etc.

Compounds or salts of the invention have been shown to induce, and certain compounds or salts of the invention may inhibit, the production of certain cytokines in experiments performed according to the tests set forth below. These results indicate that the compounds or salts are useful as immune response modifiers that can modulate the immune response in a number of different ways, rendering them useful in the treatment of a variety of disorders.

Cytokines whose production may be induced by the administration of compounds or salts of the invention generally include interferon-α (IFN-α) and/or tumor necrosis factor-α (TNF-α) as well as certain interleukins (IL). Cytokines whose biosynthesis may be induced by compounds or salts of the invention include IFN-α, TNF-α, IL-1, IL-6, IL-10 and IL-12, and a variety of other cytokines. Among other effects, these and other cytokines can inhibit virus production and tumor cell growth, making the compounds or salts useful in the treatment of viral diseases and neoplastic diseases. Accordingly, the invention provides a method of inducing cytokine biosynthesis in an animal comprising administering an effective amount of a compound or salt or composition of the invention to the animal. The animal to which the compound or salt or composition is administered for induction of cytokine biosynthesis may have a disease as described infra, for example a viral disease or a neoplastic disease, and administration of the compound or salt may provide therapeutic treatment. Alternatively, the compound or salt may be administered to the animal prior to the animal acquiring the disease so that administration of the compound or salt may provide a prophylactic treatment.

In addition to the ability to induce the production of cytokines, compounds or salts of the invention can affect other aspects of the innate immune response. For example, natural killer cell activity may be stimulated, an effect that may be due to cytokine induction. The compounds or salts may also activate macrophages, which in turn stimulate secretion of nitric oxide and the production of additional cytokines. Further, the compounds or salts may cause proliferation and differentiation of B-lymphocytes.

Compounds or salts of the invention can also have an effect on the acquired immune response. For example, the production of the T helper type 1 ($T_H1$) cytokine IFN-γ may be induced indirectly and the production of the T helper type 2 ($T_H2$) cytokines IL-4, IL-5 and IL-13 may be inhibited upon administration of the compounds or salts.

Other cytokines whose production may be inhibited by the administration of compounds or salts of the invention include tumor necrosis factor-α (TNF-α). Among other effects, inhibition of TNF-α production can provide prophylaxis or therapeutic treatment of TNF-α mediated diseases in animals, making the compounds or salt useful in the treatment of, for example, autoimmune diseases. Accordingly, the invention provides a method of inhibiting TNF-α biosynthesis in an animal comprising administering an effective amount of a compound or salt or composition of the invention to the animal. The animal to which the compound or salt or composition is administered for inhibition of TNF-α biosynthesis may have a disease as described infra, for example an autoimmune disease, and administration of the compound or salt may provide therapeutic treatment. Alternatively, the compound or salt may be administered to the animal prior to the animal acquiring the disease so that administration of the compound or salt may provide a prophylactic treatment.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt and other component or components may be administered separately; together but independently such as in a solution; or together and associated with one another such as (a) covalently linked or (b) non-covalently associated, e.g., in a colloidal suspension.

Conditions for which compounds or salts identified herein may be used as treatments include, but are not limited to:

(a) viral diseases such as, for example, diseases resulting from infection by an adenovirus, a herpesvirus (e.g., HSV-I, HSV-II, CMV, or VZV), a poxvirus (e.g., an orthopoxvirus such as variola or vaccinia, or molluscum contagiosum), a picornavirus (e.g., rhinovirus or enterovirus), an orthomyxovirus (e.g., influenzavirus), a paramyxovirus (e.g., parainfluenzavirus, mumps virus, measles virus, and respiratory syncytial virus (RSV)), a coronavirus (e.g., SARS), a papovavirus (e.g., papillomaviruses, such as those that cause genital warts, common warts, or plantar warts), a hepadnavirus (e.g., hepatitis B virus), a flavivirus (e.g., hepatitis C virus or Dengue virus), or a retrovirus (e.g., a lentivirus such as HIV);

(b) bacterial diseases such as, for example, diseases resulting from infection by bacteria of, for example, the genus *Escherichia, Enterobacter, Salmonella, Staphylococcus, Shigella, Listeria, Aerobacter, Helicobacter, Klebsiella, Proteus, Pseudomonas, Streptococcus, Chlamydia, Mycoplasma, Pneumococcus, Neisseria, Clostridium, Bacillus, Corynebacterium, Mycobacterium, Campylobacter, Vibrio, Serratia, Providencia, Chromobacterium, Brucella, Yersinia, Haemophilus,* or *Bordetella;*

(c) other infectious diseases, such chlamydia, fungal diseases including but not limited to candidiasis, aspergillosis, histoplasmosis, cryptococcal meningitis, or parasitic diseases including but not limited to malaria, *pneumocystis carnii* pneumonia, leishmaniasis, cryptosporidiosis, toxoplasmosis, and trypanosome infection;

(d) neoplastic diseases, such as intraepithelial neoplasias, cervical dysplasia, actinic keratosis, basal cell carcinoma, squamous cell carcinoma, renal cell carcinoma, Kaposi's sarcoma, melanoma, leukemias including but not limited to myelogeous leukemia, chronic lymphocytic leukemia, multiple myeloma, non-Hodgkin's lymphoma, cutaneous T-cell lymphoma, B-cell lymphoma, and hairy cell leukemia, and other cancers;

(e) $T_H2$-mediated, atopic diseases, such as atopic dermatitis or eczema, eosinophilia, asthma, allergy, allergic rhinitis, and Ommen's syndrome;

(f) certain autoimmune diseases such as systemic lupus erythematosus, essential thrombocythaemia, multiple sclerosis, discoid lupus, alopecia areata; and (g) diseases associated with wound repair such as, for example, inhibition of keloid formation and other types of scarring (e.g., enhancing wound healing, including chronic wounds).

Additionally, a compound or salt of the present invention may be useful as a vaccine adjuvant for use in conjunction with any material that raises either humoral and/or cell mediated immune response, such as, for example, live viral, bacterial, or parasitic immunogens; inactivated viral, tumor-derived, protozoal, organism-derived, fungal, or bacterial immunogens; toxoids; toxins; self-antigens; polysaccharides; proteins; glycoproteins; peptides; cellular vaccines; DNA vaccines; autologous vaccines; recombinant proteins; and the like, for use in connection with, for example, BCG, cholera, plague, typhoid, hepatitis A, hepatitis B, hepatitis C, influenza A, influenza B, parainfluenza, polio, rabies, measles, mumps, rubella, yellow fever, tetanus, diphtheria, hemophilus influenza b, tuberculosis, meningococcal and pneumococcal vaccines, adenovirus, HIV, chicken pox, cytomegalovirus, dengue, feline leukemia, fowl plague, HSV-1 and HSV-2, hog cholera, Japanese encephalitis, respiratory syncytial virus, rotavirus, papilloma virus, yellow fever, and Alzheimer's Disease.

Compounds or salts of the present invention may be particularly helpful in individuals having compromised immune function. For example, compounds or salts may be used for treating the opportunistic infections and tumors that occur after suppression of cell mediated immunity in, for example, transplant patients, cancer patients and HIV patients.

Thus, one or more of the above diseases or types of diseases, for example, a viral disease or a neoplastic disease may be treated in an animal in need thereof (having the disease) by administering a therapeutically effective amount of a compound or salt of the invention to the animal.

An amount of a compound or salt effective to induce or inhibit cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased (induced) or decreased (inhibited) over a background level of such cytokines. The precise amount will vary according to factors known in the art but is expected to be a dose of about 100 ng/kg to about 50 mg/kg, preferably about 10 μg/kg to about 5 mg/kg. The invention also provides a method of treating a viral infection in an animal and a method of treating a neoplastic disease in an animal comprising administering an effective amount of a compound or salt or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount that is effective for such treatment will vary according to factors known in the art but is expected to be a dose of about 100 ng/kg to about 50 mg/kg, preferably about 10 μg/kg to about 5 mg/kg. An amount of a compound or salt effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 μg/kg to about 5 mg/kg.

In addition to the formulations and uses described specifically herein, other formulations, uses, and administration devices suitable for compounds of the present invention are described in, for example, International Publication Nos. WO 03/077944 and WO 02/036592, U.S. Pat. No. 6,245,776, and U.S. Publication Nos. 2003/0139364, 2003/185835, 2004/0258698, 2004/0265351, 2004/076633, and 2005/0009858.

EXAMPLES

Objects and advantages of this invention are further illustrated by the following examples, but the particular materials and amounts thereof recited in these examples, as well as other conditions and details, should not be construed to unduly limit this invention.

Example 1

7-Benzyloxy-2-propylthiazolo[4,5-c]quinolin-4-amine

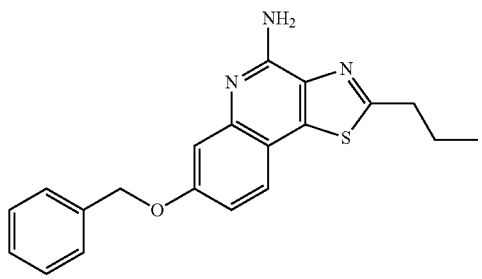

Part A

A mixture of triethyl orthoformate (92 mL, 0.55 mol) and 2,2-dimethyl-[1,3]-dioxane-4,6-dione (75.3 g, 0.522 mol) (Meldrum's acid) was heated at 55° C. for 90 minutes and then cooled to 45° C. A solution of 3-benzyloxyaniline (100.2 g, 0.5029 mol) in methanol (200 mL) was slowly added to the reaction over a period 45 minutes while maintaining the reaction temperature below 50° C. The reaction was then heated at 45° C. for one hour, allowed to cool to room temperature, and stirred overnight. The reaction mixture was cooled to 1° C., and the product was isolated by filtration and washed with cold ethanol (~400 mL) until the filtrate was colorless. 5-{[(3-Benzyloxy)phenylimino]methyl}-2,2-dimethyl-[1,3]-dioxane-4,6-dione (170.65 g) was isolated as a tan, powdery solid. $^1$H NMR (300 MHz, DMSO-$d_6$) δ 11.21 (d, J=14.2 Hz, 1H), 8.61 (d, J=14.2 Hz, 1H), 7.49-7.30 (m, 7H), 7.12 (dd, J=8.1, 1.96 Hz, 1H), 6.91 (dd, J=8.4, 2.1 Hz, 1H), 5.16 (s, 2H), 1.68 (s, 6H).

Part B

A mixture of 5-{[(3-benzyloxy)phenylimino]methyl}-2,2-dimethyl-[1,3]-dioxane-4,6-dione (170.65 g, 0.483 mol) and DOWTHERM A (800 mL) was heated to 100° C. and then slowly added to a flask containing DOWTHERM A (1.3 L, heated at 210° C.) over a period of 40 minutes. During the addition, the reaction temperature was not allowed to fall below 207° C. Following the addition, the reaction was stirred at 210° C. for one hour, and then allowed to cool to ambient temperature. A precipitate formed, which was isolated by filtration, washed with diethyl ether (1.7 L) and acetone (0.5 L), and dried in an oven to provide 76.5 g of 7-benzyloxyquinolin-4-ol as a tan powder. $^1$H NMR (300 MHz, DMSO-$d_6$) δ 11.53 (s, 1H), 7.99 (dd, J=2.4, 7.4 Hz, 1H), 7.79 (d, J=7.4 Hz, 1H), 7.50-7.32 (m, 5H), 7.00 (s, 1H), 6.98 (dd, J=2.5, 7.4 Hz, 1H), 5.93 (d, J=7.5 Hz, 1H), 5.20 (s, 2H).

Part C

A mixture of 7-benzyloxyquinolin-4-ol (71.47 g, 0.2844 mol) and propionic acid (700 mL) was heated to 125° C. with vigorous stirring. Nitric acid (23.11 mL of 16 M) was slowly added over a period of 30 minutes while maintaining the reaction temperature between 121° C. and 125° C. After the addition, the reaction was stirred at 125° C. for 1 hour then allowed to cool to ambient temperature. The resulting solid was isolated by filtration, washed with water, and dried in an oven for 1.5 days to provide 69.13 g of 7-benzyloxy-3-nitroquinolin-4-ol as a grayish powder. $^1$H NMR (300 MHz, DMSO-$d_6$) δ 12.77 (s, 1H), 9.12 (s, 1H), 8.17 (dd, J=3.3, 6.3 Hz, 1H), 7.51-7.33 (m, 5H), 7.21-7.17 (m, 2H), 5.25 (s, 2H).

Part D

A mixture of 7-benzyloxy-3-nitroquinolin-4-ol (10.67 g, 36.0 mmol) and 5% platinum on carbon (1.05 g) in N,N-dimethylformamide (DMF, 110 mL) was hydrogenated on a Parr apparatus. The mixture was filtered through CELITE filter agent. The CELITE filter agent was rinsed with DMF (20 mL). The filtrate was cooled in an ice bath and acidified with hydrogen chloride gas, resulting in the formation of a reddish-brown solid. The solid was isolated by filtration, washed with acetone, and dried in a vacuum oven at 60° C. to provide 3-amino-7-benzyloxyquinolin-4-ol hydrochloride as a tan solid (8.17 g, 75%).

Part E

To a solution of the crude 3-amino-7-benzyloxyquinolin-4-ol hydrochloride (8.03 g, 26.5 mmol) prepared in Part D and triethylamine (7.40 mL, 53 mmol) in dichloromethane at 0° C. was added butyryl chloride (2.75 mL, 26.5 mmol) dropwise via syringe. The solution was stirred at 0° C. for 10 minutes (min), then the cooling bath was removed. A solid formed that was isolated by filtration and washed with a small amount of dichloromethane. The solid was slurried with water (75 mL) and was isolated by filtration. The solid was rinsed with water followed by ether, then dried at 60° C. in a vacuum oven to provide 8.03 g (90%) of the crude product, N-(7-benzyloxy-4-hydroxyquinolin-3-yl)butyramide, which was contaminated with a salt of triethylamine as determined by $^1$H NMR analysis.

Part F

A mixture of the N-(7-benzyloxy-4-hydroxyquinolin-3-yl) butyramide prepared in Part E (2.97 g, 8.83 mmol), $P_2S_5$ (1.96 g, 4.41 mmol), and pyridine was placed under a nitrogen atmosphere and heated to reflux. The resulting solution was cooled and the excess $P_2S_5$ was quenched slowly with 10% aqueous $Na_2CO_3$ (10 mL). The reaction mixture was partitioned between water (40 mL) and $CH_2Cl_2$ (100 mL). The organic layer was washed with 0.1 M aqueous HCl (50 mL), dried over $MgSO_4$, filtered and concentrated to yield a brownish-yellow solid. The solid was treated with boiling heptane (40 mL) and filtered. The filtrate was allowed to cool and a solid formed. The light yellow solid was isolated by filtration and washed with cold heptane to provide 7-benzyloxy-2-propylthiazolo[4,5-c]quinoline (1.74 g, 59%).

Part G

To a solution of 7-benzyloxy-2-propylthiazolo[4,5-c]quinoline (4.89 g, 14.6 mmol) in $CH_2Cl_2$ (75 mL) at room temperature (rt) was added 3-chloroperoxybenzoic acid (m-CPBA, 65% w/w, 5.82 g, 21.93 mmol) in portions. After one hour (h), the mixture was transferred to a separatory funnel and washed with 10% aqueous $Na_2CO_3$ (2×50 mL). The aqueous layer was extracted with $CH_2Cl_2$ (50 mL). The combined organic layers were washed with water (75 mL), dried over $MgSO_4$, filtered, concentrated, and dried under high vacuum to yield 7-benzyloxy-2-propylthiazolo[4,5-c]quinoline-5N-oxide as a light yellow solid (4.93 g, 96%).

Part H

To a light orange solution of 7-benzyloxy-2-propylthiazolo[4,5-c]quinoline-5N-oxide (4.93 g, 14.1 mmol) in $CH_2Cl_2$ (100 mL) at 0° C. was added trichloroacetylisocyanate (2.00 mL, 16.9 mmol). The solution was allowed to warm to rt and was stirred 20 h. The solution was concentrated in vacuo, and the resulting residue N-(7-benzyloxy-2-propylthiazolo[4,5-c]quinolin-4-yl)-2,2,2-trichloroacetamide was used without further manipulation in the next step.

Part I

To a magnetically stirred mixture of N-(7-benzyloxy-2-propylthiazolo[4,5-c]quinolin-4-yl)-2,2,2-trichloroacetamide (prepared as described above in Part H, 6.96 g, 14.9 mmol) in methanol (100 mL) at rt was added NaOMe (25 wt. % solution in MeOH, 11.3 mL, 52.1 mmol). After a few minutes a solution formed from which a solid precipitated. The reaction mixture was concentrated in vacuo and dried under vacuum. The resulting solid was suspended in a minimal amount of methanol (50 mL) and was isolated by filtration. The solid was washed with methanol to provide 7-benzyloxy-2-propylthiazolo[4,5-c]quinolin-4-amine as a light yellow solid in high purity (3.93 g, 76%), mp 175-178° C. $^1$H NMR (300 MHz, $d_6$-DMSO) δ 7.67 (d, J=8.7 Hz, 1H), 7.49-7.29 (m, 5H), 7.10 (d, J=2.5 Hz, 1H), 6.96 (dd, J=8.7, 2.5 Hz, 1H), 6.84 (s, 2H), 5.20 (s, 2H), 3.09 (t, J=7.8 Hz, 2H), 1.84 (sextet, J=7.2 Hz, 2H), 0.99 (t, J=7.5 Hz, 3H); $^{13}$C NMR (75 MHz, $d_6$-DMSO) δ 169.1, 158.9, 152.4, 146.5, 139.4, 137.0, 136.0, 128.4, 127.8, 127.6, 125.7, 113.3, 113.2, 107.8, 69.3, 35.1, 22.8, 13.5. MS (APCI) m/z=350.0 (M+H) % Anal. calcd for $C_{20}H_{19}N_3OS$: C, 68.74; H, 5.48; N, 12.02. Found: C, 68.62; H, 5.74; N, 11.94.

Example 2

7-(4-Fluorobenzyloxy)-2-propylthiazolo[4,5-c]quinolin-4-amine

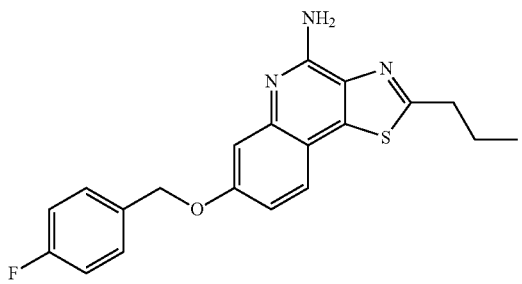

Part A

To 7-benzyloxy-2-propylthiazolo[4,5-c]quinoline (prepared as described in Part F of Example 1, 4.52 g, 13.5 mmol) was added a 45 wt. % solution of hydrogen bromide in acetic acid (40 mL). The resulting solution was heated at 65° C. for 1.5 h, then cooled in an ice bath. Aqueous NaOH (50% w/w solution) was added slowly until the pH=7 and a light yellow solid formed. The solid was isolated by filtration, dried, and then suspended in boiling ethanol (25 mL) for 5 min. The mixture was allowed to cool to rt and a tan solid was isolated by filtration. The solid was washed with cold ethanol and dried in a vacuum oven to yield 7-hydroxy-2-propylthiazolo[4,5-c]quinoline (2.69 g, 82%).

Part B

A mixture of 7-hydroxy-2-propylthiazolo[4,5-c]quinoline (0.88 g, 3.6 mmol) and cesium carbonate (2.35 g, 7.20 mmol) in DMF (50 mL) was stirred for 30 min, then 4-fluorobenzylbromide (0.50 mL, 4.0 mmol) was added. After 2 h, the mixture was concentrated in vacuo to remove the DMF. The resulting solid was partitioned between dichloromethane (100 mL) and water (100 mL). The organic layer was washed with water (50 mL) and brine (50 mL), dried over $MgSO_4$, filtered, and concentrated to a light yellow solid. The solid was recrystallized from heptane and pure 7-(4-fluorobenzyloxy)-2-propylthiazolo[4,5-c]quinoline was isolated as a tan solid (0.86 g, 68%).

Part C 7-(4-Fluorobenzyloxy)-2-propylthiazolo[4,5-c]quinoline (0.84 g, 2.38 mmol) was treated with m-CPBA (65% w/w, 0.95 g, 3.58 mmol) according to the method described in Part G of Example 1 to yield 7-(4-fluorobenzyloxy)-2-propylthiazolo[4,5-c]quinoline-5N-oxide as a light yellow solid (0.81 g, 92%).

Part D

To a solution of 7-(4-fluorobenzyloxy)-2-propylthiazolo[4,5-c]quinoline-5N-oxide (0.81 g, 2.2 mmol) in 1,2-dichloroethane at 65° C. in a glass heavy wall pressure vessel was added concentrated ammonium hydroxide (5 mL) and p-toluenesulfonyl chloride (0.42 g, 2.4 mmol). The vessel was sealed with a screw cap and the mixture was stirred at 65° C. for 3 h. The reaction mixture was transferred to a separatory funnel with dichloromethane (50 mL) and washed with 2 M aqueous $Na_2CO_3$ (2×50 mL). The combined aqueous layers were extracted with dichloromethane (50 mL). The organic phases were combined, washed with water (50 mL) and brine (50 mL), dried over $MgSO_4$, filtered and concentrated to yield a brown solid. The crude product was purified on a HORIZON High-Performance Flash Chromatography (HPFC) instrument (available from Biotage, Inc, Charlottesville, Va., USA) (silica gel eluting sequentially with 0-15% of a solution comprised of 80% $CHCl_3$, 18% MeOH, and 2% conc. $NH_4OH$(CMA) in chloroform). The appropriate fractions were combined and concentrated to provide a light yellow solid. The solid was crystallized from acetonitrile. The resulting white solid was isolated, washed with acetonitrile, and dried overnight at 60° C. in a vacuum oven to provide 7-(4-fluorobenzyloxy)-2-propylthiazolo[4,5-c]quinolin-4-amine (0.33 g, 41%), mp 189-192° C. NMR (300 MHz, $d_6$-DMSO) δ 7.67 (d, J=8.8 Hz, 1H), 7.55-7.50 (m, 2H), 7.26-7.18 (m, 2H), 7.10 (d, J=2.5 Hz, 1H), 6.96 (dd, J=8.8, 2.5 Hz, 1H), 6.80 (s, 2H), 5.20 (s, 2H), 3.11 (t, J=7.8 Hz, 2H), 1.84 (sextet, J=7.2 Hz, 2H), 1.00 (t, J=7.5 Hz, 3H); Anal. calcd for $C_{20}H_{18}N_3OSF$: C, 65.38; H, 4.94; N, 11.44. Found: C, 65.36; H, 4.87; N, 11.39.

Example 3

7-[2-(4-Fluorophenyl)ethoxy]-2-propylthiazolo[4,5-c]quinolin-4-amine

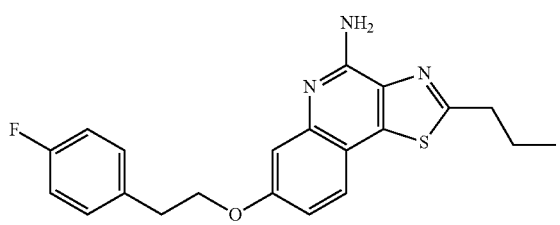

Part A

Iodine (12.0 g, 47.4 mmol) was added in one portion to a solution of 2-phenylethanol (5.11 g, 36.5 mmol), triphenylphosphine (11.47 g, 43.8 mmol) and imidazole (3.48 g, 51.04 mmol) in dichloromethane (250 mL) at 0° C. The resulting mixture was allowed to warm slowly to rt and stir overnight, then was transferred to a separatory funnel and washed with water (2×250 mL), saturated aqueous $Na_2S_2O_3$ (2×100 mL), water (100 mL), and brine (100 mL). The organic phase was dried over $MgSO_4$, filtered and concentrated to a colorless oil that contained a large amount of white solid. The mixture was treated with heptane (2×50 mL) and was filtered. The filtrate was concentrated and the resulting material was again treated with heptane (2×50 mL) and filtered. The filtrate was concentrated to provide 2-phenylethyl iodide as a clear colorless oil (1.74 g, 19%) that contained a trace amount of triphenylphosphine oxide.

Part B

A mixture of 7-hydroxy-2-propylthiazolo[4,5-c]quinoline (prepared as described in Part A of Example 2, 0.94 g, 3.9 mmol) and cesium carbonate (2.07 g, 6.36 mmol) in DMF (25 mL) was heated at 75° C. for 20 min, then a solution of 2-phenylethyl iodide (1.06 g, 4.24 mmol) in DMF (10 mL) was added dropwise. The solution was heated at 75° C. for 4 d. The DMF was removed in vacuo and the resulting solid was partitioned between chloroform (100 mL) and water (100 mL). The organic layer was washed with water (50 mL) and brine (50 mL), dried over $MgSO_4$, filtered, and concentrated to a dark brown solid. The solid was purified by HPFC (silica gel eluting sequentially with 0-8% CMA in chloroform). The appropriate fractions were combined and concentrated to provide 7-[2-(4-fluorophenyl)ethoxy]-2-propylthiazolo[4,5-c]quinoline as a light yellow solid (0.27 g, 19%).

Part C

7-[2-(4-Fluorophenyl)ethoxy]-2-propylthiazolo[4,5-c]quinoline (0.29 g, 0.79 mmol) was treated with m-CPBA (65% w/w, 0.32 g, 1.2 mmol) according to the method described in Part G of Example 1 to yield 7-[2-(4-fluorophenyl)ethoxy]-2-propylthiazolo[4,5-c]quinoline-5N-oxide as a light orange solid (0.30 g, 100%).

Part D

7-[2-(4-Fluorophenyl)ethoxy]-2-propylthiazolo[4,5-c]quinoline-5N-oxide (0.30 g, 0.78 mmol) was treated with concentrated ammonium hydroxide (4 mL) and p-toluenesulfonyl chloride (0.17 g, 0.86 mmol) according to the method described in Part D of Example 2. The crude product was purified by HPFC (silica gel eluting sequentially with 0-15% CMA in chloroform). The appropriate fractions were combined and concentrated to provide a light yellow solid. The solid was crystallized from acetonitrile. The resulting white solid was isolated, washed with acetonitrile, and dried overnight at 60° C. in a vacuum oven to provide 7-[2-(4-fluorophenyl)ethoxy]-2-propylthiazolo[4,5-c]quinolin-4-amine (0.13 g, 43%), mp 145-148° C. $^1$H NMR (300 MHz, $d_6$-DMSO) δ 7.67 (d, J=8.7 Hz, 1H), 7.40-7.34 (m, 2H), 7.17-7.09 (m, 2H), 7.03 (d, J=2.5 Hz, 1H), 6.87 (dd, J=8.8, 2.5 Hz, 1H), 6.79 (s, 2H), 4.27 (t, J=6.5 Hz, 2H), 3.11 (t, J=7.8 Hz, 2H), 3.06 (t, J=6.6 Hz, 2H), 1.82 (sextet, J=7.2 Hz, 2H), 1.00 (t, J=7.5 Hz, 3H); Anal. calcd for $C_{21}H_{20}N_3OSF$: C, 66.12; H, 5.28; N, 11.02. Found: C, 66.19; H, 5.26; N, 11.03.

Example 4

7-[2-(Benzyloxy)ethoxy]-2-propylthiazolo[4,5-c]quinolin-4-amine

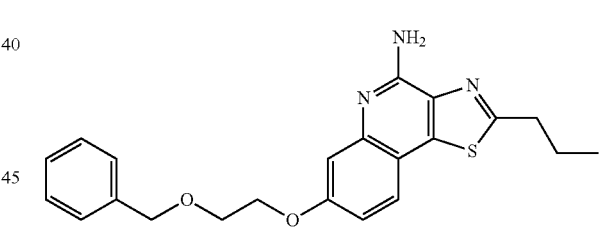

Part A

A solution of 2-(benzyloxy)ethanol (5.12 g, 33.6 mmol), triphenylphosphine (10.59 g, 40.4 mmol), and imidazole (3.21 g, 47.1 mmol) in dichloromethane (250 mL) was treated with iodine (11.10 g, 43.7 mmol) according to the method described in Part A of Example 3 to yield benzyl 2-iodomethyl ether as a clear colorless oil (5.95 g, 68%) that contained a trace amount of triphenylphosphine oxide.

Part B

A mixture of 7-hydroxy-2-propylthiazolo[4,5-c]quinoline (prepared as described in Part A of Example 2, 0.66 g, 2.7 mmol) and cesium carbonate (1.32 g, 4.05 mmol) in DMF (25 mL) was heated at 75° C. for 30 min, then a solution of benzyl 2-iodomethyl ether (1.42 g, 5.40 mmol) in DMF (5 mL) was added dropwise. The solution was heated at 75° C. for 16 h. The DMF was removed in vacuo and the resulting solid was partitioned between chloroform (100 mL) and water (100 mL). The organic layer was washed with water (50 mL) and brine (50 mL), dried over $MgSO_4$, filtered, and concentrated to a dark brown solid. The solid was purified by HPFC (silica gel eluting sequentially with 0-8% CMA in chloroform). The appropriate fractions were combined and concentrated to provide 7-[2-(benzyloxy)ethoxy]-2-propylthiazolo[4,5-c]quinoline as a light yellow solid (0.89 g, 87%).

Part C

7-[2-(Benzyloxy)ethoxy]-2-propylthiazolo[4,5-c]quinoline (0.89 g, 2.35 mmol) was treated with m-CPBA (65% w/w, 0.94 g, 3.53 mmol) according to the method described in Part G of Example 1 to yield 7-[2-(benzyloxy)ethoxy]-2-propylthiazolo[4,5-c]quinoline-5N-oxide as a light yellow solid (0.85 g, 91%).

Part D

7-[2-(Benzyloxy)ethoxy]-2-propylthiazolo[4,5-c]quinoline-5N-oxide (0.85 g, 2.15 mmol) was treated with concentrated ammonium hydroxide (5 mL) and p-toluenesulfonyl chloride (0.45 g, 2.37 mmol) according to the method described in Part D of Example 2. The crude product was purified by HPFC (silica gel eluting sequentially with 0-15% CMA in chloroform). The appropriate fractions were combined and concentrated to provide a light yellow solid. The solid was crystallized from acetonitrile. The resulting white solid was isolated by filtration, washed with acetonitrile, and dried overnight at 60° C. in a vacuum oven to provide 7-[2-(benzyloxy)ethoxy]-2-propylthiazolo[4,5-c]quinolin-4-amine (0.29 g, 34%) as off-white needles, mp 142-145° C. $^1$H NMR (300 MHz, $d_6$-DMSO) δ 7.67 (d, J=8.8 Hz, 1H), 7.37-7.24 (m, 5H), 7.04 (d, J=2.5 Hz, 1H), 6.90 (dd, J=9.0, 2.8 Hz, 1H), 6.80 (s, 2H), 4.57 (s, 2H), 4.24-4.21 (m, 2H), 3.82-3.79 (m, 2H), 3.11 (t, J=7.2 Hz, 2H), 1.84 (sextet, J=7.2 Hz, 2H), 1.00 (t, J=7.5 Hz, 3H); $^{13}$C NMR (75 MHz, $d_6$-DMSO) δ 169.0, 159.1, 152.4, 146.5, 139.36, 138.3, 136.0, 128.2, 127.5, 127.4, 125.7, 113.1, 107.3, 72.1, 68.2, 67.1, 35.1, 22.8, 13.4; Anal. calcd for $C_{22}H_{23}N_3O_2S$: C, 67.15; H, 5.89; N, 10.68. Found: C, 67.11; H, 5.77; N, 10.48.

Example 5

7-(Furan-3-ylmethyloxy)-2-propylthiazolo[4,5-c]quinolin-4-amine

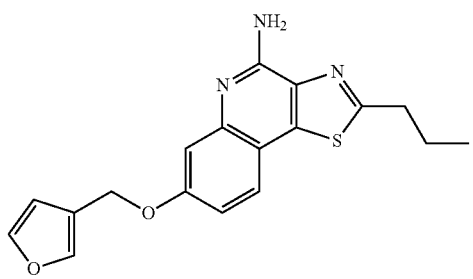

Part A

Diisopropyl azodicarboxylate (1.51 g, 7.5 mmol) was added to a mixture of 7-hydroxy-2-propylthiazolo[4,5-c]quinoline (prepared as described in Part A of Example 2, 920 mg, 3.76 mmol) and triphenylphosphine (1.96 g, 7.5 mmol) in THF (50 mL). The mixture was stirred overnight. The following morning, additional reagents were added to the solution and stirring was continued for 3 h. The solvent was removed in vacuo and the residue was dissolved in dichloromethane and washed with 2% aqueous $Na_2CO_3$ (3×50 mL). The aqueous phases were combined and extracted multiple times with chloroform. The organic phases were combined, dried over $MgSO_4$, filtered, and concentrated. The crude product was purified by HPFC (silica gel eluting with a dichloromethane/methanol gradient). All fractions containing the product 7-(furan-3-ylmethyloxy)-2-propyl-thiazolo[4,5-c]quinoline were combined, concentrated, and carried on to the next step without further purification.

Part B 7-(Furan-3-ylmethyloxy)-2-propylthiazolo[4,5-c]quinoline (prepared as described above in Part A, 3.76 mmol) was treated with m-CPBA (60% w/w, 1.60 g, 5.65 mmol) according to the method described in Part G of Example 1 to yield 7-(furan-3-ylmethyloxy)-2-propyl-thiazolo[4,5-c]quinoline-5N-oxide as a solid. The solid was dissolved in dichloromethane (100 mL) and trichloroacetyl isocyanate (777 mg, 4.13 mmol) was added dropwise to the solution. After all the starting material was consumed in the reaction, concentrated ammonium hydroxide (2 mL) was added. After several minutes the mixture was concentrated in vacuo and the residue was purified by HPFC (silica gel with a gradient elution using 0-15% CMA in chloroform). The appropriate fractions were combined and concentrated to a solid. The solid was dissolved in dichloromethane and loaded onto an acid ion-exchange resin. The resin was washed with methanol (2×40 mL). The 7-(furan-3-ylmethyloxy)-2-propylthiazolo[4,5-c]quinolin-4-amine was eluted with a solution of 2 M ammonia in methanol (2×40 mL). The filtrate was concentrated in vacuo and pure 7-(furan-3-ylmethyloxy)-2-propylthiazolo[4,5-c]quinolin-4-amine was obtained as an off-white crystals, mp 170.0-171.0° C. (143 mg, 12%) after crystallization from acetonitrile. MS (APCI) m/z 340 (M+H)$^+$; Anal. calcd for $C_{18}H_{17}N_3O_2S$: C, 63.70; H, 5.05; N, 12.38. Found: C, 63.38; H, 5.08; N, 12.56.

Examples 6-28

To 7-benzyloxy-2-propylthiazolo[4,5-c]quinolin-4-amine (prepared as described in Example 1, 1.59 g, 4.55 mmol) was added a 30 wt. % solution of hydrogen bromide in acetic acid (25 mL). The resulting solution was heated at 65° C. for 1 h, then cooled in an ice bath. Aqueous NaOH (50% w/w solution) was added slowly until the pH=7 and a light yellow solid formed. The solid was isolated by filtration, dried, and purified by HPFC (silica gel eluting sequentially with 0-10% of a solution comprised of 80% $CHCl_3$, 18% MeOH, and 2% conc. $NH_4OH$ (CMA) in chloroform, then 10-35% CMA in chloroform). The appropriate fractions were concentrated to a light yellow solid that was crystallized from toluene containing a small amount of methanol. The light yellow solid was isolated by filtration, washed with cold toluene, and dried at 60° C. in a vacuum oven to provide the acetic acid salt of 7-hydroxy-2-propylthiazolo[4,5-c]quinolin-4-amine (0.64 g, 54%), mp 236-239° C. $^1$H NMR (300 MHz, $d_6$-DMSO) δ 9.72 (s, 1H), 7.58 (d, J=8.8 Hz, 1H), 6.91 (d, J=2.2 Hz, 1H), 6.78 (dd, J=8.7, 2.2 Hz, 1H), 6.70 (s, 2H), 3.12 (t, J=7.8 Hz, 2H), 1.83 (sextet, J=7.2 Hz, 2H), 0.99 (t, J=7.5 Hz, 3H); $^{13}$C NMR (75 MHz, $d_6$-DMSO) δ 168.4, 158.1, 152.2, 146.6, 139.6, 135.6, 125.7, 113.3, 112.2, 108.9, 35.0, 22.8, 13.4; Anal. calcd for $C_{13}H_{13}N_3OS \cdot 0.22 C_2H_4O_2$: C, 59.23; H, 5.13; N, 15.42. Found: C, 59.42; H, 5.00; N, 15.41.

Aliquots (1 mL, 0.1 mmol) of an anhydrous dimethylformamide solution (39 mL) of 7-hydroxy-2-propylthiazolo[4,5-c]quinolin-4-ylamine (1.01 g, 3.9 mmol) were transferred to test tubes containing anhydrous potassium carbonate (55 mg, 0.4 mmol). Appropriate amounts of the alkylating agents (1.1 equivalents) listed below were added to the test tubes and the test tubes were shaken overnight. A filtration plate was used to remove the potassium carbonate from the reaction mixtures and the filtrates were collected in a 2.2 mL/well titre plate. The solvent was removed by vacuum centrifugation. The compounds were purified by preparative high performance liquid chromatography (prep HPLC) using a Waters Fraction Lynx automated purification system. The prep HPLC fractions were analyzed using a Micromass LC/TOF-MS, and the appropriate fractions were centrifuge evaporated to provide the trifluoroacetate salt of the desired compound.

Column: Zorbax BonusRP, 21.2×50 millimeters (mm), 5 micron particle size; non-linear gradient elution from 5-95% B where A is 0.05% trifluoroacetic acid/water and B is 0.05% trifluoroacetic acid/acetonitrile; fraction collection by mass-selective triggering. The table below shows the reagent used for each example, the structure of the resulting compound, and the observed accurate mass for the isolated trifluoroacetate salt.

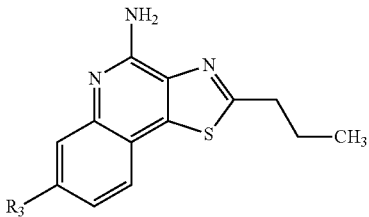

| Example | Reagent | R₃ | Measured Mass (M + H) |
|---|---|---|---|
| 6 | Benzyl bromide | | 350.1351 |
| 7 | α-Bromo-m-xylene | | 364.1489 |
| 8 | 2-Cyanobenzyl bromide | | 375.1294 |
| 9 | 2-Chlorobenzyl bromide | | 384.0940 |
| 10 | 3-Chlorobenzyl bromide | | 384.0964 |
| 11 | 2,3-Difluorobenzyl bromide | | 386.1135 |
| 12 | 2,4-Difluorobenzyl bromide | | 386.1138 |

-continued
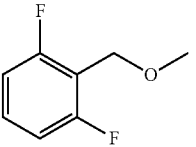
| Example | Reagent | R₃ | Measured Mass (M + H) |
|---|---|---|---|
| 13 | 2,6-Difluorobenzyl bromide | 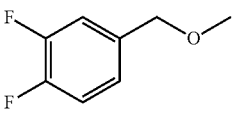 | 386.1146 |
| 14 | 3,4-Difluorobenzyl bromide | 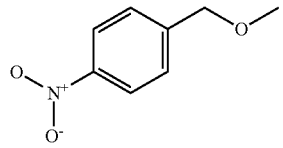 | 386.1156 |
| 15 | 4-Nitrobenzyl bromide | 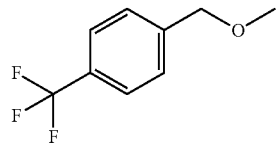 | 395.1208 |
| 16 | 4-(Trifluoromethyl)benzyl bromide | 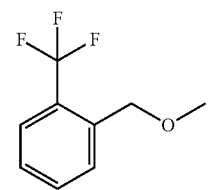 | 418.1194 |
| 17 | 2-(Trifluoromethyl)benzyl bromide | 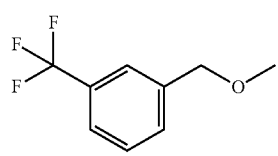 | 418.1221 |
| 18 | 3-(Trifluoromethyl)benzyl bromide | 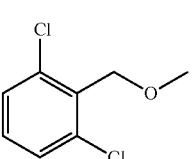 | 418.1209 |
| 19 | 2,6-Dichlorobenzyl bromide | 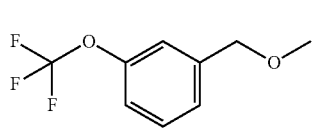 | 418.0553 |
| 20 | 3-(Trifluoromethoxy)benzyl bromide | | 434.1153 |

-continued
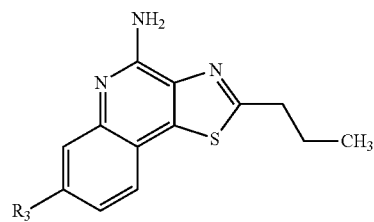
| Example | Reagent | R₃ | Measured Mass (M + H) |
|---|---|---|---|
| 21 | (1-Bromoethyl)benzene | | 364.1512 |
| 22 | α-Bromo-o-xylene | | 364.1486 |
| 23 | 4-Cyanobenzyl bromide | | 375.1289 |
| 24 | 4-Chlorobenzyl bromide | | 384.0956 |
| 25 | 2-(Bromomethyl)-5-nitrofuran | | 385.0987 |
| 26 | 2-(Bromomethyl)naphthalene | | 400.1487 |
| 27 | Methyl 4-(bromomethyl)benzoate | | 408.1399 |
| 28 | Methyl alpha-bromophenylacetate | | 408.1386 |

Example 29

7-Benzyloxy-2-ethylthiazolo[4,5-c]quinolin-4-amine

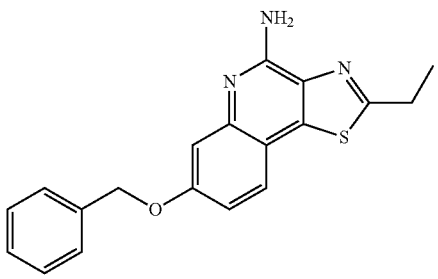

Part A

A 1 L glass Parr bottle was charged with 7-benzyloxy-3-nitroquinolin-7-ol, anhydrous N,N-dimethylformamide (DMF, 500 mL) and 5% Pt/C catalyst (5.0 g). The vessel was placed on Parr apparatus, evacuated and charged with hydrogen gas (~45 psi, $3.1 \times 10^5$ Pa). The reaction mixture was shaken overnight. The reaction mixture was filtered through glass fiber filters to remove catalyst. To the resulting dark colored solution was added concentrated hydrochloric acid (12 N HCl, 14 ml, 168.8 mmol). The product precipitated as the hydrochloride salt. The reaction mixture was stirred over the weekend. A solid was collected by vacuum filtration, washed with diethyl ether (100 mL), and air dried overnight to provide 44 g of 3-amino-7-benzyloxyquinolin-4-ol hydrochloride. This material was carried on without further purification.

Part B

To a stirred solution of 3-amino-7-benzyloxyquinolin-4-ol hydrochloride (40.4 g, 133.4 mmol), and triethylamine (2.5 eq., 33.8 g, 333.6 mmol) in dichloromethane (1000 mL) at room temperature, was slowly added propionyl chloride (1.1 eq., 13.6 g, 146.8 mmol). After 6 hours the reaction was quenched with water (250 ml). The reaction mixture was transferred to a separatory funnel and the layers were separated. The dichloromethane layer was concentrated to provide 41.5 g of N-(7-benzyloxy-4-hydroxyquinolin-3-yl)propionamide as a pale tan crystalline solid. MS (ACPI) m/z=323 (M+H)$^+$. This material was carried on without further purification to the next step.

Part C

To a stirred slurry of N-(7-benzyloxy-4-hydroxyquinolin-3-yl)propionamide in pyridine 500 (mL) was added 0.5 eq. phosphorous pentasulfide (28.6 g, 64.4 mmol). The reaction mixture was heated to reflux. The reaction mixture became homogeneous (dark orange) as the reaction heated to reflux. The reaction was maintained at reflux overnight. The reaction mixture was cooled to room temperature and the excess phosphorous pentasulfide was slowly quenched with 10% aqueous sodium carbonate (50 mL). The reaction mixture was transferred to a separatory funnel and partitioned between water (200 mL) and dichloromethane (700 mL). The layers were separated. The aqueous layer was extracted with dichloromethane (3×100 mL). The organic layers were combined and concentrated to dryness. The resulting tan solid was treated with boiling heptane (3×400 mL) and filtered. The heptane filtrates were combined and concentrated to provide 15 g of 7-benzyloxy-2-ethylthiazolo[4,5-c]quinoline as a pale yellow crystalline solid. MS (ACPI) m/z=321 (M+H)$^+$. This material was carried on without further purification to the next step.

Part D

To a stirred solution of 7-benzyloxy-2-ethylthiazolo[4,5-c]quinoline (15.0 g, 46.8 mmol) in chloroform (150 mL), 3-chloroperoxybezoic acid (m-CPBA. 50% w/w, 16.15 g, 46.8 mmol) was slowly added in small portions. The reaction was maintained at room temperature overnight. The reaction mixture was transferred to a separatory funnel and washed with 10% aqueous sodium carbonate (2×50 mL). The chloroform layer was concentrated to provide 15.4 g of 7-benzyloxy-2-ethylthiazolo[4,5-c]quinoline 5-oxide as a light tan solid. MS (ACPI) m/z=337 (M+H)$^+$. This material was carried on without further purification to the next step.

Part E

To a vigorously stirred pale orange solution of 7-benzyloxy-2-ethylthiazolo[4,5-c]quinoline 5-oxide (15.00 g, 44.6 mmol) in dichloromethane (200 mL), at room temperature, was slowly added trichloroacetylisocyanate (1.05 eq., 5.6 ml 46.8 mmol). The solution was maintained at room temperature for 18 hours. At this time the reaction was quenched by the addition of concentrated ammonium hydroxide solution (60 ml). An off-white precipitate formed and was collected by vacuum filtration. Recrystallization from acetonitrile provided 11.3 g of 7-benzyloxy-2-ethylthiazolo[4,5-c]quinolin-4-amine as a white crystalline solid, mp 208-209° C. MS (APCI) m/z 336.1 (M+H)$^+$; Anal. calcd for $C_{19}H_{17}N_3OS$: C, 68.03; H, 5.11; N, 12.53. Found: C, 67.45; H, 4.83; N, 12.41.

Example 30

2-Ethyl-7-[3-(pyridin-3-yl)propoxy]thiazolo[4,5-c]quinolin-4-amine

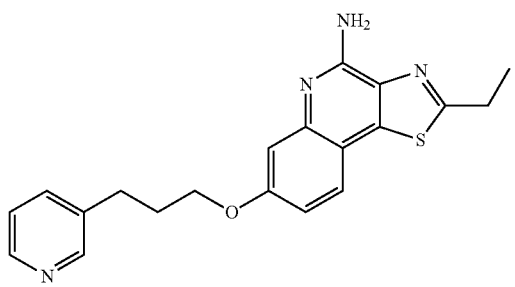

Part A

To a round bottom flask containing 7-benzyloxy-2-ethylthiazolo[4,5-c]quinolin-4-amine (11.3 g, 33.7 mmol) was added a 45 wt. % solution of hydrogen bromide in acetic acid (40 mL). The resulting solution was heated at 65° C. for 2 hours and then cooled in an ice bath. Aqueous sodium hydroxide (50% w/w solution) was added slowly until pH 7 and a pale yellow/green solid formed. The solid was isolated by filtration and air dried to provide 8.4 g of 4-amino-2-ethylthiazolo[4,5-c]quinolin-7-ol. MS (APCI) m/z=246.0.

Part B

To a stirred solution (pale orange) of 4-amino-2-ethylthiazolo[4,5-c]quinolin-7-ol (0.24 g, 1.0 mmol) was dissolved in anhydrous DMF (5 mL) was added cesium carbonate (3.0 eq., 1.0 g, 3.0 mmol) and 1.1 eq. of an 80% solution of propargyl bromide in toluene (0.16 g). The mixture was heated to 65° C. and maintained overnight. The reaction was quenched by slowly adding the reaction mixture to 10 volumes of water (50 mL). The resulting solid was collected by vacuum filtration, rinsed with acetonitrile and air dried, to provide 0.22 g of 2-ethyl-7-[(prop-2-ynyl)oxy]thiazolo[4,5-c]quinolin-4-amine as a pale-peach colored crystalline solid. MS (ACPI) m/z=284 (M+H)+.

Part C

To a stirred solution of 2-ethyl-7-[(prop-2-ynyl)oxy]thiazolo[4,5-c]quinolin-4-amine (0.18 g, 0.635 mmol), and triethylamine (3.0 eq. 0.27 ml, 1.9 mmol) dissolved in anhydrous DMF (5 mL) was added a solution of 3-iodopyridine (1.1 eq. 0.14 g, 0.699 mmol), copper iodide (0.04 eq., 4.8 mg, 0.025 mmol), and PdCl$_2$(PPh$_3$)$_2$ (0.02 eq., 9.12 mg, 0.013 mmol) in anhydrous DMF (10 mL). The reaction mixture was heated to 65° C. under a nitrogen atmosphere for 24 hours. The reaction was quenched by slowly pouring it into water (100 ml). The mixture was extracted with dichloromethane (4×25 ml). The organic fractions were combined and concentrated to dryness. The resulting solid was recrystallized from acetonitrile to provide 0.19 g of 2-ethyl-7-{[(3-(pyridin-3-yl)prop-2-ynyl]oxy}thiazolo[4,5-c]quinolin-4-amine. MS (APCI) m/z=361.1 (M+H).

Part D

A glass Parr vessel was charged with a golden solution of 2-ethyl-7-{[(3-(pyridin-3-yl)prop-2-ynyl]oxy}thiazolo[4,5-c]quinolin-4-amine in 1:1 ethyl acetate:ethanol (150 mL), and 10% Pd/C catalyst (20 mg). The reaction vessel was evacuated and charged with hydrogen (~50 psi, 3.4×10$^5$ Pa). The mixture was shaken for 10 hours at ambient temperature. At this time the reaction was analyzed by thin layer chromatography (10% methanol in dichloromethane) and found to be incomplete. The reaction vessel was re-charged with additional catalyst (23 mg) and hydrogen (~50 psi, 3.4×10$^5$ Pa) and shaken an additional 48 hours. The reaction mixture was filtered to remove catalyst, and then concentrated to dryness. The desired product was purified by HPFC (eluting with a gradient of 0-20% CMA in chloroform, (1440 ml)), followed by recrystallization from acetonitrile, to provide 0.1 g of 2-ethyl-7-[3-(pyridin-3-yl)propoxy]thiazolo[4,5-c]quinolin-4-amine as off white crystals, mp 172-173° C. MS (APCI) m/z 365 (M+H)+.

Example 31

2-Propyl-7-[(thiazol-4-yl)methoxy]thiazolo[4,5-c]quinolin-4-amine

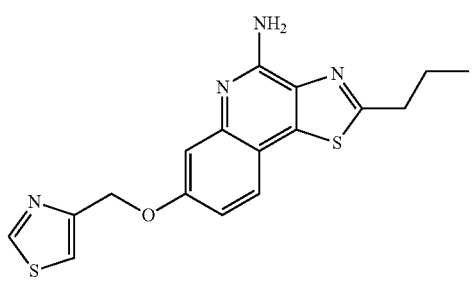

A mixture of 4-amino-2-propylthiazolo[4,5-c]quinolin-7-ol acetate (318 mg, 1.0 mmol), cesium carbonate (1.3 g, 4.0 mmol), tetrabutylammonium bromide (322 mg, 1.0 mmol), and DMF (15 mL) was stirred at 75° C. for 10 minutes. 4-(Chloromethyl)thiazole hydrochloride (187 mg, 1.1 mmol) was added. Additional 4-(chloromethyl)thiazole hydrochloride (1 eq. total) was added in small portions over a period of 3 hours. The reaction mixture was poured into water (100 mL). A solid was isolated by filtration, allowed to dry, dissolved in dichloromethane, and then purified by HPFC eluting with a gradient of 0-25% CMA in chloroform over 1400 mL and then 25% CMA in chloroform over 600 mL. The resulting solid was recrystallized from acetonitrile to provide 200 mg of 2-propyl-7-[(thiazol-4-yl)methoxy]thiazolo[4,5-c]quinolin-4-amine as an off-white solid, mp 218.0-220.0° C. MS (APCI) m/z 357 (M+H)+; Anal. calcd for C$_{17}$H$_{16}$N$_4$OS$_2$.0.2H$_2$O: C, 56.71; H, 4.59; N, 15.56. Found C, 56.66; H, 4.29; N, 15.45.

Example 32

2-Propyl-7-[(pyridin-3-yl)methoxy]thiazolo[4,5-c]quinolin-4-amine

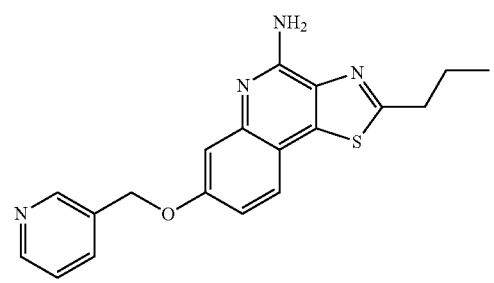

A mixture of 4-amino-2-propylthiazolo[4,5-c]quinolin-7-ol acetate (318 mg, 1.0 mmol), cesium carbonate (1.3 g, 4.0 mmol), and DMF (20 mL) was stirred at 75° C. for 10 minutes. 3-(Iodomethyl)pyridine hydroiodide (381 mg, 1.1 mmol) was added in portions over a period of 3 hours. The heat source was removed and the reaction mixture was stirred at ambient temperature overnight. The reaction mixture was diluted with water (250 mL), stirred for 1 hour, and then filtered. The isolated solid was rinsed with water and then dried to provide a brown powder. This material was dissolved in dichloromethane and then purified by HPFC eluting with a gradient of 0-20% CMA in chloroform over 1400 mL and then 20% CMA in chloroform over 600 mL. The resulting solid was recrystallized from acetonitrile to provide 160 mg of 2-propyl-7-[(pyridin-3-yl)methoxy]thiazolo[4,5-c]quinolin-4-amine as an off-white solid, mp 167.0-169.0° C. MS (APCI) m/z 351 (M+H)+; Anal. calcd for C$_{19}$H$_{18}$N$_4$OS: C, 65.12; H, 5.18; N, 15.99. Found C, 65.25; H, 5.06; N, 16.03.

Example 33

2-Propyl-7-[2-(pyrrol-1-yl)ethoxy]thiazolo[4,5-c]quinolin-4-amine

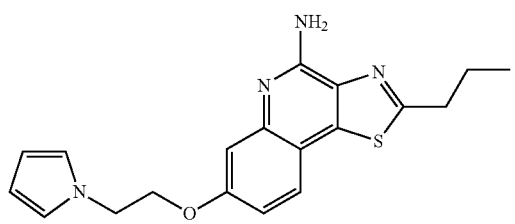

A mixture of 4-amino-2-propylthiazolo[4,5-c]quinolin-7-ol acetate (318 mg, 1.0 mmol), cesium carbonate (1.3 g, 4.0 mmol), and DMF (20 mL) was stirred at 75° C. for 10 minutes. 1-(2-Bromoethyl)pyrrole (200 mg, 1.1 mmol) was added dropwise over a period of 10 minutes. After 3 hours an additional equivalent of cesium carbonate was added in a single portion followed by the dropwise addition of an equivalent of 1-(2-bromoethyl)pyrrole. The reaction mixture was stirred overnight and then an additional equivalent of both cesium carbonate and 1-(2-bromoethyl)pyrrole were added. After 1 hour the heat source was removed; the reaction mixture was diluted with water (250 mL), stirred for 1 hour, and then filtered. The isolated solid was rinsed with water and then dried to provide a brown powder. This material was dissolved in dichloromethane and then purified by HPFC eluting with a gradient of 0-15% CMA in chloroform over 1500 mL. The resulting solid was recrystallized from acetonitrile to provide 143 mg of 2-propyl-7-[2-(pyrrol-1-yl)ethoxy]thiazolo[4,5-c]quinolin-4-amine as an off-white solid, mp 158.0-160.0° C. MS (ESI) m/z 353 (M+H)$^+$; Anal. calcd for $C_{19}H_{20}N_4OS$: C, 64.75; H, 5.72; N, 15.90. Found C, 64.86; H, 5.38; N, 16.00.

Example 34

2-Propyl-7-[3-(pyrrol-1-yl)propoxy]thiazolo[4,5-c]quinolin-4-amine

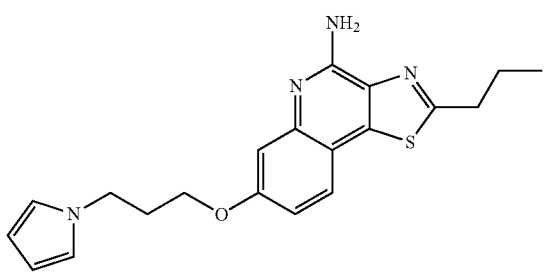

A mixture of 4-amino-2-propylthiazolo[4,5-c]quinolin-7-ol acetate (318 mg, 1.0 mmol), cesium carbonate (1.3 g, 4.0 mmol), and DMF (20 mL) was stirred at 75° C. for 10 minutes. 1-(2-Bromopropyl)pyrrole (206 mg, 1.1 mmol) was added dropwise over a period of 10 minutes. After 3 hours an additional equivalent of cesium carbonate was added in a single portion followed by the dropwise addition of an equivalent of 1-(2-bromopropyl)pyrrole. After 1 additional hour the heat source was removed; the reaction mixture was diluted with water (250 mL), stirred for 1 hour, and then filtered. The isolated solid was rinsed with water and then dried to provide a brown powder. This material was dissolved in dichloromethane and then purified by HPFC eluting with a gradient of 0-20% CMA in chloroform over 1500 mL. The resulting solid was recrystallized from acetonitrile to provide 168 mg of 2-propyl-7-[3-(pyrrol-1-yl)propoxy]thiazolo[4,5-c]quinolin-4-amine as an off-white solid, mp 152.0-154.0° C. MS (ESI) m/z 367 (M+H)$^+$; Anal. calcd for $C_{20}H_{22}N_4OS$: C, 65.55; H, 6.05; N, 15.29. Found C, 65.52; H, 5.80; N, 15.37.

Example 35

7-[(3,5-Dimethylisoxazol-4-yl)methoxy]-2-propylthiazolo[4,5-c]quinolin-4-amine

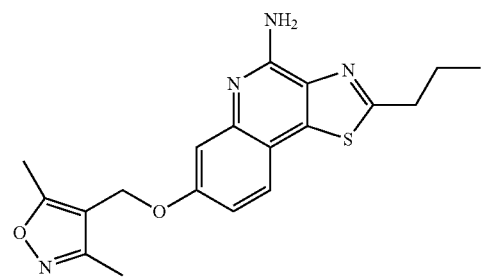

A mixture of 4-amino-2-propylthiazolo[4,5-c]quinolin-7-ol acetate (318 mg, 1.0 mmol), cesium carbonate (1.3 g, 4.0 mmol), and DMF (20 mL) was stirred at 75° C. for 10 minutes. 4-(Chloromethyl)-3,5-dimethylisoxazole (160 mg, 1.1 mmol) was added dropwise over a period of 10 minutes. After 3 hours an additional equivalent of cesium carbonate was added in a single portion followed by the dropwise addition of an equivalent of 4-(chloromethyl)-3,5-dimethylisoxazole. After 1 additional hour the heat source was removed; the reaction mixture was diluted with water (250 mL), stirred for 1 hour, and then filtered. The isolated solid was rinsed with water and then dried to provide a brown powder. This material was dissolved in dichloromethane and then purified by HPFC eluting with a gradient of 0-5% methanol in dichloromethane for over 1000 mL and then with 5% methanol in dichloromethane over 400 mL. The resulting solid was recrystallized from acetonitrile to provide 156 mg of 7-[(3,5-dimethylisoxazol-4-yl)methoxy]-2-propylthiazolo[4,5-c]quinolin-4-amine as an off-white solid, mp 178.0-180.0° C. MS (ESI) m/z 369 (M+H)$^+$; Anal. calcd for $C_{19}H_{20}N_4O_2S$: C, 61.94; H, 5.47; N, 15.21. Found C, 61.98; H, 5.25; N, 15.26.

Example 36

2-Ethyl-7-{[5-(trifluoromethyl)furan-2-yl]methoxy}thiazolo[4,5-c]quinolin-4-amine

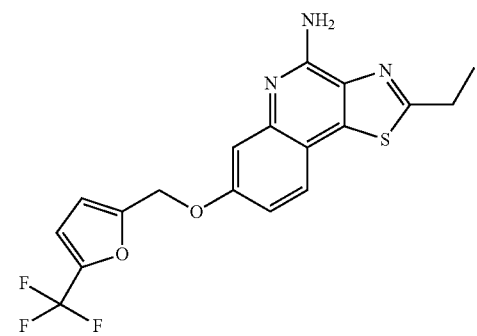

A mixture of 4-amino-2-ethylthiazolo[4,5-c]quinolin-7-ol (245 mg, 1.0 mmol), cesium carbonate (1.3 g, 4.0 mmol), and DMF (20 mL) was stirred at 75° C. for 10 minutes. 2-(Bromomethyl)-5-(trifluoromethyl)furan (252 mg, 1.1 mmol) was added in portions over a period of 30 minutes. The reaction mixture was stirred for 1 hour and then the heat source was removed. The reaction mixture was diluted with water (250 mL), stirred for 1 hour, and then filtered. The isolated solid was rinsed with water and then dried to provide a brown powder. This material was dissolved in dichloromethane and then purified by HPFC eluting with a gradient of 0-15 CMA in chloroform 700 mL and then with 15% CMA in chloroform over 200 mL. The resulting solid was recrystallized from acetonitrile to provide 125 mg of 2-ethyl-7-{[5-(trifluoromethyl)furan-2-yl]methoxy}thiazolo[4,5-c]quinolin-4-amine as an off-white solid, mp 152-154° C. MS (ESI) m/z 394 (M+H)+; Anal. calcd for $C_{18}H_{14}F_3N_3O_2S$: C, 54.96; H, 3.59; N, 10.68. Found: C, 54.90; H, 3.46; N, 10.52.

Example 37

4-{[(4-Amino-2-ethylthiazolo[4,5-c]quinolin-7-yl)oxy]methyl}-N-[2-(1H-indol-2-yl)ethyl]benzenesulfonamide

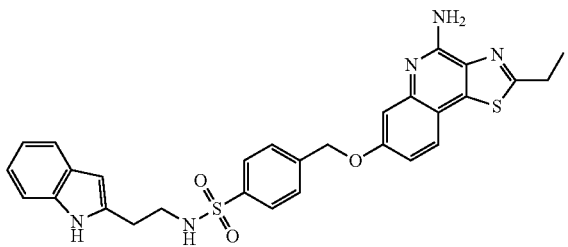

A mixture of 4-amino-2-ethylthiazolo[4,5-c]quinolin-7-ol (245 mg, 1.0 mmol), cesium carbonate (1.3 g, 4.0 mmol), and DMF (20 mL) was stirred at 75° C. for 10 minutes. {[4-(Bromomethyl)phenyl]sulfonyl}[2-(indol-3-yl)ethyl]amine (432 mg, 1.1 mmol) was added in portions over a period of 30 minutes. Several small additions of {[4-(bromomethyl)phenyl]sulfonyl}[2-(indol-3-yl)ethyl]amine were made over several hours. The reaction mixture was diluted with water (250 mL) and then extracted with chloroform (3×100 mL). The extracts were combined and concentrated under reduced pressure. The residue was purified by HPFC eluting with a gradient of 0-20% CMA in chloroform over 700 mL and then with 20% CMA in chloroform over 400 mL. The resulting solid was recrystallized from 100:1 acetonitrile:water to provide 6 mg of 4-{[(4-amino-2-ethylthiazolo[4,5-c]quinolin-7-yl)oxy]methyl}-N-[2-(1H-indol-2-yl)ethyl]benzenesulfonamide as an off-white solid, mp 100.0-101.0° C. MS (APCI) m/z 558 (M+H)+; Anal. calcd for $C_{29}H_{27}N_5O_3S_2$: C, 62.46; H, 4.88; N, 12.56. Found C, 62.27; H, 4.63; N, 12.73.

Example 38

7-[(6-Chloropyridin-2-yl)methoxy]-2-ethylthiazolo[4,5-c]quinolin-4-amine

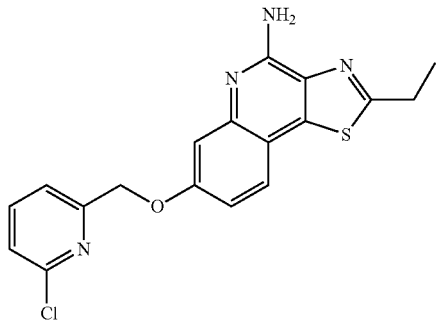

A mixture of 4-amino-2-ethylthiazolo[4,5-c]quinolin-7-ol (245 mg, 1.0 mmol), cesium carbonate (1.3 g, 4.0 mmol), tetrabutylammonium bromide (322 mg, 1.0 mmol), and DMF (15 mL) was stirred at 75° C. for 10 minutes. 2-Chloro-5-(chloromethyl)pyridine (178 mg, 1.1 mmol) was added in portions over a period of 30 minutes. The reaction mixture was stirred for 1 hour and then the heat source was removed. The reaction mixture was diluted with water (200 mL) and then filtered. The isolated solid was rinsed with water and then dried to provide an off white powder. This material was dissolved in dichloromethane and then purified by HPFC eluting with a gradient of 0-15 CMA in chloroform 700 mL and then with 15% CMA in chloroform over 600 mL. The resulting solid was slurried with hot 10:1 acetonitrile:methanol to provide 216 mg of 7-[(6-chloropyridin-2-yl)methoxy]-2-ethylthiazolo[4,5-c]quinolin-4-amine as a pale yellow solid, mp 229.0-230.0° C. MS (APCI) m/z 371 (M+H)+; Anal. calcd for $C_{18}H_{15}ClN_4OS \cdot 0.1CHCl_3$: C, 57.06; H, 4.32; N, 14.63. Found C, 56.79; H, 3.98; N, 14.63.

Example 39

7-[2-(3,5-Dimethyl-1H-pyrazol-4-yl)ethoxy]-2-ethylthiazolo[4,5-c]quinolin-4-amine

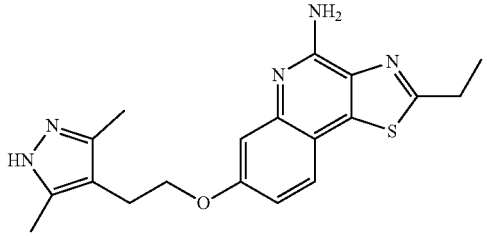

A mixture of 4-amino-2-ethylthiazolo[4,5-c]quinolin-7-ol (245 mg, 1.0 mmol), cesium carbonate (1.3 g, 4.0 mmol), and DMF (20 mL) was stirred at 75° C. for 10 minutes. 4-(Bromoethyl)-3,5-dimethyl-1H-pyrazole (223 mg, 1.1 mmol) was added in portions over a period of 30 minutes. The reaction mixture was stirred for 20 minutes and then the heat source was removed. The reaction mixture was diluted with water (250 mL), stirred overnight, and then filtered. The isolated solid was rinsed with water and then dried to provide a tan powder. This material was dissolved in dichloromethane and then purified by HPFC eluting with a gradient of 0-30% CMA in chloroform 700 mL and then with 30% CMA in chloroform over 200 mL. The resulting solid was recrystallized from 50:1 acetonitrile:methanol (40 mL) to provide 205 mg of 7-[2-(3,5-dimethyl-1H-pyrazol-4-yl)ethoxy]-2-ethylthiazolo[4,5-c]quinolin-4-amine as an off white solid, mp 195.0-197.0° C. MS (APCI) m/z 368 (M+H)+; Anal. calcd for $C_{19}H_{21}N_5OS$: C, 62.10; H, 5.764; N, 19.06. Found C, 61.95; H, 5.53; N, 19.09.

Example 40

(1-{[3-(4-Amino-2-ethylthiazolo[4,5-c]quinolin-7-yl)oxy]propyl}-1H-[1,2,3]triazol-4-yl)methanol

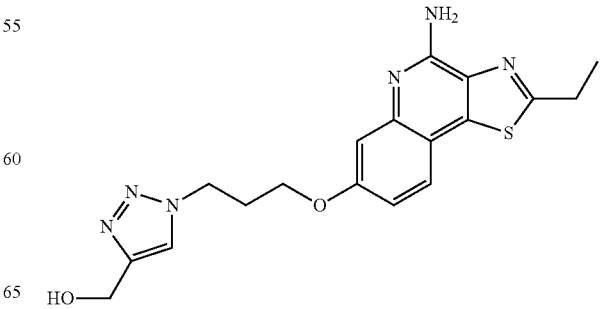

Part A

A mixture of 4-amino-2-ethylthiazolo[4,5-c]quinolin-7-ol (1.00 mg, 4.08 mmol), cesium carbonate (5.30 g, 16.3 mmol), and DMF (40 mL) was stirred at 50° C. for 10 minutes. A portion (0.05 mL) of a solution (1.1 mL) of 1-bromo-3-chloropropane (705 mg, 4.48 mmol) in DMF was added every 7 minutes. After 2 hours the reaction mixture was poured into water (225 mL). The mixture was stirred for 30 minutes and then filtered. The isolated solid was dried to provide 785 mg of 7-(3-chloropropoxy)-2-ethylthiazolo[4,5-c]quinolin-4-amine as a brown solid.

Part B

A solution of 7-(3-chloropropoxy)-2-ethylthiazolo[4,5-c]quinolin-4-amine (684 mg, 2.12 mmol) in DMF (20 mL) was heated to 110° C. Sodium azide (151 mg, 2.33 mol) was added in a single portion. After 1 hour the reaction mixture was poured into water (100 mL). The mixture was extracted with chloroform (3×100 mL). The combined extracts were concentrated under reduced pressure. The residue was dissolved in chloroform and purified by HPFC eluting with a gradient of 0-20% CMA in chloroform over 700 mL and then with 20% CMA in chloroform over 600 mL to provide 400 mg of 7-(3-azidopropxy)-2-ethylthiazolo[4,5-c]quinolin-4-amine as a pale yellow solid.

Part C

The material from Part B (1.21 mmol), propargyl alcohol (134 mg, 2.4 mmol), copper(II) sulfate pentahydrate (30 mg, 0.12 mmol), sodium ascorbate (24 mg, 0.12 mmol), water (2 mL), and DMF (8 mL) were combined and stirred at 70° C. for 2 hours. The reaction mixture was cooled, diluted with water (200 mL), stirred for 40 minutes, and then filtered. The isolated solid was dissolved in chloroform and purified by HPFC eluting with a gradient of 0-30% CMA in chloroform over 700 mL and then with 30% CMA in chloroform over 600 mL. The resulting solid was slurried with hot 10:1 acetonitrile:methanol to provide 280 mg of (1-{[3-(4-amino-2-ethylthiazolo[4,5-c]quinolin-7-yl)oxy]propyl}-1H-[1,2,3]triazol-4-yl)methanol as an off white solid, mp 194.0-197.0° C. MS (APCI) m/z 385 (M+H)$^+$; Anal. calcd for $C_{18}H_{20}N_6O_2S$: C, 56.23; H, 5.24; N, 21.86. Found C, 56.49; H, 5.12; N, 21.94.

Example 41

7-[(1,3-Benzothiazol-2-yl)methoxy]-2-ethylthiazolo[4,5-c]quinolin-4-amine

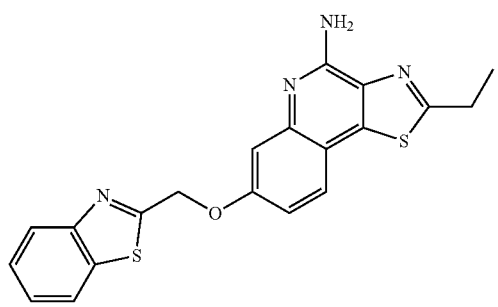

A scintillation vial was charged with 4-amino-2-ethylthiazolo[4,5-c]quinolin-7-ol and anhydrous N,N-dimethylformamide (DMF, 2 mL). The mixture was warmed until a solution was obtained. An additional amount of DMF (1 mL) was added. To this stirred orange solution was added cesium carbonate (3.0 eq.) and a solution of 2-(bromomethyl)benzothiazole dissolved in DMF (2 mL). Additional DMF (1 mL) was used to rinse the vial. The vial was capped and heated to 60° C. overnight. The reaction was monitored by HPLC. The reaction was quenched by adding the reaction mixture drop-wise to water (60 mL) with stirring. A precipitate formed. The solid was collected by vacuum filtration. The solid was then dissolved in methanol and adsorbed onto silica gel (6 g) for purification by HPFC (0-15% CMA in chloroform, 1440 mL). Pure fractions were combined and concentrated; the resulting solid was recrystallized from acetonitrile to provide 7-[(1,3-benzothiazol-2-yl)methoxy]-2-ethylthiazolo[4,5-c]quinolin-4-amine as a white crystalline solid, mp. 211-212° C. MS (APCI) m/z 393 (M+H)$^+$. Anal. calcd $C_{20}H_{16}N_4OS_2.0.6H_2O$: C, 59.56; H, 4.30; N, 13.89. Found: C, 59.66; H, 4.08; N, 13.80.

Example 42

Methyl 5-{[(4-amino-2-ethylthiazolo[4,5-c]quinolin-7-yl)oxy]methyl}-2-furoate

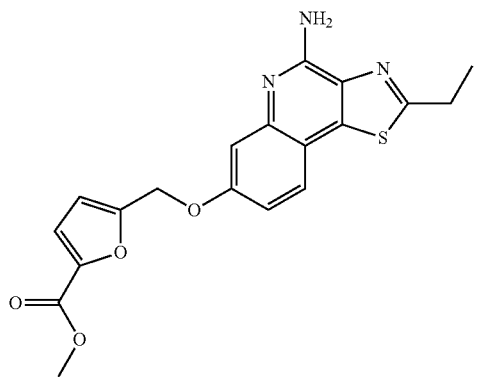

A scintillation vial was charged with 4-amino-2-ethylthiazolo[4,5-c]quinolin-7-ol (1.0 eq., 1.0 mmol) and anhydrous DMF (2 mL). The mixture was warmed until a solution was obtained. An additional amount of DMF (1 mL) was added. To this stirred orange solution was added cesium carbonate (3.0 eq., 3.0 mmol) and a solution of ethyl 5-(chloromethyl)-2-furancarboxylate (1.0 eq., 1.0 mmol) dissolved in DMF (2 mL). Additional DMF (1 mL) was used to rinse the vial. The vial was capped and heated to 60° C. overnight. The reaction was monitored by HPLC. The reaction was quenched by adding the reaction mixture drop-wise to water (60 mL) with stirring. A precipitate formed. Crude ethyl 5-{[(4-amino-2-ethylthiazolo[4,5-c]quinolin-7-yl)oxy]methyl}-2-furoate was isolated as a solid by vacuum filtration. The solid was then dissolved in methanol and adsorbed onto silica gel (6 g) for purification by HPFC (0-15% CMA in chloroform, 1440 mL). Pure fractions were combined and concentrated to provide a solid which analysis indicated was the methyl ester. This material was recrystallized from acetonitrile to provide methyl 5-{[(4-amino-2-ethylthiazolo[4,5-c]quinolin-7-yl)oxy]methyl}-2-furoate as a light yellow crystalline solid, mp 184-186° C. MS (APCI) m/z 384 (M+H)$^+$. Anal. calcd for $C_{19}H_{17}N_3O_4S \cdot 0.30CH_3CN$: C, 59.49; H, 4.56; N, 11.68. Found: C, 59.35; H, 4.22; N, 11.71.

Example 43

6-{[(4-Amino-2-ethylthiazolo[4,5-c]quinolin-7-yl)oxy]methyl}pyridin-2-yl)methanol

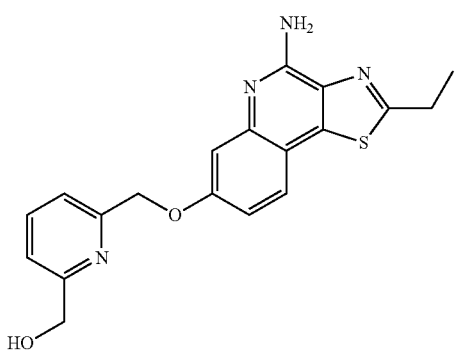

A scintillation vial was charged with 4-amino-2-ethylthiazolo[4,5-c]quinolin-7-ol (1.0 eq., 1.0 mmol) and anhydrous DMF (2 mL). The mixture was warmed until a solution was obtained. An additional amount of DMF (1 mL) was added. To this stirred orange solution was added cesium carbonate (3.0 eq., 3.0 mmol) and a solution of 6-(bromomethyl)-2-pyridinemethanol (1.0 eq., 1.0 mmol) dissolved in DMF (2 mL). Additional DMF (1 mL) was used to rinse the vial. The vial was capped and heated to 60° C. overnight. The reaction was monitored by HPLC. The reaction was quenched by adding the reaction mixture drop-wise to water (60 mL) with stirring. A precipitate formed. The solid was collected by vacuum filtration. The solid was then dissolved in methanol and adsorbed onto silica gel (6 g) for purification by HPFC (0-15% CMA-chloroform, 1440 mL). Pure fractions were combined and concentrated; the resulting solid was recrystallized from acetonitrile to provide 6-{[(4-amino-2-ethylthiazolo[4,5-c]quinolin-7-yl)oxy]methyl}pyridin-2-yl)methanol as a pale yellow crystalline solid, mp 186-187° C. MS (APCI) m/z 367 (M+H)$^+$. Anal. calcd for $C_{19}H_{18}N_4O_2S \cdot 0.30H_2O$: C, 61.37; H, 5.04; N, 15.07. Found: C, 61.08; H, 4.92; N, 15.11.

Example 44

Methyl 6-[(4-amino-2-ethylthiazolo[4,5-c]quinolin-7-yl)oxy]nicotinate

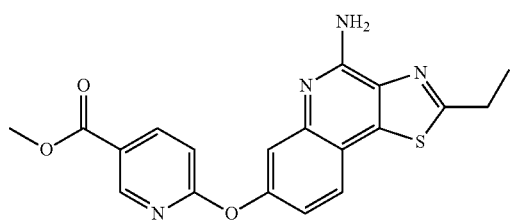

A round bottom flask was charged with 4-amino-2-ethylthiazolo[4,5-c]quinolin-7-ol (1.0 eq., 2.0 mmol), methyl 6-chloronicotinate (1.0 eq., 2.0 mmol), cesium carbonate (3.0 eq. 6.0 mmol), and anhydrous 1,4-dioxane (45 mL). The mixture was heated to reflux for 24 hours. The reaction was monitored by HPLC. The reaction mixture was concentrated to dryness. The resulting solid was then dissolved in methanol and adsorbed onto silica gel (6 g) for purification by HPFC (0-15% CMA in chloroform, 1440 mL). Pure fractions were combined and concentrated; the resulting solid was recrystallized from acetonitrile to provide methyl 6-[(4-amino-2-ethyl[1,3]thiazolo[4,5-c]quinolin-7-yl)oxy]nicotinate as a light peach colored crystalline solid, mp 213-214° C. MS (APCI) m/z 381 (M+H)$^+$. Anal. calcd for $C_{19}H_{16}N_4O_3S$: C, 59.99; H, 4.24; N, 14.73. Found: C, 59.76; H, 4.19; N, 14.71.

Example 45

2-ethyl-7-[2-(1H-indol-3-yl)ethoxy]thiazolo[4,5-c]quinolin-4-amine

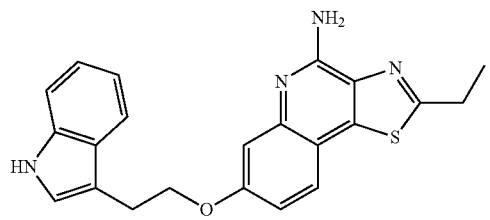

A scintillation vial was charged with 4-amino-2-ethylthiazolo[4,5-c]quinolin-7-ol (1.0 eq., 1.0 mmol) and anhydrous DMF (2 mL). The mixture was warmed until a solution was obtained. An additional amount of DMF (1 mL) was added. To this stirred orange solution was added cesium carbonate (3.0 eq., 3.0 mmol) and a solution of 3-(2-bromoethyl)indole (1.0 eq., 1.0 mmol) dissolved in DMF (2 mL). Additional DMF (1 mL) was used to rinse the vial. The vial was capped and heated to 60° C. overnight. The reaction was monitored by HPLC. The reaction was quenched by adding the reaction mixture drop-wise to water (60 ml) with stirring. A precipitate formed. The solid was collected by vacuum filtration. The solid was then dissolved in methanol and adsorbed onto silica gel (6 g) for purification by HPFC (0-15% CMA in chloroform, 1440 mL). Pure fractions were combined and concentrated; the resulting solid was recrystallized from methanol to provide a peach colored crystalline solid, mp 218-220° C. MS (APCI) m/z 389 (M+H)$^+$. Anal. calcd for $C_{22}H_{20}N_4OS \cdot 0.8 CH_3OH$: C, 66.13; H, 5.65; N, 13.53. Found: C, 66.43; H, 5.03; N, 13.90.

Exemplary Compounds

Certain exemplary compounds, including some of those described above in the Examples, have the following Formulas (IIa or IIIa) and the following $R_2$ and $R_{3a}$ substituents, wherein each line of the table is matched with Formula IIa or IIIa to represent a specific compound.

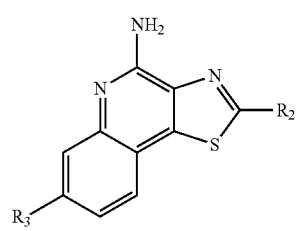

IIa

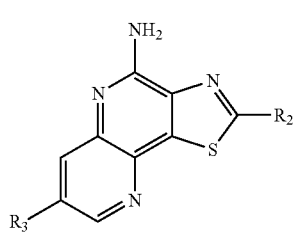

IIIa

| $R_2$ | $R_3$ |
|---|---|
| methyl | 4-fluorobenzyloxy |
| methyl | 2,4-difluorobenzyloxy |
| methyl | 6-chlorobenzyloxy |
| methyl | 2-chlorobenzyloxy |
| methyl | (pyridin-3-yl)methoxy |
| methyl | (pyridin-4-yl)methoxy |
| methyl | 2-(4-fluorophenyl)ethoxy |
| ethyl | 4-fluorobenzyloxy |
| ethyl | 2,4-difluorobenzyloxy |
| ethyl | 6-chlorobenzyloxy |
| ethyl | 2-chlorobenzyloxy |
| ethyl | (pyridin-3-yl)methoxy |
| ethyl | (pyridin-4-yl)methoxy |
| ethyl | 2-(4-fluorophenyl)ethoxy |
| propyl | 4-fluorobenzyloxy |
| propyl | 2,4-difluorobenzyloxy |
| propyl | 6-chlorobenzyloxy |
| propyl | 2-chlorobenzyloxy |
| propyl | (pyridin-3-yl)methoxy |
| propyl | (pyridin-4-yl)methoxy |
| propyl | 2-(4-fluorophenyl)ethoxy |
| methoxymethyl | 4-fluorobenzyloxy |
| methoxymethyl | 2,4-difluorobenzyloxy |
| methoxymethyl | 6-chlorobenzyloxy |
| methoxymethyl | 2-chlorobenzyloxy |
| methoxymethyl | (pyridin-3-yl)methoxy |
| methoxymethyl | (pyridin-4-yl)methoxy |
| methoxymethyl | 2-(4-fluorophenyl)ethoxy |
| ethoxymethyl | 4-fluorobenzyloxy |
| ethoxymethyl | 2,4-difluorobenzyloxy |
| ethoxymethyl | 6-chlorobenzyloxy |
| ethoxymethyl | 2-chlorobenzyloxy |
| ethoxymethyl | (pyridin-3-yl)methoxy |
| ethoxymethyl | (pyridin-4-yl)methoxy |
| ethoxymethyl | 2-(4-fluorophenyl)ethoxy |
| 2-methoxyethyl | 4-fluorobenzyloxy |
| 2-methoxyethyl | 2,4-difluorobenzyloxy |
| 2-methoxyethyl | 6-chlorobenzyloxy |
| 2-methoxyethyl | 2-chlorobenzyloxy |
| 2-methoxyethyl | (pyridin-3-yl)methoxy |
| 2-methoxyethyl | (pyridin-4-yl)methoxy |
| 2-methoxyethyl | 2-(4-fluorophenyl)ethoxy |

Cytokine Induction in Human Cells

Compounds of the invention have been found to modulate cytokine biosynthesis by inducing the production of interferon α and/or tumor necrosis factor α in human cells when tested using the method described below.

An in vitro human blood cell system is used to assess cytokine induction. Activity is based on the measurement of interferon (α) and tumor necrosis factor (α) (IFN-α and TNF-α, respectively) secreted into culture media as described by Testerman et. al. in "Cytokine Induction by the Immunomodulators Imiquimod and S-27609", *Journal of Leukocyte Biology*, 58, 365-372 (September, 1995).

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Blood is diluted 1:1 with Dulbecco's Phosphate Buffered Saline (DPBS) or Hank's Balanced Salts Solution (HBSS). Alternately, whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4 \times 10^6$ cells/mL in RPMI complete. The PBMC suspension is added to 96 well flat bottom sterile tissue culture plates containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested at concentrations ranging from 30-0.014 µM. Controls include cell samples with media only, cell samples with DMSO only (no compound), and cell samples with reference compound.

Incubation

The solution of test compound is added at 60 µM to the first well containing RPMI complete and serial 3 fold dilutions are made in the wells. The PBMC suspension is then added to the wells in an equal volume, bringing the test compound concentrations to the desired range (usually 30-0.014 µM). The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200×g) at 4° C. The cell-free culture supernatant is removed and transferred to sterile polypropylene tubes. Samples are maintained at −30 to −70° C. until analysis. The samples are analyzed for IFN-α by ELISA and for TNF-α by IGEN/BioVeris Assay.

Interferon (α) and Tumor Necrosis Factor (α) Analysis

IFN-α concentration is determined with a human multi-subtype colorimetric sandwich ELISA (Catalog Number 41105) from PBL Biomedical Laboratories, Piscataway, N.J. Results are expressed in pg/mL.

The TNF-α concentration is determined by ORIGEN M-Series Immunoassay and read on an IGEN M-8 analyzer from BioVeris Corporation, formerly known as IGEN International, Gaithersburg, Md. The immunoassay uses a human TNF-α capture and detection antibody pair (Catalog Numbers AHC3419 and AHC3712) from Biosource International, Camarillo, Calif. Results are expressed in pg/mL.

Assay Data and Analysis

In total, the data output of the assay consists of concentration values of TNF-α and IFN-α (y-axis) as a function of compound concentration (x-axis).

Analysis of the data has two steps. First, the greater of the mean DMSO (DMSO control wells) or the experimental background (usually 20 pg/mL for IFN-α and 40 pg/mL for TNF-α) is subtracted from each reading. If any negative values result from background subtraction, the reading is reported as "*", and is noted as not reliably detectable. In subsequent calculations and statistics, "*", is treated as a zero. Second, all background subtracted values are multiplied by a single adjustment ratio to decrease experiment to experiment variability. The adjustment ratio is the area of the reference compound in the new experiment divided by the expected area of the reference compound based on the past 61 experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from the past 61 experiments.

The minimum effective concentration is calculated based on the background-subtracted, reference-adjusted results for a given experiment and compound. The minimum effective concentration (μmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

Cytokine Induction in Human Cells

High Throughput Screen

The CYTOKINE INDUCTION 1N HUMAN CELLS test method described above was modified as follows for high throughput screening.

Blood Cell Preparation for Culture

Whole blood from healthy human donors is collected by venipuncture into vacutainer tubes or syringes containing EDTA. Peripheral blood mononuclear cells (PBMC) are separated from whole blood by density gradient centrifugation using HISTOPAQUE-1077 (Sigma, St. Louis, Mo.) or Ficoll-Paque Plus (Amersham Biosciences Piscataway, N.J.). Whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $4 \times 10^6$ cells/mL in RPMI complete (2-fold the final cell density). The PBMC suspension is added to 96-well flat bottom sterile tissue culture plates.

Compound Preparation

The compounds are solubilized in dimethyl sulfoxide (DMSO). The compounds are generally tested at concentrations ranging from 30-0.014 μM. Controls include cell samples with media only, cell samples with DMSO only (no compound), and cell samples with a reference compound 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) on each plate. The solution of test compound is added at 7.5 mM to the first well of a dosing plate and serial 3 fold dilutions are made for the 7 subsequent concentrations in DMSO. RPMI Complete media is then added to the test compound dilutions in order to reach a final compound concentration of 2-fold higher (60-0.028 μM) than the final tested concentration range.

Incubation

Compound solution is then added to the wells containing the PBMC suspension bringing the test compound concentrations to the desired range (usually 30-0.014 μM) and the DMSO concentration to 0.4%. The final concentration of PBMC suspension is $2 \times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 10 minutes at 1000 rpm (approximately 200 g) at 4° C. 4-plex Human Panel MSD MULTI-SPOT 96-well plates are pre-coated with the appropriate capture antibodies by MesoScale Discovery, Inc. (MSD, Gaithersburg, Md.). The cell-free culture supernatants are removed and transferred to the MSD plates. Fresh samples are typically tested, although they may be maintained at −30 to −70° C. until analysis.

Interferon-α and Tumor Necrosis Factor-α Analysis

MSD MULTI-SPOT plates contain within each well capture antibodies for human TNF-α and human IFN-α that have been pre-coated on specific spots. Each well contains four spots: one human TNF-α capture antibody (MSD) spot, one human IFN-α capture antibody (PBL Biomedical Laboratories, Piscataway, N.J.) spot, and two inactive bovine serum albumin spots. The human TNF-α capture and detection antibody pair is from MesoScale Discovery. The human IFN-α multi-subtype antibody (PBL Biomedical Laboratories) captures all IFN-α subtypes except IFN-αF (IFNA21). Standards consist of recombinant human TNF-α (R&D Systems, Minneapolis, Minn.) and IFN-α (PBL Biomedical Laboratories). Samples and separate standards are added at the time of analysis to each MSD plate. Two human IFN-α detection antibodies (Cat. Nos. 21112 & 21100, PBL) are used in a two to one ratio (weight:weight) to each other to determine the IFN-α concentrations. The cytokine-specific detection antibodies are labeled with the SULFO-TAG reagent (MSD). After adding the SULFO-TAG labeled detection antibodies to the wells, each well's electrochemoluminescent levels are read using MSD's SECTOR HTS READER. Results are expressed in pg/mL upon calculation with known cytokine standards.

Assay Data and Analysis

In total, the data output of the assay consists of concentration values of TNF-α or IFN-α (y-axis) as a function of compound concentration (x-axis).

A plate-wise scaling is performed within a given experiment aimed at reducing plate-to-plate variability associated within the same experiment. First, the greater of the median DMSO (DMSO control wells) or the experimental background (usually 20 pg/mL for IFN-α and 40 pg/mL for TNF-α) is subtracted from each reading. Negative values that may result from background subtraction are set to zero. Each plate within a given experiment has a reference compound that serves as a control. This control is used to calculate a median expected area under the curve across all plates in the assay. A plate-wise scaling factor is calculated for each plate as a ratio of the area of the reference compound on the particular plate to the median expected area for the entire experiment. The data from each plate are then multiplied by the plate-wise scaling factor for all plates. Only data from plates bearing a scaling factor of between 0.5 and 2.0 (for both cytokines IFN-α, TNF-α) are reported. Data from plates with scaling factors outside the above mentioned interval are retested until they bear scaling factors inside the above mentioned interval. The above method produces a scaling of the y-values without altering the shape of the curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91). The median expected area is the median area across all plates that are part of a given experiment.

A second scaling may also be performed to reduce inter-experiment variability (across multiple experiments). All background-subtracted values are multiplied by a single adjustment ratio to decrease experiment-to-experiment variability. The adjustment ratio is the area of the reference compound in the new experiment divided by the expected area of the reference compound based on an average of previous experiments (unadjusted readings). This results in the scaling of the reading (y-axis) for the new data without changing the shape of the dose-response curve. The reference compound used is 2-[4-amino-2-ethoxymethyl-6,7,8,9-tetrahydro-α,α-dimethyl-1H-imidazo[4,5-c]quinolin-1-yl]ethanol hydrate (U.S. Pat. No. 5,352,784; Example 91) and the expected area is the sum of the median dose values from an average of previous experiments.

The minimum effective concentration is calculated based on the background-subtracted, reference-adjusted results for a given experiment and compound. The minimum effective concentration (μmolar) is the lowest of the tested compound concentrations that induces a response over a fixed cytokine concentration for the tested cytokine (usually 20 pg/mL for IFN-α and 40 pg/mL for TNF-α). The maximal response is the maximal amount of cytokine (pg/ml) produced in the dose-response.

TNF-α Inhibition in Mouse Cells

Certain compounds of the invention may modulate cytokine biosynthesis by inhibiting production of tumor necrosis factor α (TNF-α) when tested using the method described below.

The mouse macrophage cell line Raw 264.7 is used to assess the ability of compounds to inhibit tumor necrosis factor-α (TNF-α) production upon stimulation by lipopolysaccharide (LPS).

Single Concentration Assay:
Blood Cell Preparation for Culture

Raw cells (ATCC) are harvested by gentle scraping and then counted. The cell suspension is brought to $3\times10^5$ cells/mL in RPMI with 10% fetal bovine serum (FBS). Cell suspension (100 μL) is added to 96-well flat bottom sterile tissues culture plates (Becton Dickinson Labware, Lincoln Park, N.J.). The final concentration of cells is $3\times10^4$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 5 μM. LPS (Lipopolysaccharide from Salmonella typhimurium, Sigma-Aldrich) is diluted with colorless RPMI to the $EC_{70}$ concentration as measured by a dose response assay.

Incubation

A solution of test compound (1 μl) is added to each well. The plates are mixed on a microtiter plate shaker for 1 minute and then placed in an incubator. Twenty minutes later the solution of LPS (1 μL, $EC_{70}$ concentration ~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from Biosource International, Camarillo, Calif.). Results are expressed in pg/mL. TNF-α expression upon LPS stimulation alone is considered a 100% response.

Dose Response Assay:
Blood Cell Preparation for Culture

Raw cells (ATCC) are harvested by gentle scraping and then counted. The cell suspension is brought to $4\times10^5$ cells/mL in RPMI with 10% FBS. Cell suspension (250 μL) is added to 48-well flat bottom sterile tissues culture plates (Costar, Cambridge, Mass.). The final concentration of cells is $1\times10^5$ cells/well. The plates are incubated for 3 hours. Prior to the addition of test compound the medium is replaced with colorless RPMI medium with 3% FBS.

Compound Preparation

The compounds are solubilized in dimethyl sulfoxide (DMSO). The DMSO concentration should not exceed a final concentration of 1% for addition to the culture wells. Compounds are tested at 0.03, 0.1, 0.3, 1, 3, 5 and 10 μM. LPS (Lipopolysaccharide from Salmonella typhimurium, Sigma-Aldrich) is diluted with colorless RPMI to the $EC_{70}$ concentration as measured by dose response assay.

Incubation

A solution of test compound (200 μl) is added to each well. The plates are mixed on a microtiter plate shaker for 1 minute and then placed in an incubator. Twenty minutes later the solution of LPS (200 μL, $EC_{70}$ concentration ~10 ng/ml) is added and the plates are mixed for 1 minute on a shaker. The plates are incubated for 18 to 24 hours at 37° C. in a 5% carbon dioxide atmosphere.

TNF-α Analysis

Following the incubation the supernatant is removed with a pipet. TNF-α concentration is determined by ELISA using a mouse TNF-α kit (from Biosource International, Camarillo, Calif.). Results are expressed in pg/mL. TNF-α expression upon LPS stimulation alone is considered a 100% response.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

The invention claimed is:
1. A compound of formula (II):

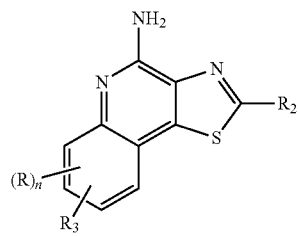

wherein:
$R_2$ is alkyl;
$R_3$ is —O—Z—Ar;
Z is selected from the group consisting of a bond and alkylene, wherein alkylene is optionally interrupted with —O—;
Ar is selected from the group consisting of aryl and heteroaryl both of which can be unsubstituted or can be substituted by one or more substituents independently selected from the group consisting of alkyl, alkenyl, alkoxy, methylenedioxy, haloalkyl, haloalkoxy, halogen, nitro, hydroxy, hydroxyalkyl, mercapto, cyano, carboxy, formyl, aryl, aryloxy, arylalkyleneoxy, heteroaryl, heteroaryloxy, heteroarylalkyleneoxy, heterocyclyl, heterocyclylalkylene, amino, alkylamino, and dialkylamino;

R is selected from the group consisting of alkyl, alkoxy, hydroxy, halogen, and trifluoromethyl; and n is 0 or 1;

or a pharmaceutically acceptable salt thereof.

2. The compound or salt of claim 1 wherein $R_3$ is attached at the 7-position.

3. The compound or salt of claim 1 wherein n is 0.

4. The compound or salt claim 1 wherein Z is a bond, alkylene, or alkylene interrupted with one —O—.

5. The compound or salt of claim 4 wherein Z is —$C_{1-3}$ alkylene-.

6. The compound or salt of claim 5 wherein Z is —$CH_2$—.

7. The compound or salt of claim 1 wherein Ar is selected from the group consisting of phenyl, naphthyl, pyridyl, pyrrolyl, thienyl, furyl, isoxazolyl, thiazolyl, imidazolyl, benzimidazolyl, 1,2,3-triazolyl, indolyl, benzothiazolyl, and oxazolyl; each of which is unsubstituted or substituted by one or more substituents independently selected from the group consisting of alkyl, alkoxy, nitro, cyano, halogen, amino, alkylamino, dialkylamino, trifluoromethoxy, aryl, and hydroxyalkyl.

8. The compound or salt of claim 7 wherein Ar is selected from the group consisting of phenyl, naphthyl, pyridyl, pyrrolyl, thienyl, furyl, isoxazolyl, thiazolyl, and imidazolyl; each of which is unsubstituted or substituted by one or more substituents independently selected from the group consisting of alkyl, alkoxy, nitro, cyano, halogen, amino, alkylamino, dialkylamino, and trifluoromethoxy.

9. The compound or salt of claim 8 wherein Ar is phenyl substituted by one or more substituents independently selected from the group consisting of alkyl, alkoxy, nitro, cyano, halogen, amino, alkylamino, dialkylamino, and trifluoromethoxy.

10. The compound or salt of claim 1 wherein $R_2$ is $C_{1-8}$ alkyl.

11. The compound or salt of claim 10 wherein $R_2$ is $C_{1-4}$ alkyl.

12. The compound or salt of claim 11 wherein $R_2$ is methyl, ethyl, n-propyl, n-butyl.

13. A pharmaceutical composition comprising a therapeutically effective amount of a compound or salt of claim and a pharmaceutically acceptable carrier.

* * * * *